(12) United States Patent
Williamson et al.

(10) Patent No.: US 10,220,386 B2
(45) Date of Patent: Mar. 5, 2019

(54) SYSTEMS, METHODS, AND APPARATUSES TO IMAGE A SAMPLE FOR BIOLOGICAL OR CHEMICAL ANALYSIS

(71) Applicant: ILLUMINA, INC., San Diego, CA (US)

(72) Inventors: Erik Williamson, San Diego, CA (US);
Bryan Crane, San Diego, CA (US);
Patrick Leung, San Bruno, CA (US);
Drew Verkade, Carlsbad, CA (US);
Mark T. Reed, Menlo Park, CA (US)

(73) Assignee: ILLUMINA, INC., San Diego, CA (US)

( * ) Notice: Subject to any disclaimer, the term of this patent is extended or adjusted under 35 U.S.C. 154(b) by 587 days.

(21) Appl. No.: 14/550,956

(22) Filed: Nov. 22, 2014

(65) Prior Publication Data

US 2015/0151297 A1 Jun. 4, 2015

Related U.S. Application Data

(63) Continuation of application No. 13/273,666, filed on Oct. 14, 2011, now Pat. No. 8,951,781.
(Continued)

(51) Int. Cl.
*B01L 3/00* (2006.01)
*B01L 9/00* (2006.01)
(Continued)

(52) U.S. Cl.
CPC ......... *B01L 3/502715* (2013.01); *B01L 9/527* (2013.01); *G01N 21/05* (2013.01);
(Continued)

(58) Field of Classification Search
CPC ................... B01L 2200/027; B01L 3/502715
See application file for complete search history.

(56) References Cited

U.S. PATENT DOCUMENTS

| 4,863,243 A | 9/1989 | Wakefield |
| 5,324,633 A | 6/1994 | Fodor et al. |

(Continued)

FOREIGN PATENT DOCUMENTS

| CN | 1525176 A | 9/2004 |
| CN | 1710378 | 12/2005 |

(Continued)

OTHER PUBLICATIONS

Ronaghi, M. et al. (1996) "Real-time DNA sequencing using detection of pyrophosphate release." Analytical Biochemistry 242(1), 84-9.

(Continued)

*Primary Examiner* — Jonathan M Hurst
(74) *Attorney, Agent, or Firm* — Illumina, Inc.

(57) ABSTRACT

A fluidic device holder configured to orient a fluidic device. The device holder includes a support structure configured to receive a fluidic device. The support structure includes a base surface that faces in a direction along the Z-axis and is configured to have the fluidic device positioned thereon. The device holder also includes a plurality of reference surfaces facing in respective directions along an XY-plane. The device holder also includes an alignment assembly having an actuator and a movable locator arm that is operatively coupled to the actuator. The locator arm has an engagement end. The actuator moves the locator arm between retracted and biased positions to move the engagement end away from and toward the reference surfaces. The locator arm is configured to hold the fluidic device against the reference surfaces when the locator arm is in the biased position.

17 Claims, 39 Drawing Sheets

Related U.S. Application Data

(60) Provisional application No. 61/431,425, filed on Jan. 10, 2011, provisional application No. 61/431,429, filed on Jan. 10, 2011, provisional application No. 61/431,439, filed on Jan. 11, 2011, provisional application No. 61/431,440, filed on Jan. 11, 2011, provisional application No. 61/438,486, filed on Feb. 1, 2011, provisional application No. 61/438,567, filed on Feb. 1, 2011, provisional application No. 61/438,530, filed on Feb. 1, 2011.

(51) Int. Cl.
  *G01N 21/05* (2006.01)
  *B01L 7/00* (2006.01)

(52) U.S. Cl.
  CPC ............ *B01L 7/52* (2013.01); *B01L 2200/025* (2013.01); *B01L 2200/027* (2013.01); *B01L 2200/04* (2013.01); *B01L 2200/0689* (2013.01); *B01L 2300/022* (2013.01); *B01L 2300/041* (2013.01); *B01L 2300/043* (2013.01); *B01L 2300/0816* (2013.01); *B01L 2300/0877* (2013.01); *G01N 2021/058* (2013.01); *Y10T 436/25* (2015.01)

(56) References Cited

U.S. PATENT DOCUMENTS

| | | | |
|---|---|---|---|
| 5,451,683 A | 9/1995 | Barrett et al. | |
| 5,482,867 A | 1/1996 | Barrett et al. | |
| 5,491,074 A | 2/1996 | Aldwin et al. | |
| 5,624,711 A | 4/1997 | Sundberg et al. | |
| 5,641,658 A | 6/1997 | Adams et al. | |
| 5,744,305 A | 4/1998 | Fodor et al. | |
| 5,795,716 A | 8/1998 | Chee et al. | |
| 5,831,070 A | 11/1998 | Pease et al. | |
| 5,856,101 A | 1/1999 | Hubbell et al. | |
| 5,858,659 A | 1/1999 | Sapolsky et al. | |
| 5,874,219 A | 2/1999 | Rava et al. | |
| 5,968,740 A | 10/1999 | Fodor et al. | |
| 5,974,164 A | 10/1999 | Chee | |
| 5,981,185 A | 11/1999 | Matson et al. | |
| 5,981,956 A | 11/1999 | Stern | |
| 6,022,963 A | 2/2000 | McGall et al. | |
| 6,025,601 A | 2/2000 | Trulson et al. | |
| 6,033,860 A | 3/2000 | Locjhart et al. | |
| 6,083,697 A | 7/2000 | Beecher et al. | |
| 6,090,555 A | 7/2000 | Fiekowsky et al. | |
| 6,136,269 A | 10/2000 | Winkler et al. | |
| 6,210,891 B1 | 4/2001 | Nyren et al. | |
| 6,258,568 B1 | 7/2001 | Nyren | |
| 6,266,459 B1 | 7/2001 | Walt et al. | |
| 6,274,320 B1 | 8/2001 | Rotheberg et al. | |
| 6,291,183 B1 | 9/2001 | Pirrung et al. | |
| 6,309,831 B1 | 10/2001 | Goldberg et al. | |
| 6,355,431 B1 | 3/2002 | Chee et al. | |
| 6,416,949 B1 | 7/2002 | Dower et al. | |
| 6,428,752 B1 | 8/2002 | Montagu | |
| 6,482,591 B2 | 11/2002 | Lockhart et al. | |
| 6,676,267 B2 | 1/2004 | Takase | |
| 6,770,441 B2 | 8/2004 | Dickinson et al. | |
| 6,859,570 B2 | 2/2005 | Walt et al. | |
| 7,001,792 B2 | 2/2006 | Sauer et al. | |
| 7,057,026 B2 | 6/2006 | Barnes et al. | |
| 7,115,400 B1 | 10/2006 | Adessi et al. | |
| 7,211,414 B2 | 5/2007 | Hardin | |
| 7,277,166 B2 | 10/2007 | Padmanabhan et al. | |
| 7,315,019 B2 | 1/2008 | Turner et al. | |
| 7,329,492 B2 | 2/2008 | Hardin et al. | |
| 7,329,860 B2 | 2/2008 | Feng et al. | |
| 7,358,078 B2 | 4/2008 | Chen et al. | |
| 7,405,281 B2 | 7/2008 | Xu et al. | |
| 7,595,883 B1 | 9/2009 | El Gamal et al. | |
| 7,622,294 B2 | 11/2009 | Walt et al. | |
| 2002/0055100 A1 | 5/2002 | Kawashima et al. | |
| 2003/0108867 A1 | 6/2003 | Chee et al. | |
| 2003/0108900 A1 | 6/2003 | Oliphant et al. | |
| 2003/0170684 A1 | 9/2003 | Fan | |
| 2003/0207295 A1 | 11/2003 | Gunderson et al. | |
| 2004/0002090 A1 | 1/2004 | Mayer et al. | |
| 2004/0096853 A1 | 5/2004 | Mayer | |
| 2004/0219661 A1* | 11/2004 | Chen ................. B01L 3/502715 435/286.5 |
| 2004/0238401 A1* | 12/2004 | Greenstein ............. B01L 9/527 206/701 |
| 2005/0042648 A1 | 2/2005 | Griffiths et al. | |
| 2005/0064460 A1 | 3/2005 | Holliger et al. | |
| 2005/0079510 A1 | 4/2005 | Berka et al. | |
| 2005/0100900 A1 | 5/2005 | Kawashima et al. | |
| 2005/0130173 A1 | 6/2005 | Leamin et al. | |
| 2005/0170493 A1* | 8/2005 | Patno .................... B01F 5/0256 435/287.2 |
| 2005/0181394 A1 | 8/2005 | Steemers et al. | |
| 2005/0227252 A1 | 10/2005 | Moon et al. | |
| 2006/0078931 A1 | 4/2006 | Oh et al. | |
| 2006/0132879 A1 | 6/2006 | Kim | |
| 2006/0180489 A1 | 8/2006 | Guiney et al. | |
| 2006/0275852 A1 | 12/2006 | Montagu et al. | |
| 2007/0099208 A1 | 5/2007 | Drmanac et al. | |
| 2007/0128624 A1 | 6/2007 | Gormley et al. | |
| 2007/0166195 A1* | 7/2007 | Padmanabhan ... B01L 3/502715 422/68.1 |
| 2007/0166705 A1 | 7/2007 | Milton et al. | |
| 2008/0009420 A1 | 1/2008 | Schroth et al. | |
| 2008/0108082 A1 | 5/2008 | Rank et al. | |
| 2008/0182301 A1 | 7/2008 | Handique et al. | |
| 2008/0280773 A1 | 11/2008 | Fedurco et al. | |
| 2009/0088327 A1 | 4/2009 | Rigatti et al. | |
| 2009/0130719 A1 | 5/2009 | Handique | |
| 2009/0155123 A1 | 6/2009 | Williams et al. | |
| 2009/0272914 A1 | 11/2009 | Feng et al. | |
| 2010/0033728 A1 | 2/2010 | Jacobson et al. | |
| 2010/0157086 A1 | 2/2010 | Segale | |
| 2010/0133510 A1 | 6/2010 | Kim et al. | |
| 2012/0196758 A1 | 8/2012 | Klausing et al. | |

FOREIGN PATENT DOCUMENTS

| | | |
|---|---|---|
| CN | 1794034 | 6/2006 |
| CN | 201550179 U | 8/2010 |
| CN | 103501907 B | 6/2015 |
| DE | 102006022511 | 8/2007 |
| EP | 0492326 A | 7/1992 |
| EP | 1818645 | 8/2007 |
| EP | 1898219 A2 | 3/2008 |
| JP | 2006201404 A | 8/2006 |
| WO | WO 91/06678 | 5/1991 |
| WO | WO 98/44151 | 10/1998 |
| WO | WO 98/59066 | 12/1998 |
| WO | WO 00/18957 | 4/2000 |
| WO | WO 00/63437 | 10/2000 |
| WO | WO 00/73766 | 12/2000 |
| WO | WO 02/072264 | 9/2002 |
| WO | WO 03/087410 | 10/2003 |
| WO | WO 04/018497 | 3/2004 |
| WO | WO 04/024328 | 3/2004 |
| WO | WO 05/010145 | 2/2005 |
| WO | WO 05/033681 | 4/2005 |
| WO | WO07010252 | 1/2007 |
| WO | WO 07/123744 | 11/2007 |
| WO | WO2008041002 | 4/2008 |
| WO | WO 2009/042862 | 4/2009 |
| WO | 2009/105609 A1 | 8/2009 |
| WO | WO 2009/137435 | 11/2009 |
| WO | 2011/071772 A2 | 6/2011 |

OTHER PUBLICATIONS

Deamer et al., "Characterization of Nucleic Acids by Nanopore Analysis," Acc. Chem. Res. 35:817-825 (2002).

(56) References Cited

OTHER PUBLICATIONS

Healy et al., "Nanopore-based single-molecule DNA analysis," Nanomedicine, Aug. 2007, vol. 2, No. 4, pp. 459-481.
Cockroft et al., "A Single-Molecule Nanopore Device Detects DNA Polymerase Activity with Single-Nucleotide Resolution," J. am. Chem. Soc. 130:818-820 (2008).
Soni et al., "Progress toward Ultrafast DNA Sequencing Using Solid-State Nanopores," Clin Chem. 53:1996-2001 (2007).
Lizardi et al., "Mutation detection and single-molecule counting using isothermal rolling-circle amplification" Nat. Genet. 19:225-232 (1998).
Dressman et al., "Transforming single DNA molecules into fluorescent magnetic particles for detection and enumeration of genetic variations," Proc. Natl. Acad. Sci. USA 100:8817-8822 (2003).
Bentley, D.R. et al. (2008) "Accurate whole human genome sequencing using reversible terminator chemistry." Nature, 456, 53-59.
Ronaghi, M. et al. (1998) "A sequencing method based on real-time pyrophosphate." Science 281(5375), 363; Science Jul. 17, 1998: vol. 281 No. 5375 pp. 363-365.
Li et al, "DNA molecules and configurations in a solid-state nanopore microscope," Nature Mater. 2, 611-615 (2003).
Ronaghi, "Pyrosequencing Sheds Light on DNA Sequencing," Genome Res. (2001) 11: 3-11.
PCT International Search and Written Opinion for international Application No. PCT/US2011/057221 dated Jul. 4, 2012.
Partial Search Report for International application No. PCT/US2011/057221, dated Mar. 12, 2012.
EP18172354, "Extended European Search Report," dated Jun. 12, 2018, 3 pages.

\* cited by examiner

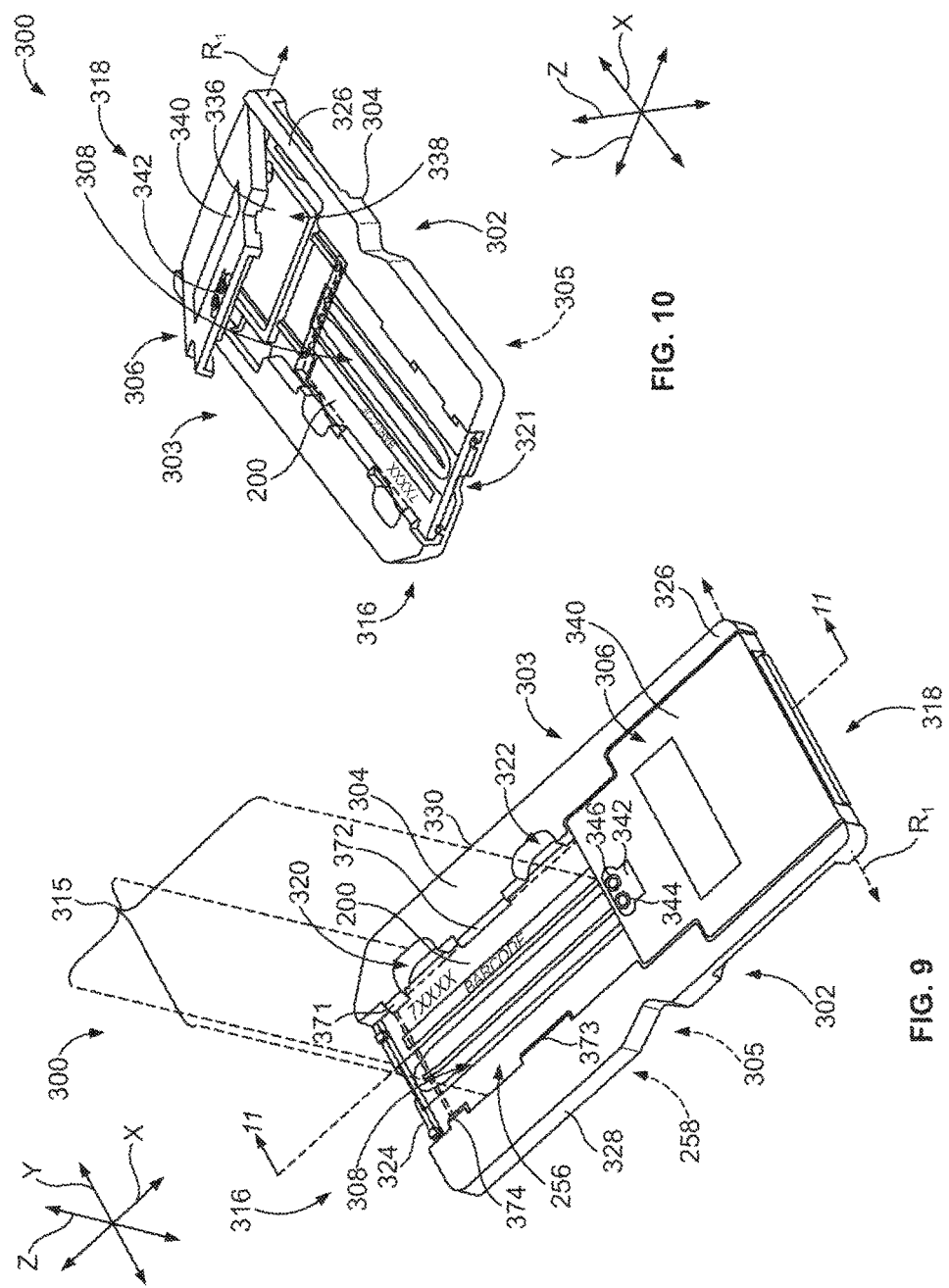

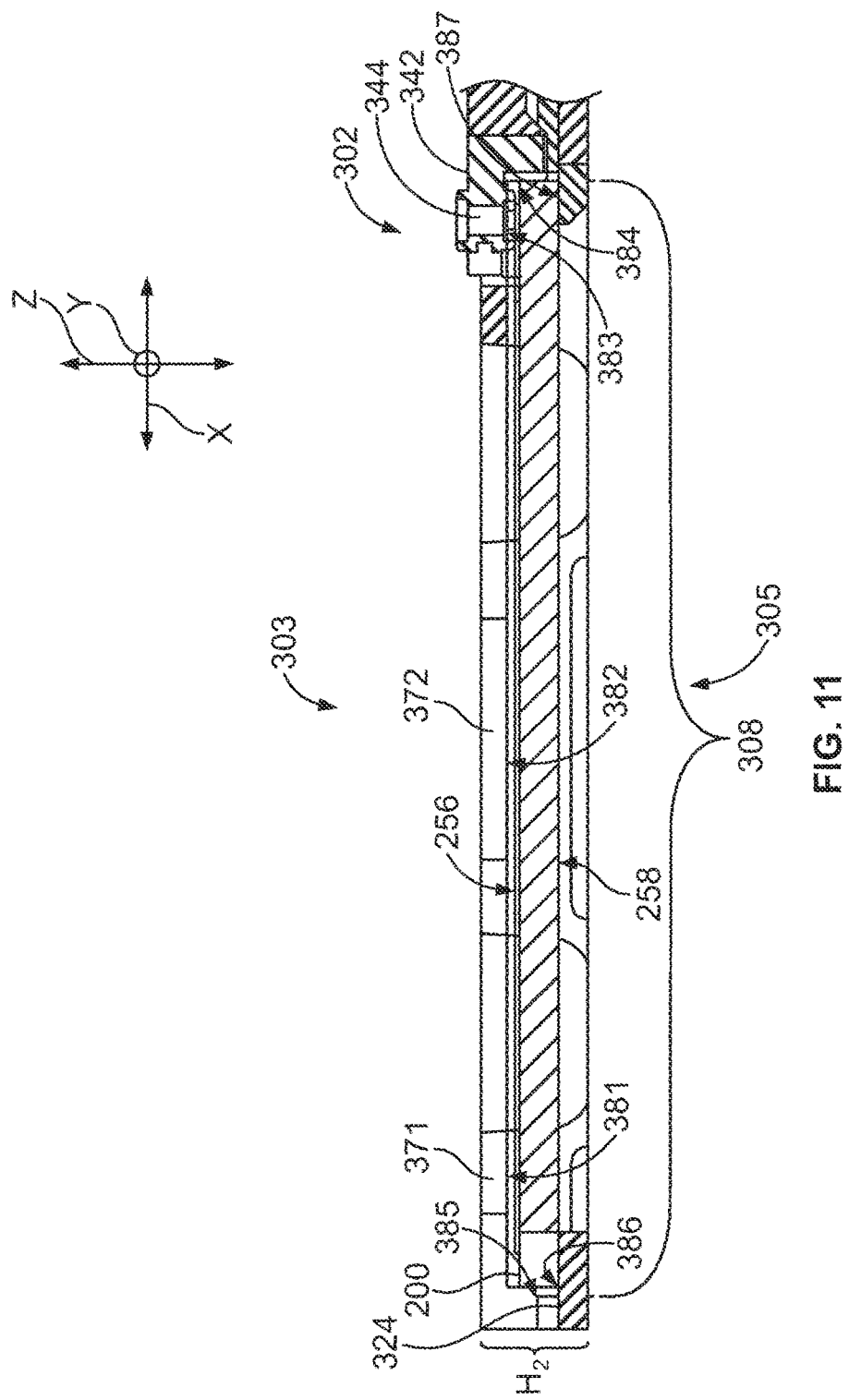

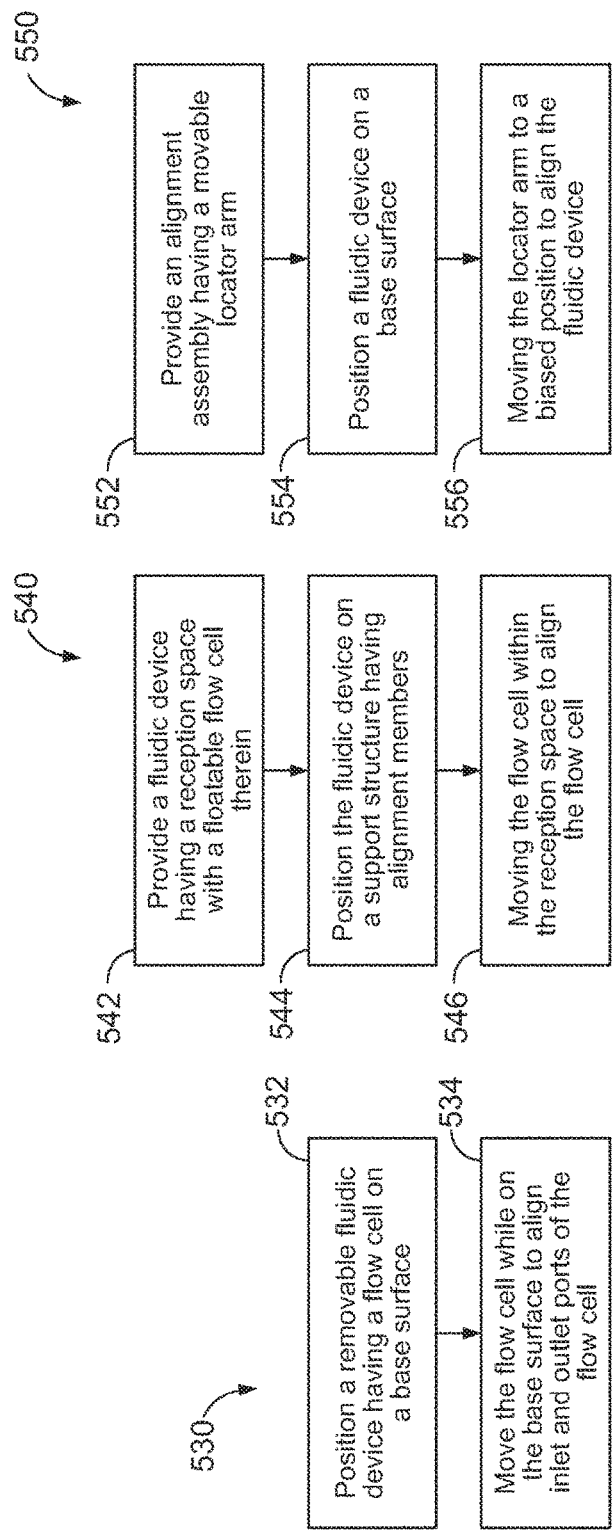

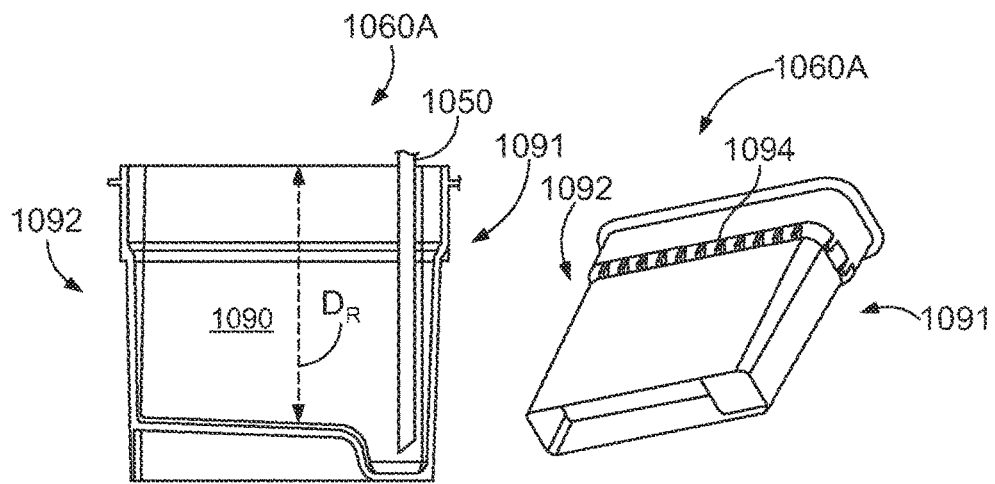
FIG. 35
FIG. 36
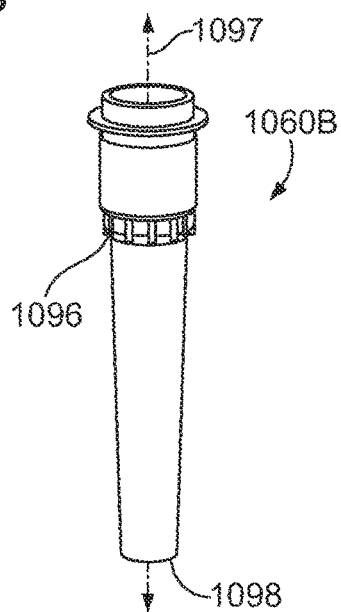
FIG. 37

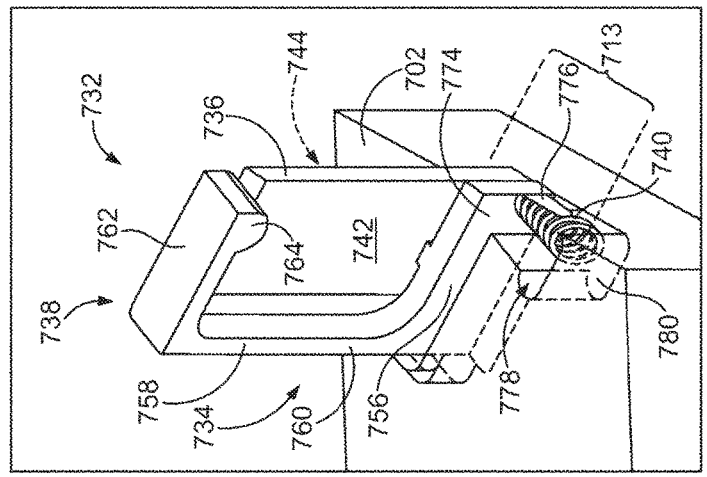
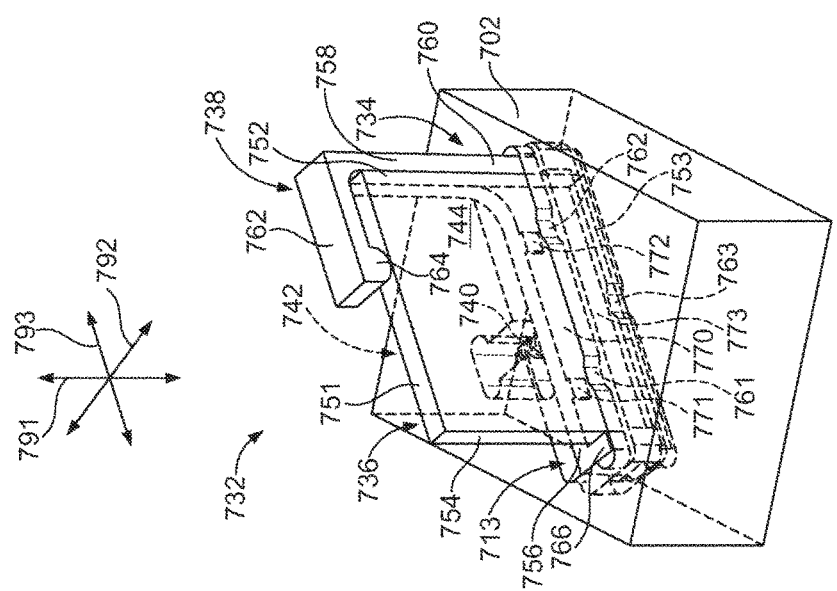
FIG. 44
FIG. 43

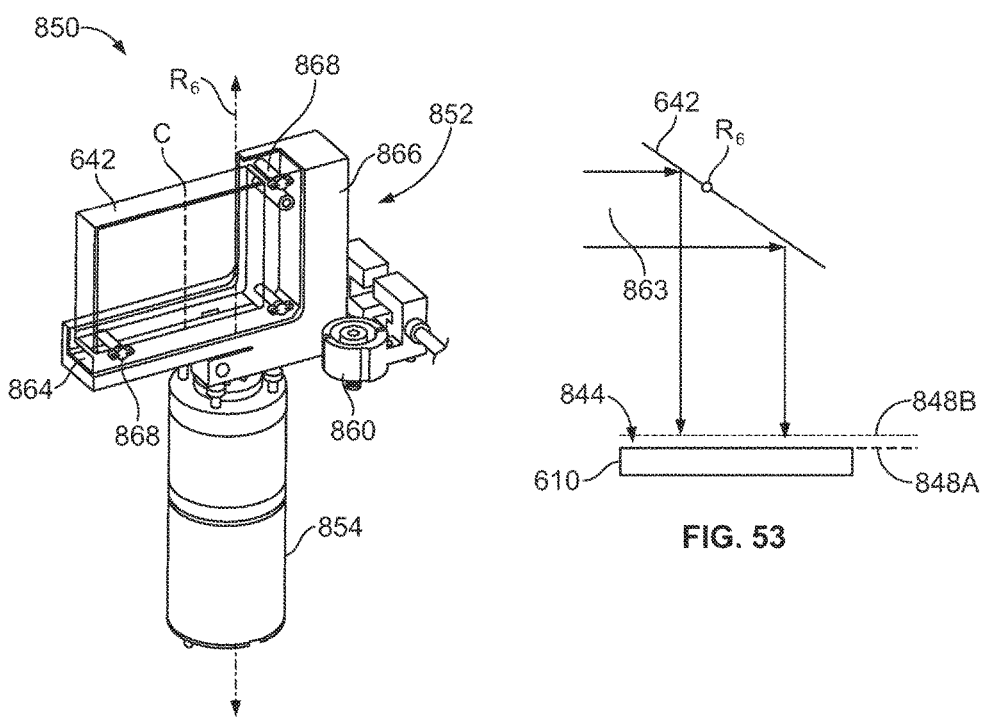
FIG. 52
FIG. 53
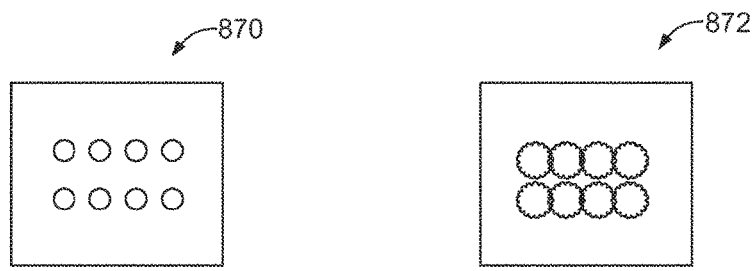
FIG. 54
FIG. 55

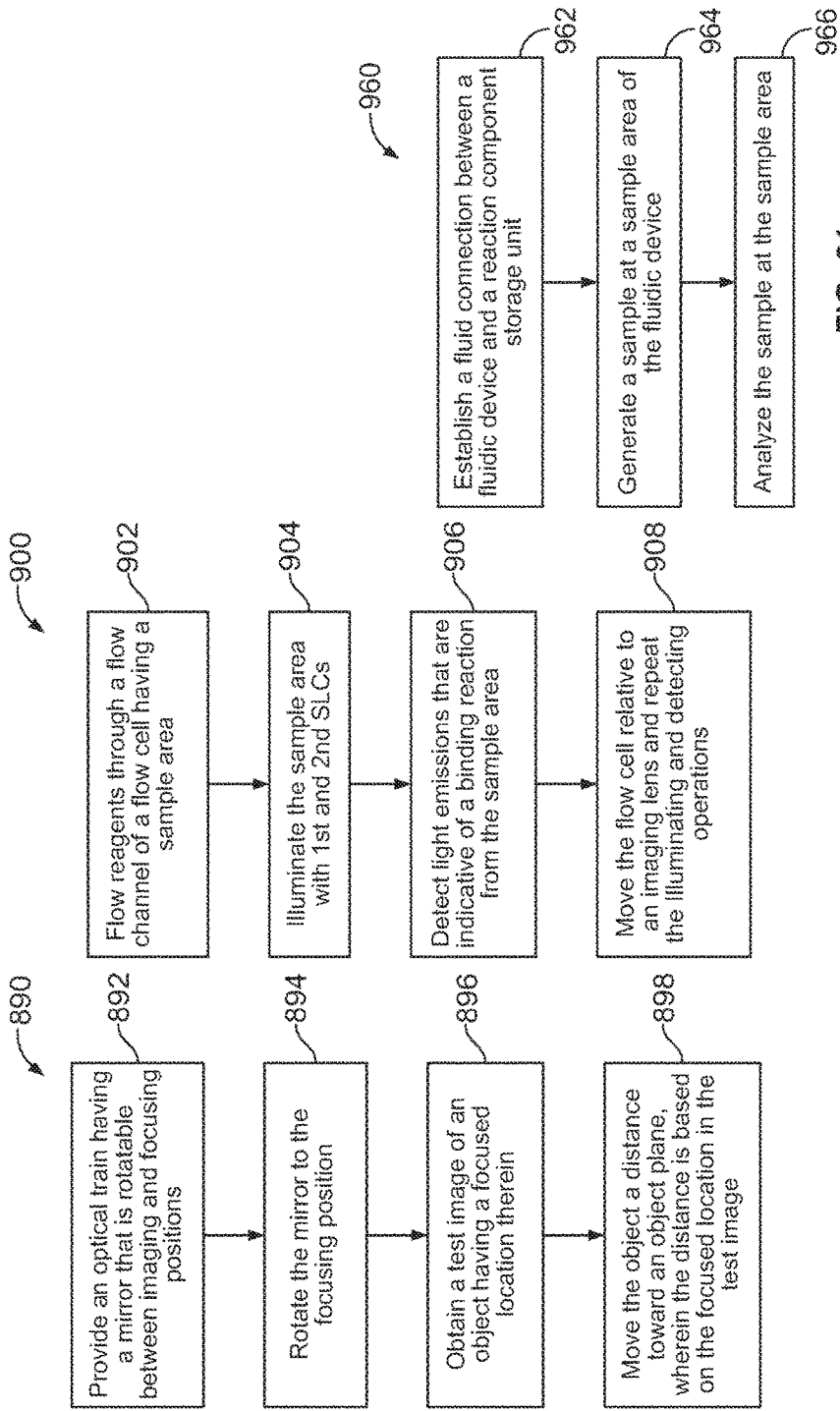

SYSTEMS, METHODS, AND APPARATUSES TO IMAGE A SAMPLE FOR BIOLOGICAL OR CHEMICAL ANALYSIS

CROSS REFERENCE TO RELATED APPLICATIONS

The present application is a continuation of U.S. application Ser. No. 13/273,666, filed on Oct. 14, 2011, which relates to and claims the benefit of U.S. Provisional Application Nos. 61/431,425, filed on Jan. 10, 2011; 61/431,429, filed on Jan. 10, 2011; 61/431,439, filed on Jan. 11, 2011; 61/431,440, filed on Jan. 11, 2011; 61/438,486, filed on Feb. 1, 2011; 61/438,567, filed on Feb. 1, 2011; 61/438,530, filed on Feb. 1, 2011. Each of the above applications is herein incorporated by reference in its entirety.

BACKGROUND OF THE INVENTION

Embodiments of the present invention relate generally to biological or chemical analysis and more particularly, to assay systems having fluidic devices, optical assemblies, and/or other apparatuses that may be used in detecting desired reactions in a sample.

Various assay protocols used for biological or chemical research are concerned with performing a large number of controlled reactions. In some cases, the controlled reactions are performed on support surfaces. The desired reactions may then be observed and analyzed to help identify properties or characteristics of the chemicals involved in the desired reaction. For example, in some protocols, a chemical moiety that includes an identifiable label (e.g., fluorescent label) may selectively bind to another chemical moiety under controlled conditions. These chemical reactions may be observed by exciting the labels with radiation and detecting light emissions from the labels. The light emissions may also be provided through other means, such as chemiluminescence.

Examples of such protocols include DNA sequencing. In one sequencing-by-synthesis (SBS) protocol, clusters of clonal amplicons are formed through bridge PCR on a surface of a flow channel. After generating the clusters of clonal amplicons, the amplicons may be "linearized" to make single stranded DNA (sstDNA). A series of reagents is flowed into the flow cell to complete a cycle of sequencing. Each sequencing cycle extends the sstDNA by a single nucleotide (e.g., A, T, G, C) having a unique fluorescent label. Each nucleotide has a reversible terminator that allows only a single-base incorporation to occur in one cycle. After nucleotides are added to the sstDNAs clusters, an image in four channels is taken (i.e., one for each fluorescent label). After imaging, the fluorescent label and the terminator are chemically cleaved from the sstDNA and the growing DNA strand is ready for another cycle. Several cycles of reagent delivery and optical detection can be repeated to determine the sequences of the clonal amplicons.

However, systems configured to perform such protocols may have limited capabilities and may not be cost-effective. Thus, there is a general need for improved systems, methods, and apparatuses that are capable of performing or being used during assay protocols, such as the SBS protocol described above, in a cost-effective, simpler, or otherwise improved manner.

BRIEF DESCRIPTION OF THE INVENTION

In accordance with one embodiment, a fluidic device for analyzing samples is provided. The fluidic device includes a flow cell having inlet and outlet ports and a flow channel extending therebetween. The flow cell is configured to hold a sample-of-interest. The fluidic device also includes a housing having a reception space that is configured to receive the flow cell. The reception space is sized and shaped to permit the flow cell to float relative to the housing. The fluidic device also includes a gasket that is coupled to the housing. The gasket has inlet and outlet passages and comprises a compressible material. The gasket is positioned relative to the reception space so that the inlet and outlet ports of the flow cell are approximately aligned with the inlet and outlet passages of the gasket, respectively.

In another embodiment, a removable cartridge configured to hold and facilitate positioning a flow cell for imaging is provided. The cartridge includes a removable housing that has a reception space configured to hold the flow cell substantially within an object plane. The housing includes a pair of housing sides that face in opposite directions. The reception space extends along at least one of the housing sides so that the flow cell is exposed to an exterior of the housing through said at least one of the housing sides. The cartridge also includes a cover member that is coupled to the housing and includes a gasket. The gasket has inlet and outlet passages and comprises a compressible material. The gasket is configured to be mounted over an exposed portion of the flow cell when the flow cell is held by the housing.

In yet another embodiment, a method of positioning a fluidic device for sample analysis is provided. The method includes positioning a removable fluidic device on a support surface of an imaging system. The device has a reception space, a flow cell located within the reception space, and a gasket. The flow cell extends along an object plane in the reception space and is floatable relative to the gasket within the object plane. The method also includes moving the flow cell within the reception space while on the support surface so that inlet and outlet ports of the flow cell are approximately aligned with inlet and outlet passages of the gasket.

In another embodiment, a method of positioning a fluidic device for sample analysis is provided. The method includes providing a fluidic device having a housing that includes a reception space and a floatable flow cell located within the reception space. The housing has recesses that are located immediately adjacent to the reception space. The method also includes positioning the fluidic device on a support structure having alignment members. The alignment members are inserted through corresponding recesses. The method also includes moving the flow cell within the reception space. The alignment members engage edges of the flow cell when the flow cell is moved within the reception space.

In another embodiment, a fluidic device holder is provided that is configured to orient a sample area with respect to mutually perpendicular X, Y, and Z-axes. The device holder includes a support structure that is configured to receive a fluidic device. The support structure includes a base surface that faces in a direction along the Z-axis and is configured to have the device positioned thereon. The device holder also includes a plurality of reference surfaces in respective directions along an XY-plane and an alignment assembly that includes an actuator and a movable locator arm that is operatively coupled to the actuator. The locator arm has an engagement end. The actuator moves the locator arm between retracted and biased positions to move the engagement end toward and away from the reference surfaces. The locator arm is configured to hold the device against the reference surfaces when the locator arm is in the biased position.

In another embodiment, a fluidic device holder is provided that includes a support structure having a loading region for receiving a fluidic device. The support structure includes a base surface that partially defines the loading region and is configured to have the device positioned thereon. The device holder includes a cover assembly that is coupled to the support structure and is configured to be removably mounted over the device. The cover assembly includes a cover housing having housing legs and a bridge portion that joins the housing legs. The housing legs extend in a common direction and have a viewing space that is located therebetween. The viewing space is positioned above the loading region.

In another embodiment, a method for orienting a sample area with respect to mutually perpendicular X, Y, and Z-axes is provided. The method includes providing an alignment assembly that has a movable locator arm having an engagement end. The locator arm is movable between retracted and biased positions. The method also includes positioning a fluidic device on a base surface that faces in a direction along the Z-axis and between a plurality of reference surfaces that face in respective directions along an XY-plane. The device has a sample area. The method also includes moving the locator arm to the biased position. The locator arm presses the device against the reference surfaces such that the device is held in a fixed position.

In yet another embodiment, an optical assembly is provided that includes a base plate having a support side and a component-receiving space along the support side. The component-receiving space is at least partially defined by a reference surface. The optical assembly also includes an optical component having an optical surface that is configured to reflect light or transmit light therethrough. The optical assembly also includes a mounting device that has a component retainer and a biasing element that is operatively coupled to the retainer. The retainer holds the optical component so that a space portion of the optical surface faces the reference surface and a path portion of the optical surface extends beyond the support side into an optical path. The biasing element provides an alignment force that holds the optical surface against the reference surface. In particular embodiments, the component-receiving space is a component cavity extending a depth into the base plate from the support side of the base plate. The optical and reference surfaces can have predetermined contours that are configured to position the optical surface in a predetermined orientation.

In another embodiment, a method of assembling an optical train is provided. The method includes providing a base plate that has a support side and a component-receiving space along the support side. The component-receiving space is at least partially defined by a reference surface. The method also includes inserting an optical component into the component-receiving space. The optical component has an optical surface that is configured to reflect light or transmit light therethrough. The optical surface has a space portion that faces the reference surface and a path portion that extends beyond the support side into an optical path. The method also includes providing an alignment force that holds the optical surface against the reference surface. In particular embodiments, the component-receiving space is a component cavity extending a depth into the base plate from the support side of the base plate. The optical and reference surfaces can have predetermined contours that are configured to position the optical surface in a predetermined orientation.

In another embodiment, an optical imaging system is provided that includes an object holder to hold and move an object and a detector to detect optical signals from the object at a detector surface. The imaging system also includes an optical train that is configured to direct the optical signals onto the detector surface. The optical train has an object plane that is proximate to the object holder and an image plane that is proximate to the detector surface. The optical train includes a mirror that is rotatable between an imaging position and a focusing position. The imaging system also includes an image analysis module that is configured to analyze a test image detected at the detector surface when the mirror is in the focusing position. The test image has an optimal degree-of-focus at a focused location in the test image. The focused location in the test image is indicative of a position of the object with respect to the object plane. The object holder is configured to move the object toward the object plane based on the focused location.

In another embodiment, a method for controlling focus of an optical imaging system is provided. The method includes providing an optical train that is configured to direct optical signals onto a detector surface. The optical train has an object plane that is proximate to an object and an image plane that is proximate to the detector surface. The optical train includes a mirror that is rotatable between an imaging position and a focusing position. The method also includes rotating the mirror to the focusing position and obtaining a test image of the object when the mirror is in the focusing position. The test image has an optimal degree-of-focus at a focused location in the test image. The focused location is indicative of a position of the object with respect to the object plane. The method also includes moving the object toward the object plane based on the focused location.

In another embodiment, an optical imaging system is provided that includes a sample holder configured to hold a flow cell. The flow cell includes a flow channel having a sample area. The imaging system also includes a flow system that is coupled to the flow cell and configured to direct reagents through the flow channel to the sample area. The imaging system also includes an optical train that is configured to direct excitation light onto the sample area and first and second light sources. The first and second light sources have fixed positions with respect to the optical train. The first and second light sources provide first and second optical signals, respectively, for exciting the biomolecules. The imaging system also includes a system controller that is communicatively coupled to the first and second light sources and to the flow system. The controller is configured to activate the flow system to flow the reagents to the sample area and activate the first and second light sources after a predetermined synthesis time period. The light sources can be, for example, lasers or semiconductor light sources (SLSs), such as laser diodes or light emitting diodes (LEDs).

In another embodiment, a method of performing a biological assay is provided. The method includes flowing reagents through a flow channel having a sample area. The sample area includes biomolecules that are configured to chemically react with the reagents. The method also includes illuminating the sample area with first and second light sources. The first and second light sources provide first and second optical signals, respectively. The biomolecules provide light emissions indicative of a binding reaction when illuminated by the first or second light sources. The method also includes detecting the light emissions from the sample area. The light sources can be, for example, lasers or semiconductor light sources (SLSs), such as a laser diodes or light emitting diodes (LEDs).

In another embodiment, a flow cell is provided that includes a first layer that has a mounting surface and an outer surface that face in opposite directions and that define a thickness therebetween. The flow cell also includes a second layer having a channel surface and an outer surface that face in opposite directions and that define a thickness therebetween. The second layer has a grooved portion that extends along the channel surface. The channel surface of the second layer is secured to the mounting surface. The flow cell also includes a flow channel that is defined by the grooved portion of the channel surface and a planar section of the mounting surface. The flow channel includes an imaging portion. The thickness of the second layer is substantially uniform along the imaging portion and is configured to transmit optical signals therethrough. The thickness of the first layer is substantially uniform along the imaging portion and is configured to permit uniform transfer of thermal energy therethrough.

In another embodiment, a light source module is provided that includes a module frame having a light passage and a light source that is secured to the module frame and oriented to direct optical signals through the light passage along an optical path. The light source module also includes an optical component that is secured to the module frame and has a fixed position and predetermined orientation with respect to the light source. The optical component is located within the light passage such that the optical component is within the optical path.

In another embodiment, an excitation light module is provided that includes a module frame and first and second semiconductor light sources (SLSs) that are secured to the module frame. The first and second SLSs have fixed positions with respect to each other. The first and second SLSs are configured to provide different excitation optical signals. The excitation light module also includes an optical component that is secured to the module frame and has a fixed position and predetermined orientation with respect to the first and second SLSs. The optical component permits the optical signals from the first SLS to transmit therethrough and reflects the optical signals from the second SLS. The reflected and transmitted optical signals are directed along a common path out of the module frame.

In one embodiment, a method of performing a biological or chemical assay is provided. The method includes establishing a fluid connection between a fluidic device having a sample area and a reaction component storage unit having a plurality of different reaction components for conducting one or more assays. The reaction components include sample-generation components and sample-analysis components. The method also includes generating a sample at the sample area of the fluidic device. The generating operation includes flowing different sample-generation components to the sample area and controlling reaction conditions at the sample area to generate the sample. The method also includes analyzing the sample at the sample area. The analyzing operation includes flowing at least one sample-analysis component to the sample area. Said at least one sample-analysis component reacts with the sample to provide optically detectable signals indicative of an event-of-interest. The generating and analyzing operations are conducted in an automated manner by the assay system.

In another embodiment, an assay system is provided that includes a fluidic device holder that is configured to hold a fluidic device and establish a fluid connection with the fluidic device. The assay system also includes a fluidic network that is configured to fluidicly connect the fluidic device to a reaction component storage unit. The assay system also includes a fluidic control system that is configured to selectively flow fluids from the storage unit through the fluidic device. Furthermore, the assay system includes a system controller that has a fluidic control module. The fluidic control module is configured to instruct the fluidic control system to (a) flow different sample-generation components from the storage unit to the sample area and control reaction conditions at the sample area to generate a sample; and (b) flow at least one sample-analysis component from the storage unit to the sample area. Said at least one sample-analysis component is configured to react with the sample to provide optically detectable signals indicative of an event-of-interest. The assay system also includes an imaging system that is configured to detect the optically detectable signals from the sample. The system controller is configured to automatically generate the sample and analyze the sample by selectively controlling the fluidic device holder, the fluidic control system, and the imaging system.

In another embodiment, a method of performing a biological or chemical assay is provided. The method includes: (a) providing a fluidic device having a sample area and a reaction component storage unit having a plurality of different reaction components for conducting one or more assays, the reaction components including sample-generation components and sample-analysis components; (b) flowing sample generation components according to a predetermined protocol to generate a sample at the sample area; (c) selectively controlling reaction conditions at the sample area to facilitate generating the sample; (d) flowing sample-analysis components to the sample area; and (e) detecting optical signals emitted from the sample area, the optical signals being indicative of an event-of-interest between the sample-analysis components and the sample; wherein (b)-(e) are conducted in an automated manner.

BRIEF DESCRIPTION OF THE DRAWINGS

FIG. 9 is a perspective view of a fluidic device formed in accordance with one embodiment.

FIG. 10 is another perspective view of the fluidic device of FIG. 9.

FIG. 11 is a cross-section of the fluidic device of FIG. 9 taken along the lines 11-11 in FIG. 9.

FIG. 25 is a block diagram of a method of positioning a fluidic device for sample analysis in accordance with one embodiment.

FIG. 26 is a block diagram illustrating a method of positioning a fluidic device for sample analysis in accordance with one embodiment.

FIG. 27 is a block diagram illustrating a method for orienting a sample area in accordance with one embodiment.

FIG. 35 is a side cross-section of a component well that may be used with the tray of FIG. 31.

FIG. 36 is a bottom perspective view of the component well of FIG. 35.

FIG. 37 is a perspective view of a component well that may be used with the tray of FIG. 31.

FIG. 43 is a perspective view of an optical component formed in accordance with one embodiment that may be used in the imaging system of FIG. 38.

FIG. 44 is a cut-away perspective view of the optical component of FIG. 43.

FIG. 52 is a perspective view of a rotatable mirror assembly that may be used in the image-focusing system of FIG. 51.

FIG. 53 is a schematic diagram of a rotatable mirror in an imaging position that may be used in the image-focusing system of FIG. 51.

FIGS. 54 and 55 illustrate sample images that may be obtained by the image-focusing system of FIG. 51.

FIG. 59 is a block diagram illustrating a method for controlling focus of an optical imaging system.

FIG. 60 illustrates a method for performing an assay for biological or chemical analysis.

FIG. 61 illustrates a method for performing an assay for biological or chemical analysis.

DETAILED DESCRIPTION OF THE INVENTION

Figure 1:
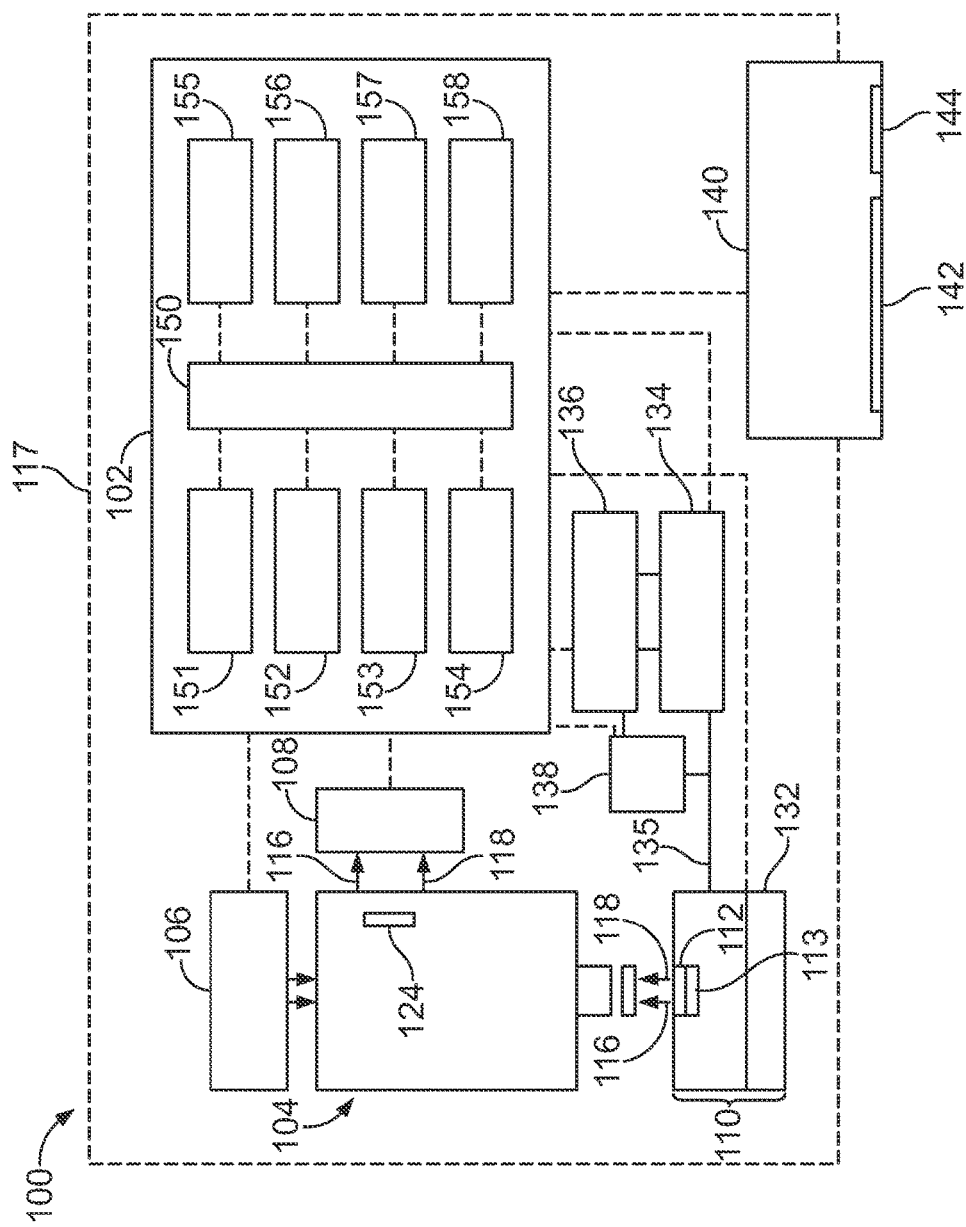
FIG. 1 is a block diagram of an assay system for performing biological or chemical assays formed in accordance with one embodiment.

Embodiments described herein include various systems, methods, assemblies, and apparatuses used to detect desired reactions in a sample for biological or chemical analysis. In some embodiments, the desired reactions provide optical signals that are detected by an optical assembly. The optical signals may be light emissions from labels or may be transmission light that has been reflected or refracted by the sample. For example, embodiments may be used to perform or facilitate performing a sequencing protocol in which sstDNA is sequenced in a flow cell. In particular embodiments, the embodiments described herein can also perform an amplification protocol to generate a sample-of-interest for sequencing.

As used herein, a "desired reaction" includes a change in at least one of a chemical, electrical, physical, and optical property or quality of a substance that is in response to a stimulus. For example, the desired reaction may be a chemical transformation, chemical change, or chemical interaction. In particular embodiments, the desired reactions are detected by an imaging system. The imaging system may include an optical assembly that directs optical signals to a sensor (e.g., CCD or CMOS). However, in other embodiments, the imaging system may detect the optical signals directly. For example, a flow cell may be mounted onto a CMOS sensor. However, the desired reactions may also be a change in electrical properties. For example, the desired reaction may be a change in ion concentration within a solution.

Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be addition or elimination of a proton, for example, detectable as a change in pH of a surrounding solution or environment.

The stimulus can be at least one of physical, optical, electrical, magnetic, and chemical. For example, the stimulus may be an excitation light that excites fluorophores in a substance. The stimulus may also be a change in a surrounding environment, such as a change in concentration of certain biomolecules (e.g., enzymes or ions) in a solution. The stimulus may also be an electrical current applied to a solution within a predefined volume. In addition, the stimulus may be provided by shaking, vibrating, or moving a reaction chamber where the substance is located to create a force (e.g., centripetal force). As used herein, the phrase "in response to a stimulus" is intended to be interpreted broadly and include more direct responses to a stimulus (e.g., when a fluorophore emits energy of a specific wavelength after absorbing incident excitation light) and more indirect responses to a stimulus in that the stimulus initiates a chain of events that eventually results in the response (e.g., incorporation of a base in pyrosequencing eventually resulting in chemiluminescence). The stimulus may be immediate (e.g., excitation light incident upon a fluorophore) or gradual (e.g., change in temperature of the surrounding environment).

As used herein, the phrase "activity that is indicative of a desired reaction" and variants thereof include any detectable event, property, quality, or characteristic that may be used to facilitate determining whether a desired reaction has occurred. The detected activity may be a light signal generated in fluorescence or chemiluminescence. The detected activity may also be a change in electrical properties of a solution within a predefined volume or along a predefined area. The detected activity may be a change in temperature.

Various embodiments include providing a reaction component to a sample. As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site (e.g., area where sample is located) in a solution or immobilized within a reaction site. The reaction components may interact directly or indirectly with the substance of interest.

In particular embodiments, the desired reactions are detected optically through an optical assembly. The optical assembly may include an optical train of optical components that cooperate with one another to direct the optical signals to an imaging device (e.g., CCD, CMOS, or photomultiplier tubes). However, in alternative embodiments, the sample region may be positioned immediately adjacent to an activity detector that detects the desired reactions without the use of an optical train. The activity detector may be able detect predetermined events, properties, qualities, or characteristics within a predefined volume or area. For example, an activity detector may be able to capture an image of the predefined volume or area. An activity detector may be able detect an ion concentration within a predefined volume of a solution or along a predefined area. Exemplary activity detectors include charged-coupled devices (CCD's) (e.g., CCD cameras); photomultiplier tubes (PMT's); molecular characterization devices or detectors, such as those used with nanopores; microcircuit arrangements, such as those described in U.S. Pat. No. 7,595,883, which is incorporated herein by reference in the entirety; and CMOS-fabricated sensors having field effect transistors (FET's), including chemically sensitive field effect transistors (chemFET), ion-sensitive field effect transistors (ISFET), and/or metal oxide semiconductor field effect transistors (MOSFET).

As used herein, the term "optical components" includes various elements that affect the propagation of optical signals. For example, the optical components may at least one of redirect, filter, shape, magnify, or concentrate the optical signals. The optical signals that may be affected include the optical signals that are upstream from the sample and the optical signals that are downstream from the sample. In a fluorescence-detection system, upstream components include those that direct excitation radiation toward the sample and downstream components include those that direct emission radiation away from the sample. Optical components may be, for example, reflectors, dichroics, beam splitters, collimators, lenses, filters, wedges, prisms, mirrors, detectors, and the like. Optical components also include bandpass filters, optical wedges, and optical devices similar to those described herein.

As used herein, the term "optical signals" or "light signals" includes electromagnetic energy capable of being detected. The term includes light emissions from labeled biological or chemical substances and also includes transmitted light that is refracted or reflected by optical substrates. Optical or light signals, including excitation radiation that is incident upon the sample and light emissions that are provided by the sample, may have one or more spectral patterns. For example, more than one type of label may be excited in an imaging session. In such cases, the different types of labels may be excited by a common excitation light source or may be excited by different excitation light sources at different times or at the same time. Each type of label may emit optical signals having a spectral pattern that is different from the spectral pattern of other labels. For example, the spectral patterns may have different emission spectra. The light emissions may be filtered to separately detect the optical signals from other emission spectra.

As used herein, when the term "different" is used with respect to light emissions (including emission spectra or other emission characteristics), the term may be interpreted broadly to include the light emissions being distinguishable or differentiable. For example, the emission spectra of the light emissions may have wavelength ranges that at least partially overlap so long as at least a portion of one emission spectrum does not completely overlap the other emission spectrum. Different emission spectra may also have the same or similar wavelength ranges, but have different intensities that are differentiable. Different optical signals can be distinguished based on different characteristics of excitation light that produces the optical signals. For example, in fluorescence resonance energy transfer (FRET) imaging, the light emissions may be the same but the cause (e.g., excitation optical signals) of the light emissions may be different. More specifically, a first excitation wavelength can be used to excite a donor fluorophore of a donor-acceptor pair such that FRET results in emission from the acceptor and excitation of the acceptor directly will also result in emission from the acceptor. As such, differentiation of the optical signals can be based on observation of an emission signal in combination with identification of the excitation wavelength used to produce the emission. Different light emissions may have other characteristics that do not overlap, such as emission anisotropy or fluorescence lifetime. Also, when the light emissions are filtered, the wavelength ranges of the emission spectra may be narrowed.

The optical components may have fixed positions in the optical assembly or may be selectively moveable. As used herein, when the term "selectively" is used in conjunction with "moving" and similar terms, the phrase means that the position of the optical component may be changed in a desired manner. At least one of the locations and the orientation of the optical component may be changed. For example, in particular embodiments, a rotatable mirror is selectively moved to facilitate focusing an optical imaging system.

Different elements and components described herein may be removably coupled. As used herein, when two or more elements or components are "removably coupled" (or "removably mounted," and other like terms) the elements are readily separable without destroying the coupled components. For instance, elements can be readily separable when the elements may be separated from each other without undue effort, without the use of a tool (i.e. by hand), or without a significant amount of time spent in separating the components. By way of example, in some embodiments, an optical device may be removably mounted to an optical base plate. In addition, flow cells and fluidic devices may be removably mounted to a device holder.

Imaging sessions include a time period in which at least a portion of the sample is imaged. One sample may undergo or be subject to multiple imaging sessions. For example, one sample may be subject to two different imaging sessions in which each imaging session attempts to detect optical signals from one or more different labels. As a specific example, a first scan along at least a portion of a nucleic acid sample may detect labels associated with nucleotides A and C and a second scan along at least a portion of the sample may detect labels associated with nucleotides G and T. In sequencing embodiments, separate sessions can occur in separate cycles of a sequencing protocol. Each cycle can include one or more imaging session. In other embodiments, detecting optical signals in different imaging sessions may include scanning different samples. Different samples may be of the same type (e.g., two microarray chips) or of different types (e.g., a flow cell and a microarray chip).

During an imaging session, optical signals provided by the sample are observed. Various types of imaging may be used with embodiments described herein. For example, embodiments described herein may utilize a "step and shoot" procedure in which regions of a sample area are individually imaged. Embodiments may also be configured to perform at least one of epi-fluorescent imaging and total-internal-reflectance-fluorescence (TIRF) imaging. In other embodiments, the sample imager is a scanning time-delay integration (TDI) system. Furthermore, the imaging sessions may include "line scanning" one or more samples such that a linear focal region of light is scanned across the sample(s). Some methods of line scanning are described, for example, in U.S. Pat. No. 7,329,860 and U.S. Pat. Pub. No. 2009/0272914, each of which the complete subject matter is incorporated herein by reference in their entirety. Imaging sessions may also include moving a point focal region of light in a raster pattern across the sample(s). In alternative embodiments, imaging sessions may include detecting light emissions that are generated, without illumination, and based entirely on emission properties of a label within the sample (e.g., a radioactive or chemiluminescent component in the sample). In alternative embodiments, flow cells may be mounted onto an imager (e.g., CCD or CMOS) that detects the desired reactions.

As used herein, the term "sample" or "sample-of-interest" includes various materials or substances of interest that undergo an imaging session where optical signals from the material or substance are observed. In particular embodiments, a sample may include biological or chemical substances of interests and, optionally, an optical substrate or support structure that supports the biological or chemical substances. As such, a sample may or may not include an optical substrate or support structure. As used herein, the term "biological or chemical substances" may include a variety of biological or chemical substances that are suitable for being imaged or examined with the optical systems described herein. For example, biological or chemical substances include biomolecules, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and biologically active chemical compound(s) such as analogs or mimetics of the aforementioned species. Other chemical substances include labels that can be used for identification, examples of which include fluorescent labels and others set forth in further detail below.

Different types of samples may include different optical substrates or support structures that affect incident light in different manners. In particular embodiments, samples to be detected can be attached to one or more surfaces of a substrate or support structure. For example, flow cells may include one or more flow channels. In flow cells, the flow channels may be separated from the surrounding environment by top and bottom layers of the flow cell. Thus, optical signals to be detected are projected from within the support structure and may transmit through multiple layers of material having different refractive indices. For example, when detecting optical signals from an inner bottom surface of a flow channel and when detecting optical signals from above the flow channel, the optical signals that are desired to be detected may propagate through a fluid having an index of refraction, through one or more layers of the flow cells having different indices of refraction, and through the ambient environment having a different index of refraction.

As used herein, a "fluidic device" is an apparatus that includes one or more flow channels that direct fluid in a predetermined manner to conduct desired reactions. The fluidic device is configured to be fluidically coupled to a fluidic network of an assay system. By way of example, a fluidic device may include flow cells or lab-on-chip devices. Flow cells generally hold a sample along a surface for imaging by an external imaging system. Lab-on-chip devices may hold the sample and perform additional functions, such as detecting the desired reaction using an integrated detector. Fluidic devices may optionally include additional components, such as housings or imagers, that are operatively coupled to the flow channels. In particular embodiments, the channels may have channel surfaces where a sample is located, and the fluidic device can include a transparent material that permits the sample to be imaged after a desired reaction occurs.

In particular embodiments, the fluidic devices have channels with microfluidic dimensions. In such channels, the surface tension and cohesive forces of the liquid flowing therethrough and the adhesive forces between the liquid and the surfaces of the channel have at least a substantial effect on the flow of the liquid. For example, a cross-sectional area (taken perpendicular to a flow direction) of a microfluidic channel may be about 10 $\mu m^2$ or less.

In alternative embodiments, optical imaging systems described herein may be used to scan samples that include microarrays. A microarray may include a population of different probe molecules that are attached to one or more substrates such that the different probe molecules can be differentiated from each other according to relative location.

An array can include different probe molecules, or populations of the probe molecules, that are each located at a different addressable location on a substrate. Alternatively, a microarray can include separate optical substrates, such as beads, each bearing a different probe molecule, or population of the probe molecules, that can be identified according to the locations of the optical substrates on a surface to which the substrates are attached or according to the locations of the substrates in a liquid. Exemplary arrays in which separate substrates are located on a surface include, without limitation, a BeadChip Array available from Illumina®, Inc. (San Diego, Calif.) or others including beads in wells such as those described in U.S. Pat. Nos. 6,266,459, 6,355,431, 6,770,441, 6,859,570, and 7,622,294; and PCT Publication No. WO 00/63437, each of which is hereby incorporated by reference. Other arrays having particles on a surface include those set forth in US 2005/0227252; WO 05/033681; and WO 04/024328, each of which is hereby incorporated by reference.

Any of a variety of microarrays known in the art can be used. A typical microarray contains sites, sometimes referred to as features, each having a population of probes. The population of probes at each site is typically homogenous having a single species of probe, but in some embodiments the populations can each be heterogeneous. Sites or features of an array are typically discrete, being separated. The separate sites can be contiguous or they can have spaces between each other. The size of the probe sites and/or spacing between the sites can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful in the invention can have sites that are separated by less than 100 μm, 50 μm, 10 μm, 5 μm, 1 μm, or 0.5 μm. An apparatus or method of an embodiment of the invention can be used to image an array at a resolution sufficient to distinguish sites at the above densities or density ranges.

Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method according to an embodiment of the invention. An exemplary spotted microarray is a CodeLink™ Array available from Amersham Biosciences. Another microarray that is useful is one that is manufactured using inkjet printing methods such as SurePrint™ Technology available from Agilent Technologies.

The systems and methods set forth herein can be used to detect the presence of a particular target molecule in a sample contacted with the microarray. This can be determined, for example, based on binding of a labeled target analyte to a particular probe of the microarray or due to a target-dependent modification of a particular probe to incorporate, remove, or alter a label at the probe location. Any one of several assays can be used to identify or characterize targets using a microarray as described, for example, in U.S. Patent Application Publication Nos. 2003/0108867; 2003/0108900; 2003/0170684; 2003/0207295; or 2005/0181394, each of which is hereby incorporated by reference.

Furthermore, optical systems described herein may be constructed to include various components and assemblies as described in PCT application PCT/US07/07991, entitled "System and Devices for Sequence by Synthesis Analysis", filed Mar. 30, 2007 and/or to include various components and assemblies as described in International Publication No. WO 2009/042862, entitled "Fluorescence Excitation and Detection System and Method", filed Sep. 26, 2008, both of which the complete subject matter are incorporated herein by reference in their entirety. In particular embodiments, optical systems can include various components and assemblies as described in U.S. Pat. No. 7,329,860 and WO 2009/137435, of which the complete subject matter is incorporated herein by reference in their entirety. Optical systems can also include various components and assemblies as described in U.S. patent application Ser. No. 12/638,770, filed on Dec. 15, 2009, of which the complete subject matter is incorporated herein by reference in its entirety.

In particular embodiments, methods, and optical systems described herein may be used for sequencing nucleic acids. For example, sequencing-by-synthesis (SBS) protocols are particularly applicable. In SBS, a plurality of fluorescently labeled modified nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders. The samples for sequencing can take the form of single nucleic acid molecules that are separated from each other so as to be individually resolvable, amplified populations of nucleic acid molecules in the form of clusters or other features, or beads that are attached to one or more molecules of nucleic acid. Accordingly, sequencing can be carried out on an array such as those set forth previously herein. The nucleic acids can be prepared such that they comprise an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g. A, C, T, G). The nucleotides can include detectable label moieties such as fluorophores. Where the four nucleotides are mixed together, the polymerase is able to select the correct base to incorporate and each sequence is extended by a single base. Noninrporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection steps can be repeated several times to complete a sequencing run. Exemplary sequencing methods are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference.

In some embodiments, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference in its entirety.

Other sequencing techniques that are applicable for use of the methods and systems set forth herein are pyrosequencing, nanopore sequencing, and sequencing by ligation. Exemplary pyrosequencing techniques and samples that are particularly useful are described in U.S. Pat. Nos. 6,210,891; 6,258,568; 6,274,320 and Ronaghi, Genome Research 11:3-11 (2001), each of which is incorporated herein by reference. Exemplary nanopore techniques and samples that are also useful are described in Deamer et al., Acc. Chem. Res. 35:817-825 (2002); Li et al., Nat. Mater. 2:611-615 (2003); Soni et al., Clin Chem. 53:1996-2001 (2007) Healy et al., Nanomed. 2:459-481 (2007) and Cockroft et al., J. am. Chem. Soc. 130:818-820; and U.S. Pat. No. 7,001,792, each of which is incorporated herein by reference. In particular, these methods utilize repeated steps of reagent delivery. An instrument or method set forth herein can be configured with reservoirs, valves, fluidic lines and other fluidic components along with control systems for those components in order to introduce reagents and detect optical signals according to a desired protocol such as those set forth in the references cited above. Any of a variety of samples can be used in these systems such as substrates having beads generated by emulsion PCR, substrates having zero-mode waveguides, substrates having integrated CMOS detectors, substrates having biological nanopores in lipid bilayers, solid-state substrates having synthetic nanopores, and others known in the art. Such samples are described in the context of various sequencing techniques in the references cited above and further in US 2005/0042648; US 2005/0079510; US 2005/0130173; and WO 05/010145, each of which is incorporated herein by reference.

Exemplary labels that can be detected in accordance with various embodiments, for example, when present on or within a support structure include, but are not limited to, a chromophore; luminophore; fluorophore; optically encoded nanoparticles; particles encoded with a diffraction-grating; electrochemiluminescent label such as $Ru(bpy)_3^{2+}$; or moiety that can be detected based on an optical characteristic. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066, each of which is hereby incorporated by reference. In some embodiments, the one pair of labels may be excitable by a first excitation wavelength and another pair of labels may be excitable by a second excitation wavelength.

Although embodiments are exemplified with regard to detection of samples that include biological or chemical substances supported by an optical substrate, it will be understood that other samples can be imaged by the embodiments described herein. Other exemplary samples include, but are not limited to, biological specimens such as cells or tissues, electronic chips such as those used in computer processors, and the like. Examples of some of the applications include microscopy, satellite scanners, high-resolution reprographics, fluorescent image acquisition, analyzing and sequencing of nucleic acids, DNA sequencing, sequencing-by-synthesis, imaging of microarrays, imaging of holographically encoded microparticles and the like.

FIG. 1 is a block diagram of an assay system 100 for biological or chemical analysis formed in accordance with one embodiment. In some embodiments, the assay system 100 is a workstation that may be similar to a bench-top device or desktop computer. For example, at least a majority of the systems and components for conducting the desired reactions can be within a common housing 117 of the assay system 100. In other embodiments, the assay system 100 includes one or more components, assemblies, or systems that are remotely located from the assay system 100 (e.g., a remote database). The assay system 100 may include various components, assemblies, and systems (or sub-systems) that interact with each other to perform one or more predetermined methods or assay protocols for biological or chemical analysis.

For example, the assay system 100 includes a system controller 102 that may communicate with the various components, assemblies, and systems (or sub-systems) of the assay system 100. As shown, the assay system 100 has an optical assembly 104, an excitation source assembly 106, a detector assembly 108, and a fluidic device holder 110 that supports one or more fluidic devices 112 having a sample thereon. The fluidic device may be a flow cell, such as the flow cell 200 described below, or the fluidic device 112 may be the fluidic device 300 described below.

In some embodiments, the optical assembly 104 is configured to direct incident light from the excitation source assembly 106 onto the fluidic device(s) 112. The excitation source assembly 106 may include one or more excitation light sources that are configured to excite labels associated with the sample. The excitation source assembly 106 may also be configured to provide incident light that is reflected and/or refracted by the samples. As shown, the samples may provide optical signals that include light emissions 116 and/or transmission light 118. The device holder 110 and the optical assembly 104 may be moved relative to each other. In some embodiments, the device holder 110 includes a motor assembly 132 that moves the fluidic device 112 with respect to the optical assembly 104. In other embodiments, the optical assembly 104 may be moved in addition to or alternatively to the device holder 110. The optical assembly 104 may also be configured to direct the light emissions 116 and/or transmission light 118 to the detector assembly 108.

The detector assembly 108 may include one or more imaging detectors. The imaging detectors may be, by way of example only, CCD or CMOS cameras, or photomultiplier tubes.

Also shown, the assay system 100 may include a fluidic control system 134 to control the flow of fluid throughout a fluidic network 135 (indicated by the solid lines) of the assay system 100. The fluidic control system 134 may deliver reaction components (e.g., reagents) or other fluids to the fluidic device 112 during, for example, a sequencing protocol. The assay system 100 may also include a fluid storage system 136 that is configured to hold fluids that may be used by the assay system 100 and a temperature control system 138 that regulates the temperature of the fluid. The temperature control system 138 may also generally regulate a temperature of the assay system 100 using, for example, thermal modules, heat sinks, and blowers.

Also shown, the assay system 100 may include a user interface 140 that interacts with the user. For example, the user interface 140 may include a display 142 to display or request information from a user and a user input device 144 to receive user inputs. In some embodiments, the display 142 and the user input device 144 are the same device (e.g., touchscreen). As will be discussed in greater detail below, the assay system 100 may communicate with various components to perform the desired reactions. The assay system 100 may also be configured to analyze the detection data to provide a user with desired information.

The fluidic control system 134 is configured to direct and regulate the flow of one or more fluids through the fluidic network 135. The fluidic control system 134 may include, for example, pumps and valves that are selectively operable for controlling fluid flow. The fluidic network 135 may be in fluid communication with the fluidic device 112 and the fluid storage system 136. For example, select fluids may be drawn from the fluid storage system 136 and directed to the fluidic device 112 in a controlled manner, or the fluids may be drawn from the fluidic device 112 and directed toward, for example, a waste reservoir in the fluid storage system 136. Although not shown, the fluidic control system 134 may also include flow sensors that detect a flow rate or pressure of the fluids within the fluidic network. The sensors may communicate with the system controller 102.

The temperature control system 138 is configured to regulate the temperature of fluids at different regions of the fluidic network 135, the fluid storage system 136, and/or the fluidic device 112. For example, the temperature control system 138 may include a thermocycler 113 that interfaces with the fluidic device 112 and controls the temperature of the fluid that flows along the fluidic device 112. Although not shown, the temperature control system 138 may include sensors to detect the temperature of the fluid or other components. The sensors may communicate with the system controller 102.

The fluid storage system 136 is in fluid communication with the fluidic device 112 and may store various reaction components or reactants that are used to conduct the desired reactions therein. The fluid storage system 136 may store fluids for washing or cleaning the fluidic network 135 or the fluidic device 112 and also for diluting the reactants. For example, the fluid storage system 136 may include various reservoirs to store reagents, enzymes, other biomolecules, buffer solutions, aqueous, and non-polar solutions, and the like. Furthermore, the fluid storage system 136 may also include waste reservoirs for receiving waste products.

The device holder 110 is configured to engage one or more fluidic devices 112, for example, in at least one of a mechanical, electrical, and fluidic manner. The device holder 110 may hold the fluidic device(s) 112 in a desired orientation to facilitate the flow of fluid through the fluidic device 112 and/or imaging of the fluidic device 112.

The system controller 102 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not necessarily intended to limit the definition and/or meaning of the term system controller. In the exemplary embodiment, the system controller 102 executes a set of instructions that are stored in one or more storage elements, memories, or modules in order to at least one of obtain and analyze detection data. Storage elements may be in the form of information sources or physical memory elements within the assay system 100.

The set of instructions may include various commands that instruct the assay system 100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the assay system 100, processed in response to user inputs, or processed in response to a request made by another processing machine (e.g., a remote request through a communication link).

The system controller 102 may be connected to the other components or sub-systems of the assay system 100 via communication links (indicated by dashed lines). The system controller 102 may also be communicatively connected to off-site systems or servers. The communication links may be hardwired or wireless. The system controller 102 may receive user inputs or commands, from the user interface 140. The user input device 144 may include a keyboard, mouse, a touch-screen panel, and/or a voice recognition system, and the like. Alternatively or in addition, the user input device 144 may also be the display 142.

FIG. 1 also illustrates a block diagram of the system controller 102. In one embodiment, the system controller 102 includes one or more processors or modules that can communicate with one another. The system controller 102 is illustrated conceptually as a collection of modules, but may be implemented utilizing any combination of dedicated hardware boards, DSPs, processors, etc. Alternatively, the system controller 102 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

The system controller 102 may include a plurality of modules 151-158 that communicate with a system control module 150. The system control module 150 may communicate with the user interface 140. Although the modules 151-158 are shown as communicating directly with the system control module 150, the modules 151-158 may also communicate directly with each other, the user interface 140, or the other systems. Also, the modules 151-158 may communicate with the system control module 150 through the other modules.

The plurality of modules 151-158 include system modules 151-153 that communicate with the sub-systems. The fluidic control module 151 may communicate with the fluidic control system 134 to control the valves and flow sensors of the fluidic network 135 for controlling the flow of one or more fluids through the fluidic network 135. The fluid storage module 152 may notify the user when fluids are low or when the waste reservoir must be replaced. The fluid storage module 152 may also communicate with the temperature control module 153 so that the fluids may be stored at a desired temperature.

The plurality of modules 151-158 may also include an image analysis module 158 that receives and analyzes the detection data (e.g., image data) from the detector assembly 108. The processed detection data may be stored for subsequent analysis or may be transmitted to the user interface 140 to display desired information to the user. Protocol modules 155-157 communicate with the system control module 150 to control the operation of the sub-systems when conducting predetermined assay protocols. The protocol modules 155-157 may include sets of instructions for instructing the assay system 100 to perform specific operations pursuant to predetermined protocols.

The protocol module 155 may be configured to issue commands for generating a sample within the fluidic device 112. For example, the protocol module 155 may direct the fluid storage system 136 and the temperature control system 138 to generate the sample in a sample area. In one particular embodiment, the protocol module 155 may issue commands to perform bridge PCR where clusters of clonal amplicons are formed on localized areas within a channel (or lane) of a flow cell.

The protocol module 156 may be a sequencing-by-synthesis (SBS) module configured to issue various commands for performing sequencing-by-synthesis processes. In some embodiments, the SBS module 156 may also process detection data. After generating the amplicons through bridge PCR, the SBS module 156 may provide instructions to linearize or denature the amplicons to make sstDNA and to add a sequencing primer such that the sequencing primer may be hybridized to a universal sequence that flanks a region of interest. Each sequencing cycle extends the sstDNA by a single base and is accomplished by modified DNA polymerase and a mixture of four types of nucleotides delivery of which can be instructed by the SBS module 156. The different types of nucleotides have unique fluorescent labels, and each nucleotide has a reversible terminator that allows only a single-base incorporation to occur in each cycle. After a single base is added to the sstDNA, the SBS module 156 may instruct a wash step to remove nonincorporated nucleotides by flowing a wash solution through the flow cell. The SBS module 156 may further instruct the excitation source assembly and detector assembly to perform an image session(s) to detect the fluorescence in each of the four channels (i.e., one for each fluorescent label). After imaging, the SBS module 156 may instruct delivery of a deblocking reagent to chemically cleave the fluorescent label and the terminator from the sstDNA. The SBS module 156 may instruct a wash step to remove the deblocking reagent and products of the deblocking reaction. Another similar sequencing cycle may follow. In such a sequencing protocol, the SBS module 156 may instruct the fluidic control system 134 to direct a flow of reagent and enzyme solutions through the fluidic device 112.

In some embodiments, the SBS module 157 may be configured to issue various commands for performing the steps of a pyrosequencing protocol. Pyrosequencing detects the release of inorganic pyrophosphate (PPi) as particular nucleotides are incorporated into the nascent strand (Ronaghi, M. et al. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res*. 11(1), 3-11; Ronaghi, M. et al. (1998) "A sequencing method based on real-time pyrophosphate." *Science* 281(5375), 363; U.S. Pat. Nos. 6,210,891; 6,258,568 and 6,274,320, the disclosures of which are incorporated herein by reference in their entireties. In pyrosequencing, released PPi can be detected by being immediately converted to adenosine triphosphate (ATP) by ATP sulfurylase, and the level of ATP generated is detected via luciferase-produced photons. In this case, the fluidic device 112 may include millions of wells where each well has a single capture bead having clonally amplified sstDNA thereon. Each well may also include other smaller beads that, for example, may carry immobilized enzymes (e.g., ATP sulfurylase and luciferase) or facilitate holding the capture bead in the well. The SBS module 157 may be configured to issue commands to the fluidic control module 151 to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA, pyrophosphate is released thereby instigating a chain reaction where a burst of light is generated. The burst of light may be detected by a sample detector of the detector assembly. Detection data may be communicated to the system control module 150, the image analysis module 158, and/or the SBS module 157 for processing. The detection data may be stored for later analysis or may be analyzed by the system controller 102 and an image may be sent to the user interface 140.

In some embodiments, the user may provide user inputs through the user interface 140 to select an assay protocol to be run by the assay system 100. In other embodiments, the assay system 100 may automatically detect the type of fluidic device 112 that has been inserted into the device holder 110 and confirm with the user the assay protocol to be run. Alternatively, the assay system 100 may offer a limited number of assay protocols that could be run with the determined type of fluidic device 112. The user may select the desired assay protocol, and the assay system 100 may then perform the selected assay protocol based on preprogrammed instructions.

Figure 2:
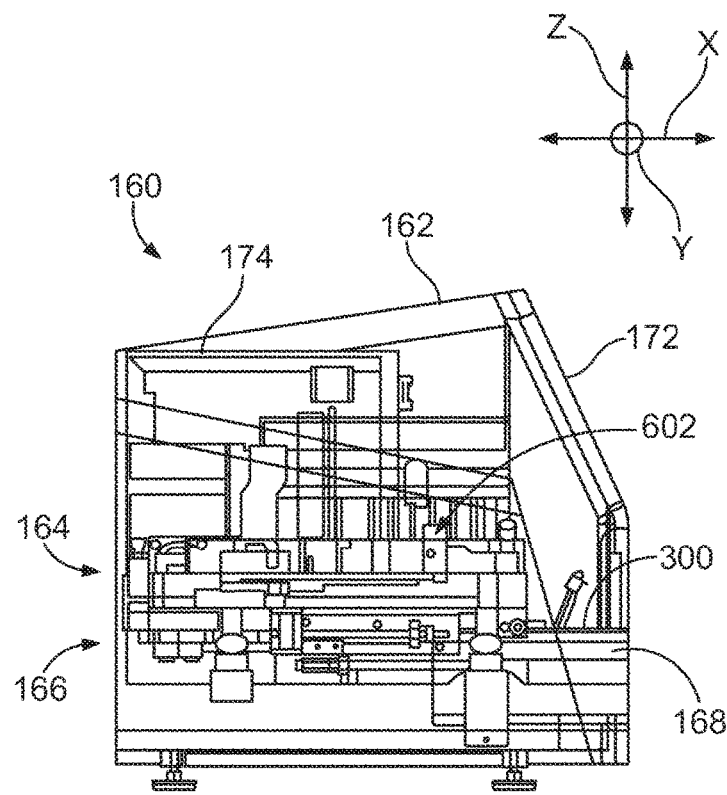
FIG. 2 is a side view of a workstation configured to perform biological or chemical assays in accordance with one embodiment.
Figure 3:
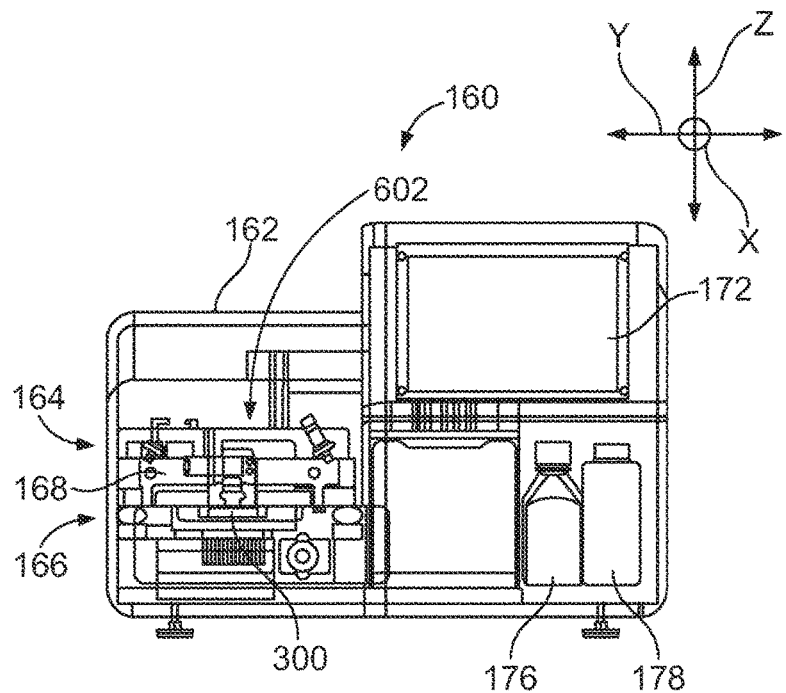
FIG. 3 is a front view of the workstation of FIG. 2.

FIGS. 2 and 3 illustrate a workstation 160 formed in accordance with one embodiment that is configured for biological and chemical analysis of a sample. As shown, the workstation 160 is oriented with respect to mutually perpendicular X, Y, and Z-axes. In the illustrated embodiment, a gravitational force g extends parallel to the Z-axis. The workstation 160 may include a workstation casing 162 (or workstation housing) that is shown in phantom in FIGS. 2 and 3. The casing 162 is configured to hold the various elements of the workstation 160. For example, the workstation 160 may include similar elements as described above with respect to the assay system 100 (FIG. 1). As shown, the workstation 160 has an optical deck 164 having a plurality of optical components mounted thereto. The optical components may be part of an optical assembly, such as the optical assembly 602 described with reference to FIG. 38 et al. The optical deck 164 may have a fixed position with respect to the casing 162.

The workstation 160 may also include a sample deck 166 that is movably coupled to the optical deck 164. The sample deck 166 may have a slidable platform 168 that supports a fluidic device thereon having a sample-of-interest. In the illustrated embodiment, the fluidic device is the fluidic device 300 that is described in greater detail below. The platform 168 is configured to slide with respect to the optical deck 166 and, more specifically, with respect to an imaging lens of the optical assembly 602. To this end, the platform 168 may slide bi-directionally along the X-axis so that the fluidic device 300 may be positioned on the sample deck 166 and so that the imaging lens may slide over the fluidic device 300 to image the sample therein. In other embodiments, the platform 168 may be stationary and the sample deck 166 may slide bi-directionally along the X-axis to position the fluidic device 300 with respect to an imaging lens of the optical assembly 602. Thus, the platform and sample deck can be moveable relative to each other due to movement of the sample deck, platform, or both.

Figure 4:
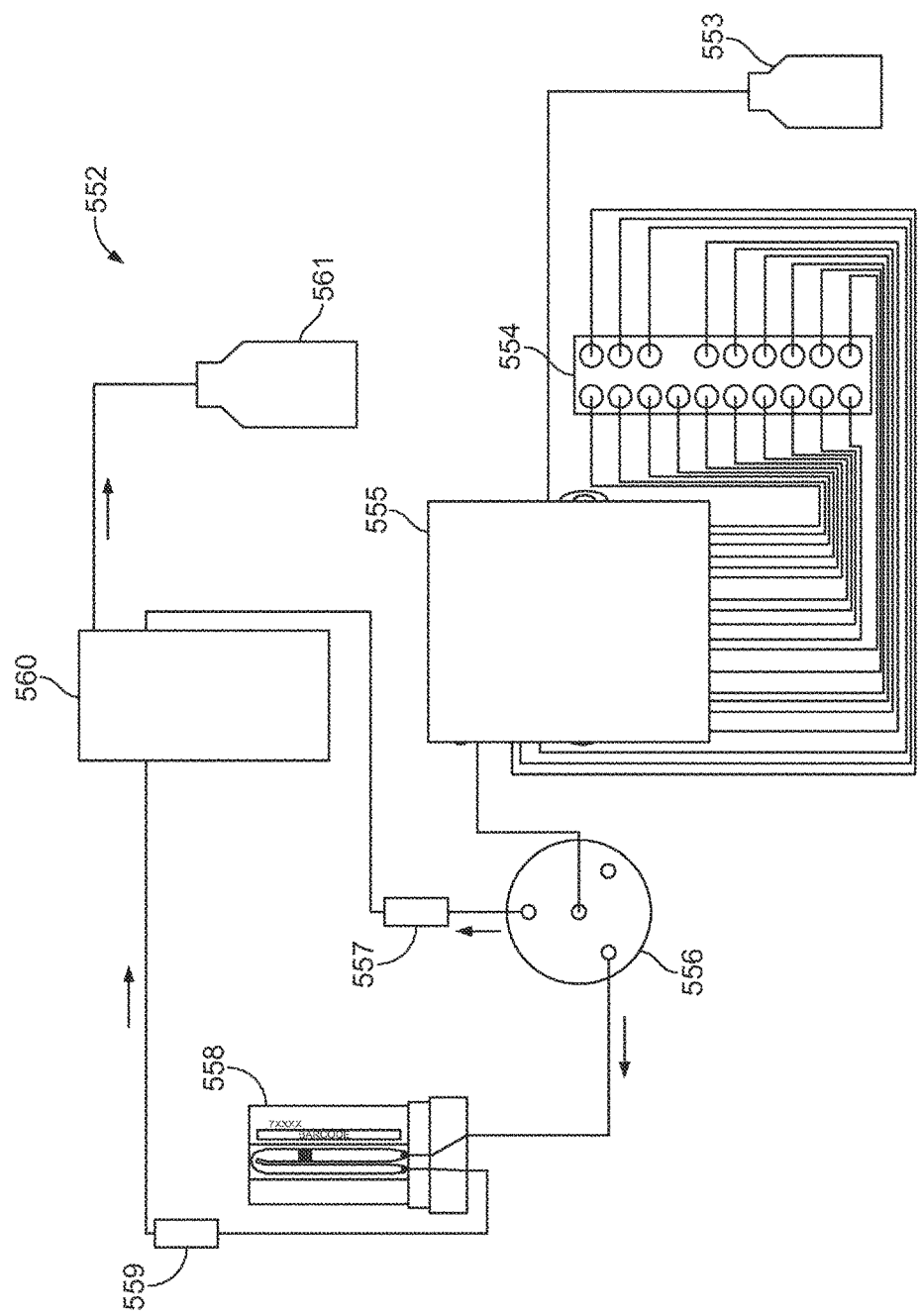
FIG. 4 is a diagram of a fluidic network formed in accordance with one embodiment.

Also shown, the workstation 160 may include a user interface 172, a computing system 174 (FIG. 2), and fluid storage units 176 and 178 (FIG. 4). The user interface 172 may be a touchscreen that is configured to display information to a user and also receive user inputs. For example, the touchscreen may receive commands to perform predetermined assay protocols or receive inquiries from the user. The computing system 174 may include processors and modules, such as the system controller 102 and the modules 151-158 described with reference to FIG. 1. The fluid storage units 176 and 178 may be part of a larger fluid storage system. The fluid storage unit 176 may be for collecting waste that results from performing the assays and the fluid storage unit 178 may include a buffer solution.

FIG. 4 is a diagram of a fluidic network 552 that may be used in the workstation 160 (FIG. 2). As used herein, fluids may be liquids, gels, gases, or a mixture of thereof. Also, a fluid can be a mixture of two or more fluids. The fluidic network 552 may include a plurality of fluidic components (e.g., fluid lines, pumps, flow cells or other fluidic devices, manifolds, reservoirs) configured to have one or more fluids flowing therethrough. As shown, the fluidic network 552 includes a plurality of fluidic components 553-561 interconnected through fluid lines (indicated by the solid lines). In the illustrated embodiment, the fluidic network 552 includes a buffer solution container 553, a reagent tray 554, a multi-port valve 555, a bypass valve 556, a flow rate sensor 557, a flow cell 558, another flow rate sensor 559, a pump 560, and a waste reservoir 561. Fluid flow directions are indicated by arrows along the fluid lines. In addition to the fluidic components 553-561, the fluidic network may also include other fluidic components.

The reagent tray 554 may be similar to the reaction component tray (or reaction component storage unit) 1020 described in greater detail below. The tray 1020 may include various containers (e.g., vials or tubes) containing reaction components for performing assays with embodiments described herein. Operation of the multi-port valve 555 may be controlled by an assay system, such as the assay system 100, to selectively flow different fluids, including mixtures thereof, to the flow cell 558. The flow cell 558 may be the flow cell 200 or the fluidic device 300, which are described in greater detail below, or other suitable fluidic devices.

Figure 5:
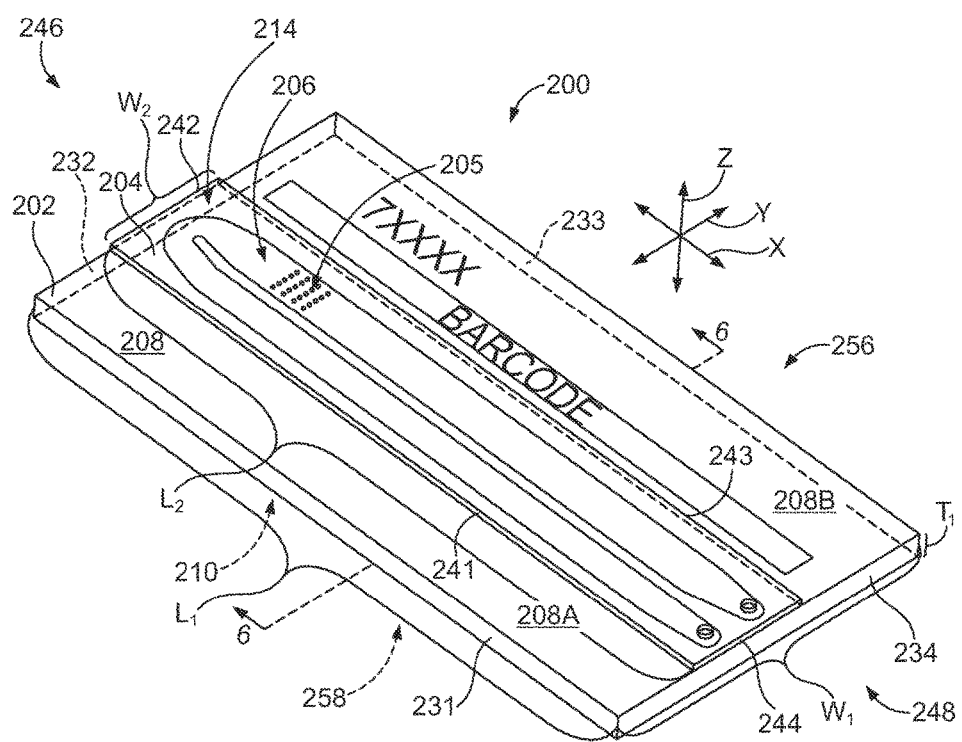
FIG. 5 is a perspective view of a flow cell formed in accordance with one embodiment.

FIGS. 5-60, which are described in greater detail below, illustrate various elements (e.g., components, devices, assemblies, systems, and the like) and methods that may be used with the workstation 160. These elements may cooperate with one another in imaging a sample, analyzing the detection data, and providing information to a user of the workstation 160. However, the following elements and methods may also be used independently, in other apparatuses, or with other apparatuses. For example, the flow cell 200 and the fluidic device 300 may be used in other assay systems. The optical assembly 602 (and elements thereof) may be used for examining other items, such as microcircuits. Furthermore, the device holder 400 may be used to hold other fluidic devices, such as lab-on-chip devices. Assay systems with these devices may or may not be include an optical assembly to detect the desired reactions.

Figure 6:
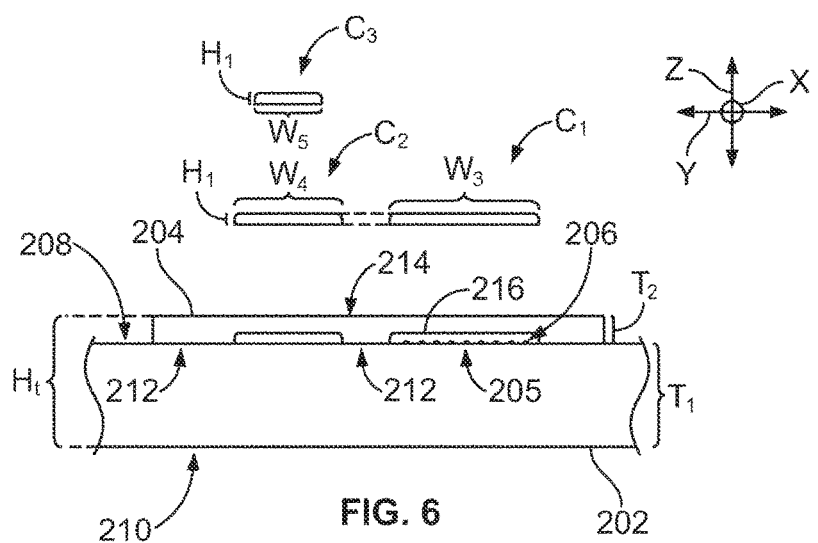
FIG. 6 is a cross-section of the flow cell shown in FIG. 5 taken along the line 6-6 in FIG. 5.
Figure 7:
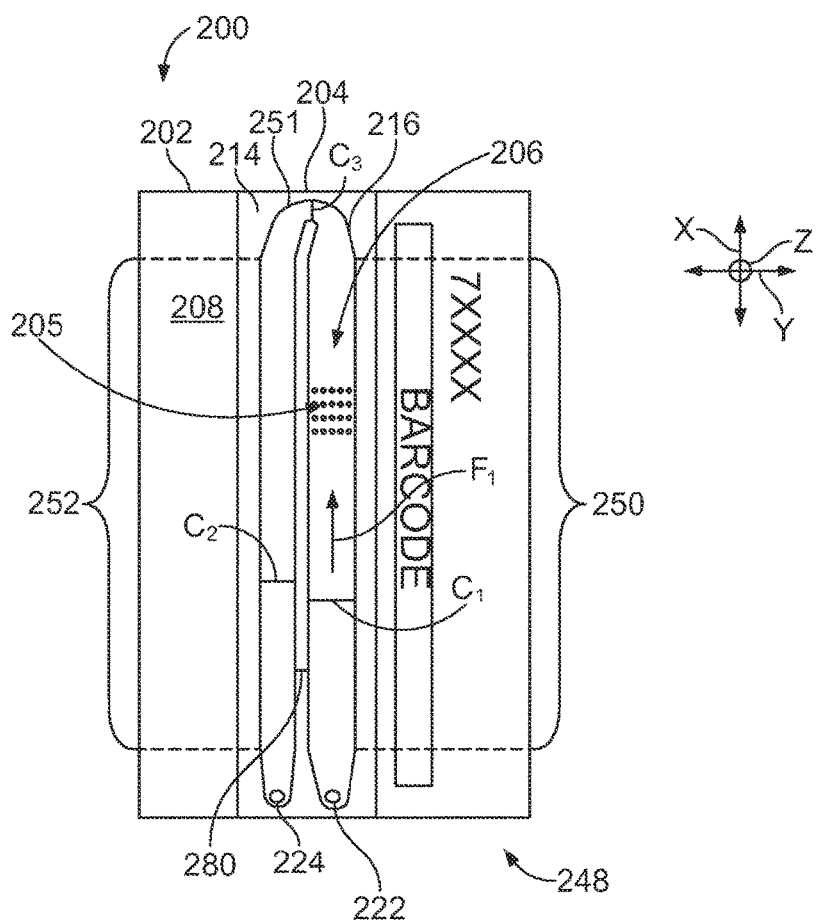
FIG. 7 is a plan view of the flow cell of FIG. 5.

FIGS. 5-7 illustrate a flow cell 200 formed in accordance with one embodiment. As shown in FIGS. 5-7, the flow cell 200 is oriented relative to the X, Y, and Z-axes. The flow cell 200 is configured to hold a sample-of-interest 205 in a flow channel 206. The sample 205 is illustrated as a plurality of DNA clusters that can be imaged during a SBS protocol, but other samples may be used in alternative embodiments. Although only the single U-shaped flow channel 206 is illustrated, alternative embodiments may include flow cells having multiple flow channels with differently shaped paths. The flow cell 200 may be in fluid communication with a fluidic system (not shown) that is configured to deliver reagents to the sample 205 in the flow channel 206. In some embodiments, the sample 205 may provide detectable characteristics (e.g., through fluorescence or chemiluminescence) after desired reactions occur. For instance, the flow cell 200 may have one or more sample areas or regions (i.e., areas or regions where the sample 205 is located) from which optical signals are emitted. In some embodiments, the flow cell 200 may also be used to generate the sample 205 for performing a biological or chemical assay. For example, the flow cell 200 may be used to generate the clusters of DNA before the SBS protocol is performed.

As shown in FIGS. 5-7, the flow cell 200 can include a first layer 202 and a second layer 204 that are secured together and define the flow channel 206 therebetween. The first layer 202 has a mounting surface 208 and an outer or exterior surface 210 (FIGS. 5 and 6). The mounting and outer surfaces 208 and 210 face in opposite directions along the Z-axis and define a thickness $T_1$ (FIGS. 5 and 6) therebetween. The thickness $T_1$ is substantially uniform along an XY-plane, but may vary in alternative embodiments. The second layer 204 has a channel surface 212 (FIG. 6) and an outer or exterior surface 214. The channel and outer surfaces 212 and 214 face in opposite directions along the Z-axis and define a thickness $T_2$ (FIG. 6) therebetween.

Also shown in FIG. 5, the first layer 202 has a dimension or length $L_1$ measured along the X-axis and another dimension or width $W_1$ measured along the Y-axis. In some embodiments, the flow cell 200 may be characterized as a microdevice. Microdevices may be difficult to hold or move by an individual's hands. For example, the length $L_1$ of the flow cell 200 may be about 100 mm, or about 50 mm, or less. In particular embodiments, the length $L_1$ is about 30 mm or less. In some embodiments, the width $W_1$ may be about 35 mm, or about 25 mm or less or, more particularly, the width W1 may be about 15 mm or less. Furthermore, a combined or total height $H_T$ shown in FIG. 7 (e.g., a sum of thicknesses $T_1$ and $T_2$) may be about 10 mm, or about 5 mm or less. More specifically, the height $H_T$ may be about 2 mm or about 1.5 mm or less.

The flow cell 200 includes edges 231-234 that are linear in the illustrated embodiment. Edges 231 and 233 are spaced apart by the width $W_1$ and extend the length $L_1$ of the flow cell 200. Edges 232 and 234 are spaced apart by the length $L_1$ and extend along the width $W_1$. Also shown, the second layer 204 may have a dimension or length $L_2$ measured along the X-axis and another dimension or width $W_2$ measured along the Y-axis. In the illustrated embodiment, the edges 231-234 define a perimeter of the flow cell 200 and extend along a common cell plane that extends parallel to the XY-plane. Also shown, the second layer 204 may have edges 241-244 that are similarly oriented as the edges 231-234 as shown in FIG. 5.

In the illustrated embodiment, the width $W_1$ is substantially greater than the width $W_2$, and the second layer 204 is positioned on only a portion of the mounting surface 208. As such, the mounting surface 208 includes exposed grip portions 208A and 208B on opposite sides of the second layer 204. The width $W_2$ extends between the grip portions 208A and 208B. The flow cell 200 may also have cell sides 256 and 258 that face in opposite directions along the Z-axis. In the illustrated embodiment, the cell side 256 includes the grip portions 208A and 208B and the exterior surface 214, and the cell side 258 includes the exterior surface 210. Also shown, the flow cell 200 may extend lengthwise between opposite first and second cell ends 246 and 248. In the illustrated embodiment, the edges 232 and 242 are substantially flush with respect to each other at the first cell end 246, and the edges 234 and 244 are substantially flush with respect to each other at the opposite second cell end 248.

As shown in FIG. 6, the second layer 204 has at least one grooved portion 216 that extends along the channel surface 212. In the illustrated embodiment, the channel surface 212 is etched to form the grooved portion 216, but the grooved portion 216 may be formed by other processes, such as machining the channel surface 212. To assemble the flow cell 200, the channel surface 212 of the second layer 204 is mounted onto and secured to the mounting surface 208 of the first layer 202. For example, the channel and mounting surfaces 212 and 208 may be bonded together using an adhesive (e.g., light-activated resin) that prevents leakage from the flow cell 200. In other embodiments, the channel and mounting surfaces 212 and 208 may be secured together by other adhesives or mechanically interlocked and/or held together. Thus, the first layer 202 is configured to cover the grooved portion 216 of the second layer 204 to form the flow channel 206. In the illustrated embodiment, the grooved portion 216 may be a single continuous groove that extends substantially the length $L_2$ toward the first end, curves, and then extends substantially the length $L_2$ toward the second end. Thus, the flow channel 206 may be substantially U-shaped.

In FIGS. 5-7 the sample 205 is shown as being located along only the mounting surface 208. However, in other embodiments, the sample 205 may be located on any surface that defines the flow channel 206. For instance, the sample 205 may also be located on the mating surface 212 of the grooved portion 216 that partially defines the flow channel 206.

In the illustrated embodiment, the flow channel 206 may include a plurality of channel segments 250-252. Different channel segments may have different dimensions with respect to the immediately upstream or downstream channel segment. In the illustrated embodiment, the flow channel 206 may include a channel segment 250, which may also be referred to as the imaging segment 250. The channel segment 250 may have a sample area that is configured to be imaged by an imaging system (not shown). The flow channel 206 may also have channel segments 251 and 252, which may also be referred to as non-imaging segments 250 and 252. As shown, the channel segments 250 and 252 extend parallel to each other through the flow cell 200. The channel segments 251 and 252 of the flow channel 206 may be sized and shaped relative to the channel segment 250 to control the flow of fluid and gases that may flow therethrough.

For example, FIG. 7 also illustrates cross-sections $C_1$-$C_3$ of the channel segments 250-252, respectively, that are taken perpendicular to a flow direction $F_1$. In some embodiments, the cross-sections $C_1$-$C_3$ may be differently sized (i.e., different cross-sectional areas) to control the flow of fluid through the flow channel 206. For example, the cross-section $C_1$ is greater in size than the cross-sections $C_2$ and $C_3$. More specifically, the channel segments 250-252 of the flow channel 206 may have a substantially equal height $H_1$ measured between the grooved portion 216 of the channel surface 212 (FIG. 6) and the mounting surface 208. However, the channel segments 250-252 of the flow channel 206 may have different widths $W_3$-$W_5$, respectively. The width $W_3$ is greater than the widths $W_4$ and $W_5$. The channel segment 251 may constitute a curved or elbow segment that fluidicly joins the channel segments 250 and 252. The cross-section $C_3$ is smaller than the cross-sections $C_1$ and $C_2$. For example, the width $W_5$ is less than the widths $W_3$ and $W_4$.

Figure 8:
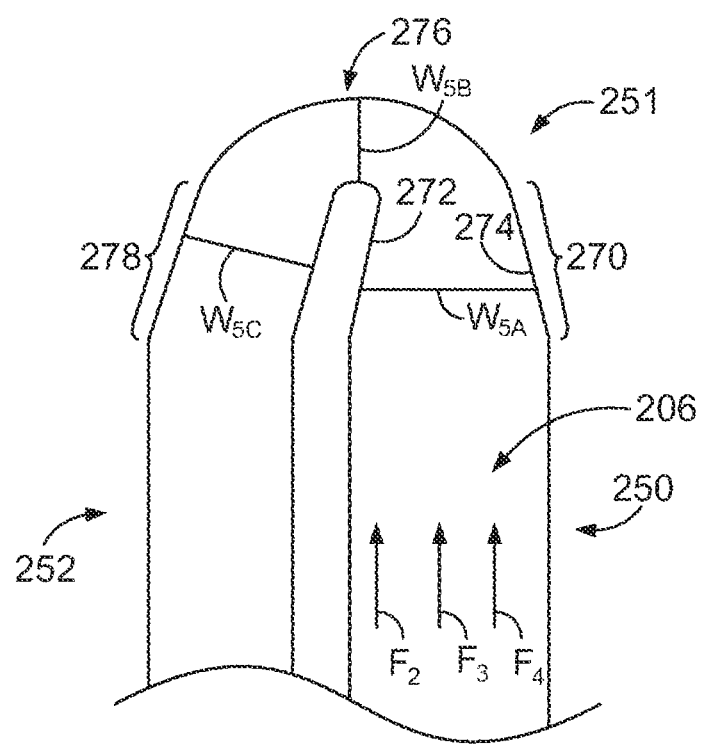
FIG. 8 is an enlarged view of a curved segment of a flow channel.

FIG. 8 is an enlarged view of the curved segment 251 and portions of the channel segments 250 and 252. As described above, the channel segments 250 and 252 may extend parallel to each other. Within the flow channel 206, it may be desirable to have a uniform flow across the sample area. For example, the fluid may include stream portions $F_2$-$F_4$. Dimensions of the channel segments 250-252 may be configured so that the stream portions $F_2$-$F_4$ have substantially equal flow rates across the sample area. In such embodiments, different sections or portions of the sample 205 (FIG. 5) may have a substantially equal amount of time to react with reaction components within the fluid.

To this end, the curved segment 251 of the flow channel 206 may have a non-continuous contour that fluidicly joins the channel segments 250 and 252. For example, as shown in FIG. 8, the curved segment 251 may include a tapering portion 270, an intermediate portion 276, and a downstream portion 278. As shown, the tapering portion 270 has a width $W_{5A}$ that gradually reduces in size. More specifically, the curved segment 251 may include sidewalls 272 and 274 that extend inward toward each other at a substantially equal angle. The intermediate portion 276 curves from the tapering portion 270 to the downstream portion 278. The intermediate portion 276 has a width $W_{5B}$ that reduces in size and then begins to increase in size. The downstream portion 278 has a substantially uniform width $W_{5C}$ throughout and extends along a substantially linear path from the intermediate portion 276 to the channel segment 252. In other words, the sidewalls 272 and 274 may extend parallel to each other throughout the downstream portion 278.

Returning to FIG. 7, the flow cell 200 includes inlet and outlet ports 222 and 224, respectively. The inlet and outlet ports 222 and 224 are formed only through the second layer 204. However, in alternative embodiments, the inlet and outlet ports 222 and 224 may be formed through only the first layer 202 or through both layers 202 and 204. The flow channel 206 is in fluid communication with and extends between the inlet and outlet ports 222 and 224. In particular embodiments, the inlet and outlet ports 222 and 224 are located proximate to each other at the cell end 248 of the flow cell 200 (or proximate to the edges 234 and 244). For example, a spacing 282 that separates the inlet and outlet ports 222 and 224 may be approximately equal to the width $W_3$. More specifically, the spacing 282 may be about 3 mm, about 2 mm, or less. Furthermore, the channel segments 250 and 252 may be separated by a spacing 280. The spacing 280 may be less than the width $W_3$ of the channel segment 250 or, more particularly, less than the width $W_4$ of the channel segment 252. Thus, a path of the flow channel 206 may be substantially U-shaped and, in the illustrated embodiment, have a non-continuous contour along the curved segment 251.

In alternative embodiments, the flow channel 206 may have various paths such that the inlet and outlet ports 222 and 224 have different locations in the flow cell 200. For example, the flow channel may form a single lane that extends from the inlet port at one end of the flow cell to the outlet port at the opposite end of the flow cell.

With respect to FIG. 6, in some embodiments, the thickness $T_2$ (FIG. 6) of the second layer 204 is substantially uniform along the imaging portion 250. The uniform thickness $T_2$ along the imaging portion 250 may be configured to transmit optical signals therethrough. Furthermore, the thickness $T_1$ of the first layer 202 is substantially uniform along the imaging portion 250 and configured to permit uniform transfer of thermal energy therethrough into the flow channel 206.

FIGS. 9-11 illustrate a fluidic device 300 formed in accordance with one embodiment. For illustrative purposes, the fluidic device 300 is oriented with respect to the mutually perpendicular X, Y, and Z-axes shown in FIGS. 9 and 10. FIGS. 9 and 10 are perspective views of the fluidic device 300. As shown in FIGS. 9 and 10, the fluidic device 300 includes a cartridge (or flow cell carrier) 302 and the flow cell 200. The cartridge 302 is configured to hold the flow cell 200 and facilitate orienting the flow cell 200 for an imaging session.

In some embodiments, the fluidic device 300 and the cartridge 302 may be removable such that the cartridge 302 may be removed from an imaging system (not shown) by an individual or machine without damage to the fluidic device 300 or cartridge 302. For example, the cartridge 302 may be configured to be repeatedly inserted and removed into the imaging system without damaging the cartridge 302 or rendering the cartridge 302 unsuitable for its intended purpose. In some embodiments, the fluidic device 300 and the cartridge 302 may be sized and shaped to be handheld by an individual. Furthermore, the fluidic device 300 and the cartridge 302 may be sized and shaped to be carried by an automated system.

As shown in FIGS. 9 and 10, the cartridge 302 may include a housing or carrier frame 304 and a cover member 306 that is coupled to the housing 304. The housing 304 has housing or carrier sides 303 and 305 that face in opposite directions along the Z-axis and have a height $H_2$ (shown in FIG. 11) extending therebetween. As shown in FIG. 9, the housing 304 includes a bridge member 324 at a loading end 316 of the fluidic device 300 and a base member 326 at an opposite receiving end 318 of the fluidic device 300. The housing 304 also includes a pair of spaced apart leg extensions 328 and 330 that extend between the bridge and base members 324 and 326. The bridge member 324 extends between and joins the leg extensions 328 and 330. The bridge member 324 may include a recess 321 (shown in FIG. 10) that opens to an exterior of the fluidic device 300. As shown in FIG. 9, the leg extensions 328 and 330 may have a plurality of grip members 371-374 that are configured to grip the cell side 256 of the flow cell 200.

Also shown in FIG. 9, the fluidic device 300 may have a device window 315 that passes entirely through the cartridge 302 along the Z-axis. In the illustrated embodiment, the device window 315 is substantially framed by the bridge member 324, the cover member 306, and the leg extensions 328 and 330. The device window 315 includes a reception space 308 and a plurality of recesses 320 and 322 that are immediately adjacent to the reception space 308. The reception space 308 is configured to receive the flow cell 200. When the flow cell 200 is positioned within the reception space 308, the flow cell 200 is exposed to an exterior of the fluidic device 300 such that the flow cell 200 may be viewed or directly engaged along the housing side 303 and also the housing side 305. For example, the cell side 258 (also shown in FIG. 11) that faces in an opposite direction along the Z-axis relative to the cell side 256. The cell side 256 may be viewed by the imaging system or directly engaged by another component along the housing side 303. Likewise, the cell side 258 may be viewed by the imaging system or directly engaged by another component along the housing side 305.

With respect to FIGS. 9 and 10, the cover member 306 may include a cover body 340 and a gasket 342 that are coupled to each other. The gasket 342 includes inlet and outlet passages 346 and 344 (shown in FIG. 9) that are located proximate to one another. In the illustrated embodiment, the cover body 340 and the gasket 342 are co-molded into a unitary structure. When formed, the cover body 340 and the gasket 342 may have different compressible properties. For example, in particular embodiments, the gasket 342 may comprise a material that is more compressible than material of the cover body 340. However, in alternative embodiments, the cover body 340 and the gasket 342 may be separate parts that are coupled together (e.g., mechanically or using an adhesive). In other embodiments, the cover body 340 and the gasket 342 may be different portions or regions of a single continuous structure.

The cover member 306 may be movably coupled to the housing 304. For example, the cover member 306 may be rotatably coupled to the base member 326 of the housing 304. In such embodiments, the gasket 342 is rotatable about an axis of rotation $R_1$ between a mounted position (shown in FIG. 9) and a disengaged position (shown in FIG. 10). In other embodiments in which the cover member 306 is movably coupled to the housing 304, the cover member 306 may be detachable from the housing 304. For example, when attached to the housing 304, the detachable cover member may be in a mounted position that is similar to the mounted position as shown in FIG. 9. When unattached to the housing 304, the detachable cover member may be completely removed in a disengaged position.

Also shown in FIG. 10, the housing 304 may define a cartridge cavity 338 (FIG. 10) that is accessible when the cover member 306 is in the disengaged position. In some embodiments, an identification transmitter 336 may be positioned within the cartridge cavity 338. The identification transmitter 336 is configured to communicate information about the flow cell 200 to a reader. For example, the identification transmitter 336 may be an RFID tag. The information provided by the identification transmitter 336 may, for example, identify the sample in the flow cell 200, a lot number of the flow cell or sample, a date of manufacture, and/or the assay protocol to be performed when the flow cell 200 is inserted into the imaging system. The identification transmitter 336 may communicate other information as well.

FIG. 11 is a cross-section of the fluidic device 300 viewed along the Y-axis. In some embodiments, the reception space 308 is sized and shaped relative to the flow cell 200 so that the flow cell 200 is retained in the space, but in at least some configurations may float therein. As used herein, the term "float" and like terms includes the component being permitted to move a limited distance in at least one direction (e.g., along the X, Y, or Z-axes). For example, the flow cell 200 may be capable of shifting within the reception space 308 along the XY-plane. The flow cell 200 may also be capable of moving in a direction along the Z-axis within the reception space 308. Furthermore, the flow cell 200 can also be capable of slightly rotating within the reception space 308. In particular embodiments, the housing 304 permits the flow cell 200 to shift, move, and slightly rotate within the reception space 308 with respect to any of the X, Y, and Z-axes.

In some embodiments, the reception space 308 may also be characterized as the space that the fluidic device 300 allows the flow cell 200 to move freely within when the fluidic device 300 is holding the flow cell 200. Thus, dimensions of the reception space 308 may be based upon positions of reference surfaces of the fluidic device 300 that can directly engage the flow cell 200. The reference surfaces may be surfaces of the housing 304 or the cover member 306, including the gasket 342. For example, FIG. 11 illustrates a plurality of reference surfaces 381-387. The references surfaces 381 and 382 of the grip members 371 and 372, respectively, and the reference surface 383 of the gasket 342 may limit movement of the flow cell 200 beyond a predetermined level when the flow cell 200 is held within the reception space 308. The reference surface 384 of the gasket 342 and the reference surface 385 of the bridge member 324 may limit movement of the flow cell 200 along the XY-plane. Furthermore, the reference surfaces 386 and 387 of the bridge member 324 and the cover member 306, respectively, may also limit movement of the flow cell 200 along the Z-axis. However, the references surfaces 381-387 are exemplary only and the fluidic device 300 may have other reference surfaces that limit movement of the flow cell 200.

To assemble the fluidic device 300, the flow cell 200 may be loaded into the reception space 308. For example, the flow cell 200 may be advanced toward the device window 315 along the housing side 305. The edge 234 (FIG. 5) may be advanced between the grip members 372 and 373 and the gasket 342. The cell side 256 may then be rotated toward the grip members 371-374 so that the grip members 371-374 interface the cell side 256. The edge 232 (FIG. 5) may then be moved toward the bridge member 324 and, more specifically, the reference surface 385 of the bridge member 324. In some embodiments, the bridge member 324 may be deflected or bent to provide more space for positioning the cell end 246 (FIG. 5) thereon. When the flow cell 200 is loaded into the cartridge 302, the housing 304 and the cover member 306 may effectively grip the perimeter of the flow cell 200 such that the flow cell 200 is confined to move only within the reception space 308.

In alternative embodiments, the cell end 246 may be first inserted positioned by the bridge member 324 and then the gasket 342. In other embodiments, the flow cell 200 may approach the housing side 303. The grip members 371-374 may have tapered or beveled surfaces that permit the flow cell 200 to be snapped into position within the reception space 308.

Before, after, or during the loading of the flow cell 200, the cover member 306 may be moved to the disengaged position so that the identification transmitter 336 (FIG. 10) may be positioned with the cartridge cavity 338 (FIG. 10). When the gasket 342 is in the mounted position, the inlet and outlet passages 346 and 344 may have a predetermined location and orientation with respect to the housing 304 and the reception space 308. The gasket 342 may be mounted over the flow cell 200 along an exposed portion of the flow cell 200 (i.e., the cell side 256). The inlet and outlet passages 346 and 344 may be generally aligned with the inlet and outlet ports 224 and 222 (FIG. 5).

However, it should be noted that the illustrated fluidic device 300 is only one particular embodiment, and the fluidic device 300 may have different configurations in alternative embodiments. For example, in alternative embodiments, the flow cell 200 may not be exposed to the exterior of the fluidic device 300 along each of the housing sides 303 and 305. Instead, the flow cell 200 may be exposed to the exterior along only one of the housing sides (e.g., the housing side 303). Furthermore, in alternative embodiments, the cover member 306 may not be rotatably coupled to the housing 304. For example, the cover member 306 may be entirely detachable.

FIGS. 12-15 illustrate fluidic devices 900 and 920 formed in accordance with alternative embodiments that may also be used in assay systems, such as the assay system 100 (FIG. 1) and the workstation 160 (FIG. 2). The fluidic devices 900 and 920 may include similar features as the fluidic device 300. For example, as shown, in FIGS. 12 and 13, the fluidic device 900 may include a cartridge (or flow cell carrier) 902 and the flow cell 200. The cartridge 902 is configured to hold the flow cell 200 and facilitate orienting the flow cell 200 for an imaging session. The cartridge 902 includes a housing 904 and a cover member 906 that is movably mounted to the housing 904. The cover member 906 is in the mounted position in FIG. 12 and the disengaged position in FIG. 13.

Figure 12:
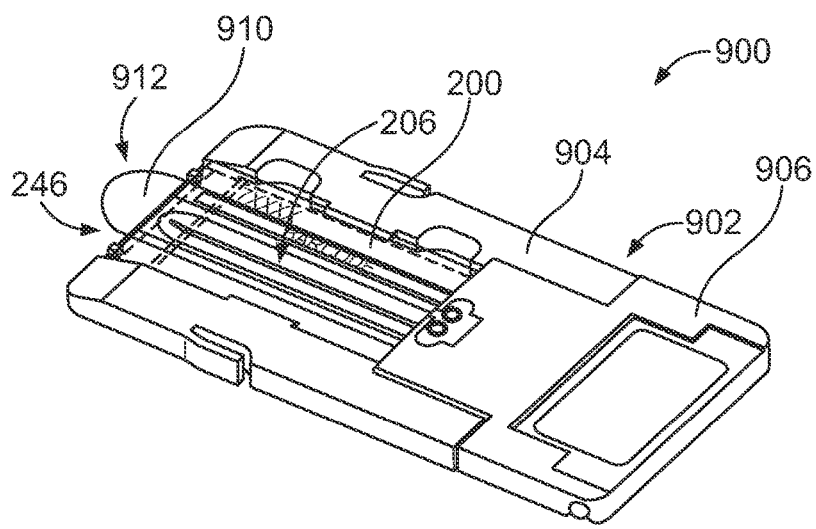
FIG. 12 is a perspective view of a fluidic device formed in accordance with another embodiment.
Figure 13:
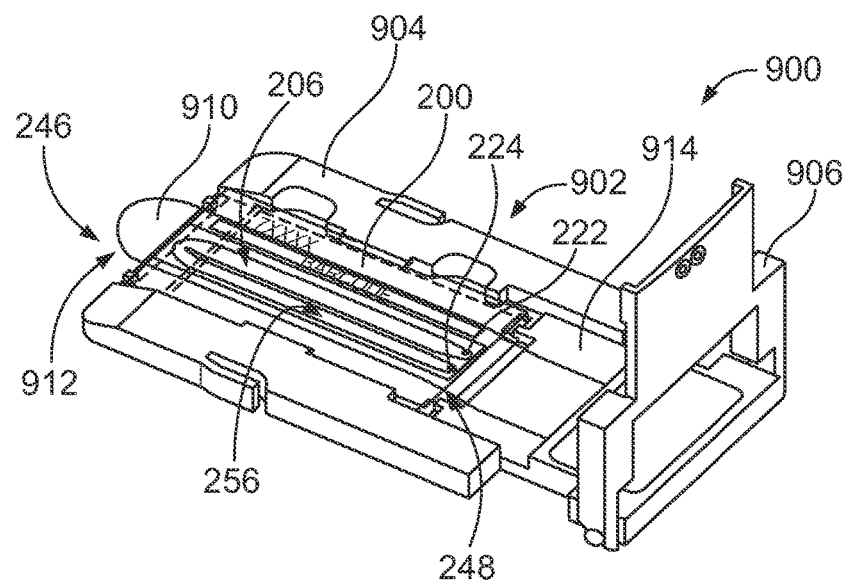
FIG. 13 is a perspective view of the fluidic device of FIG. 12.

Also shown in FIGS. 12 and 13, the fluidic device 900 may include a sealing member 910 that covers the inlet and outlet ports 222 and 224 (FIG. 13) of the flow cell 200. In some embodiments, the sealing member 910 is configured to facilitate retaining fluid within the flow channel 206 so that the sample 205 (FIG. 5) within the flow channel 206 remains in a fluid environment. However, in some embodiments, the sealing member 910 may be configured to prevent unwanted materials from entering the flow channel 206. As shown in FIGS. 12 and 13, the sealing member 910 is a single piece of tape that extends between the cell ends 246 and 248 (FIG. 13). An overhang portion 912 may extend away from the cell end 246. In alternative embodiments, the sealing member 910 may be more than one piece of tape (e.g., one piece of tape for each of the inlet and outlet ports 222 and 224) or the sealing member 910 may be other elements capable of covering the inlet and outlet ports 222 and 224. For example, the sealing member 910 could include plugs.

In some embodiments, the sealing member 910 covers the inlet and outlet ports 222 and 224 when the fluidic device 900 is not mounted to an assay system. For example, the sealing member 910 may be used when the fluidic device 900 is being stored or transported, or when a sample is being grown or generated within the flow cell 200. In such instances, the sealing member 910 may be secured to the flow cell 200 and the housing 904 as shown in FIG. 13. More specifically, the sealing member 910 may couple to and extend along the cell side 256 and cover the inlet and outlet ports 222 and 224. The sealing member 910 may also couple to a base member 914 of the housing 904. The cover member 906 may then be moved to the mounted position as shown in FIG. 12 such that the sealing member 910 is sandwiched between the inlet and outlet ports 222 and 224 and the cover member 906. The cover member 906 may facilitate preventing the sealing member 910 from being inadvertently removed. In alternative embodiments, the sealing member 910 may cover inlet and outlet passages 916 and 918 of the cover member 906.

Figure 14:
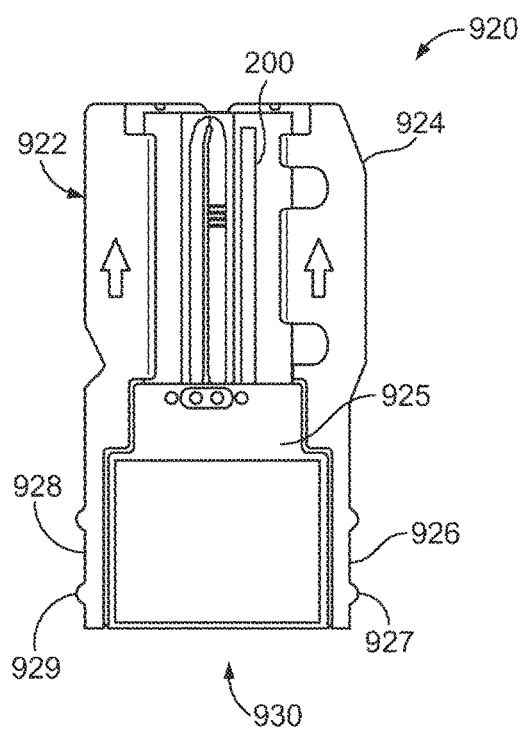
FIG. 14 is a plan view of a fluidic device formed in accordance with one embodiment.
Figure 15:
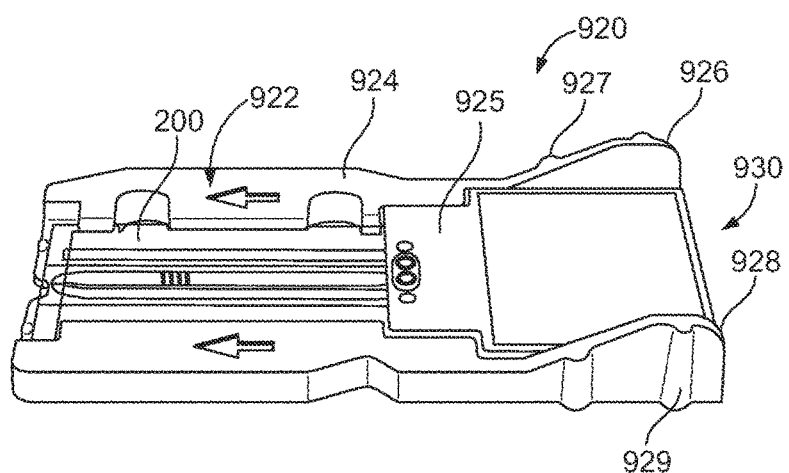
FIG. 15 is a side perspective view of the fluidic device of FIG. 14.

FIGS. 14 and 15 illustrate the fluidic device 920, which may also have similar features as the fluidic devices 300 and 900. As shown, the fluidic device 920 includes a cartridge (or flow cell carrier) 922 and the flow cell 200. The cartridge 922 includes a housing 924 and a cover member 925 that is movably mounted to the housing 924. The cover member 925 is only shown in the mounted position in FIGS. 14 and 15. The housing 924 and the cover member 925 may be similar to the housings 204 and 904 and the cover member 306 and 906 described above.

However, the housing 924 may also include fin projections 926 and 928. The fin projections 926 and 928 are sized and shaped to be gripped by an individual or robotic device, such as when the fluidic device 920 is being inserted in or removed from a device holder (not shown). In some embodiments, the fin projections 926 and 928 may prevent the cover assembly (not shown) from moving to the closed position if the fluidic device 920 is not properly positioned. The fin projections 926 and 928 may include tactile features 927 and 929 that are configured to be gripped by the individual. In the illustrated embodiment, the fin projections 926 and 928 are located at a receiving end 930 of the fluidic device 920. The cover member 925 may extend between the fin projections 926 and 928. However, the fin projections 926 and 928 may have other locations along the cartridge 902.

Figure 16:
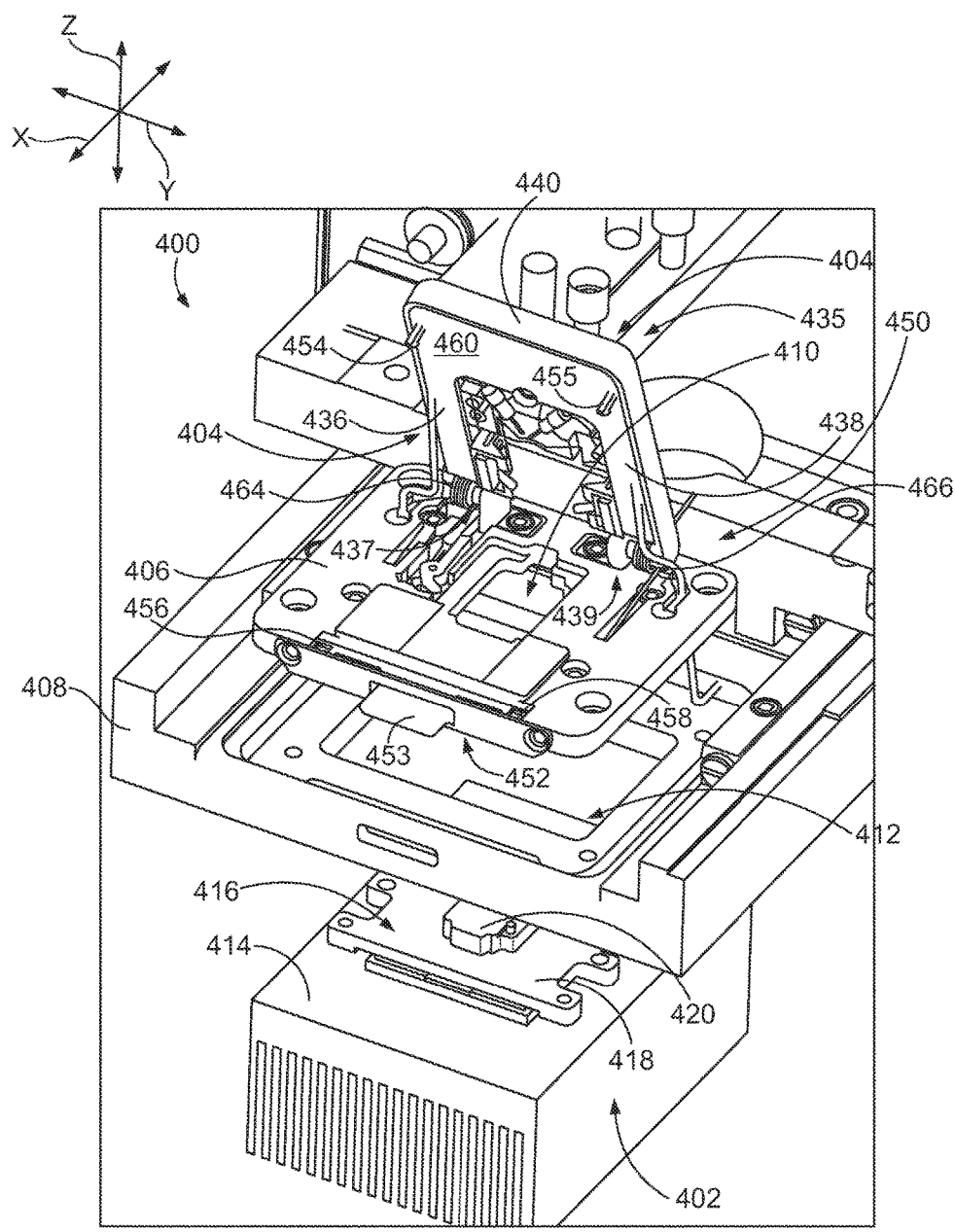
FIG. 16 is a partially exploded view of a device holder formed in accordance with one embodiment.

FIGS. 16-24 show various features of a fluidic device holder 400 formed in accordance with one embodiment. FIG. 16 is a partially exploded view of the holder 400. When assembled, the holder 400 may be used to hold the fluidic device 300 (FIG. 9) and the flow cell 200 (FIG. 5) in a desired orientation during an imaging session. Furthermore, the holder 400 may provide an interface between the fluidic device 300 and the imaging system (not shown) in which the holder 400 may be configured to direct fluids through the flow cell 200 and provide or remove thermal energy from the flow cell 200. Although the holder 400 is shown as holding the fluidic device 300, the holder 400 may be configured to hold other fluidic devices, such as lab-on-chip devices or flow cells without cartridges.

As shown in FIG. 16, the holder 400 may include a removable cover assembly 404 and a support structure 402. In some embodiments, the holder 400 may also include a plate structure 406 and a movable platform 408. The plate structure 406 is operatively coupled to the cover assembly 404 and includes an opening 410 therethrough. Likewise, the platform 408 includes an opening 412 therethrough. The support structure 402 may include a heat sink 414 and a thermal module (or thermocycler) 416 that is mounted onto the heat sink 414. The thermal module 416 includes a base portion 418 and a pedestal 420. When the holder 400 is assembled, the support structure 402, the platform 408, and the plate structure 406 are stacked with respect to each other. As such, the opening 412 is sized and shaped to receive the base portion 418, and the opening 410 is sized and shaped to receive the pedestal 420. When assembled, the cover assembly 404 may be operatively coupled to the plate structure 406 and the support structure 402.

Figure 17:
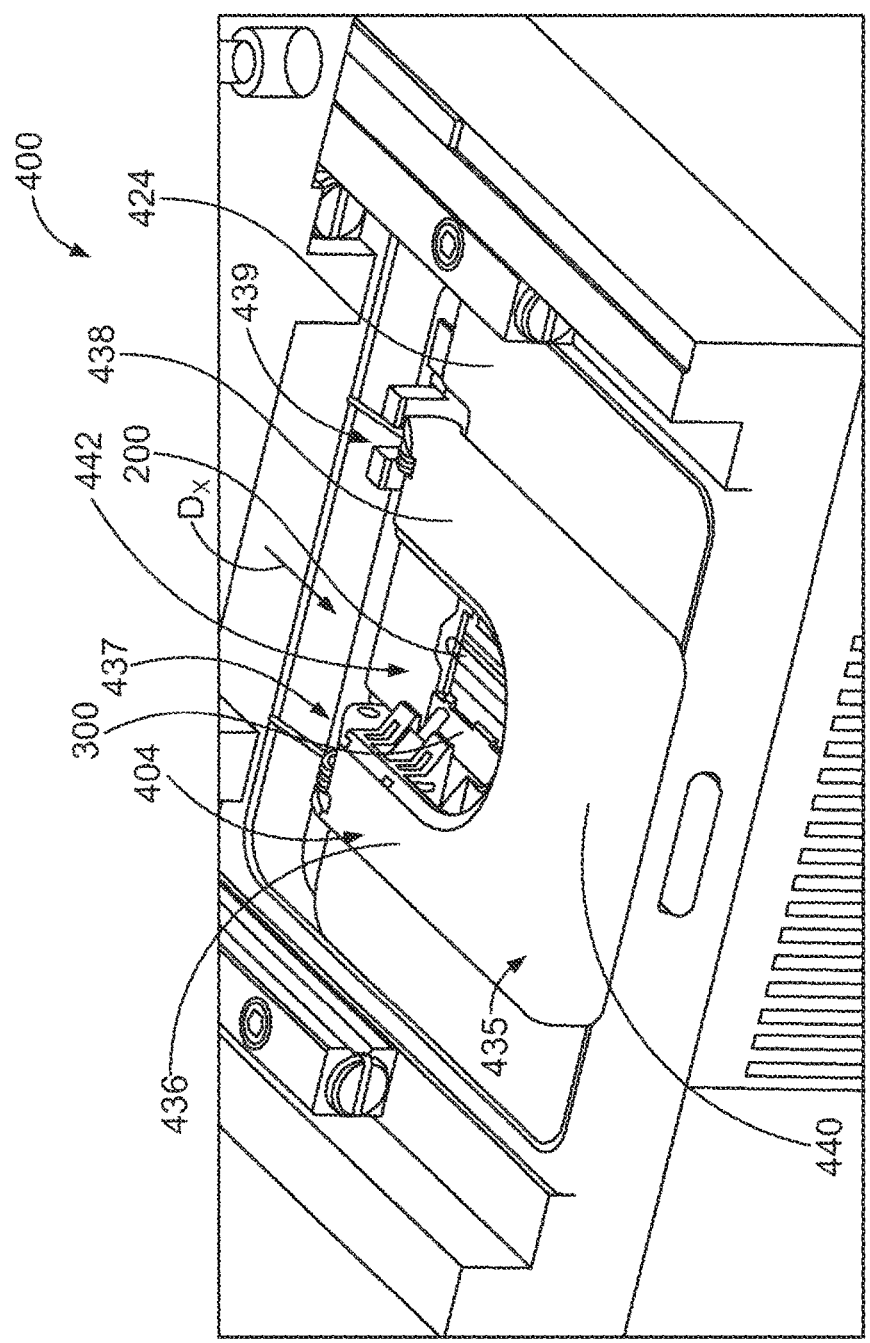
FIG. 17 is a perspective view of the assembled holder of FIG. 16.

FIG. 17 shows the assembled holder 400. In the illustrated embodiment, a panel 424 is positioned over the plate structure 406 (FIG. 16). As shown in FIGS. 16 and 17, the cover assembly 404 includes a cover housing 435 that is coupled to the plate structure 406. The cover housing 435 may be substantially U-shaped having a pair of spaced apart housing legs 436 and 438 that extend in a common direction. The housing legs 436 and 438 may be rotatably coupled to the plate structure 406 at joints 437 and 439. The cover housing 435 may also include a bridge portion 440 that extends between and joins the housing legs 436 and 438. In this manner, the cover assembly 404 may be configured to provide a viewing space 442 (FIG. 17). The viewing space 442 may be sized and shaped to permit an imaging lens (not shown) to move in a direction $D_X$ (FIG. 17) along and over the flow cell 200.

In the illustrated embodiment, the cover assembly 404 is movable relative to the plate structure 406 or support structure 402 between an open position (shown in FIG. 16) and a closed position (shown in FIG. 17). In the open position, the cover assembly 404 is withdrawn or retracted to permit access to a loading region 422 (shown in FIG. 18) of the holder 400 so that the fluidic device 300 may be removed from or inserted into the loading region 422. In the closed position, the cover assembly 404 is mounted over the fluidic device 300. In particular embodiments, the cover assembly 404 establishes a fluid connection with the fluidic device 300 in the closed position and presses the flow cell 200 against the support structure 402.

As shown in FIG. 16, in some embodiments, the holder 400 includes a coupling mechanism 450 to facilitate holding the cover assembly 404 in the closed position. For example, the coupling mechanism 450 may include an operator-controlled element 452 that includes a button 453 that is coupled to a pair of latch openings 456 and 458. The coupling mechanism 450 also includes a pair of latch ends 454 and 455 that project away from a mating face 460 of the cover housing 435. The cover housing 435 may be biased into the open position by spring elements 464 and 466. When the cover assembly 404 is moved into the closed position by an individual or machine, the latch ends 454 and 455 are inserted into the latch openings 456 and 458, respectively, and grip the operator-controlled element 452. To move the cover assembly 404 into the open position, the individual or machine may actuate the button 453 by, for example, pushing the button 453 inward. Since the cover housing 435 is biased by the spring elements 464 and 466, the cover housing 435 is rotated away from the panel 424 (FIG. 17) about the joints 437 and 439.

In alternative embodiments, the coupling mechanism 450 may include other elements to facilitate holding the cover assembly 404 in the closed position. For example, the latch ends 454 and 455 may be replaced by magnetic elements or elements that form an interference fit with openings.

Figure 18:
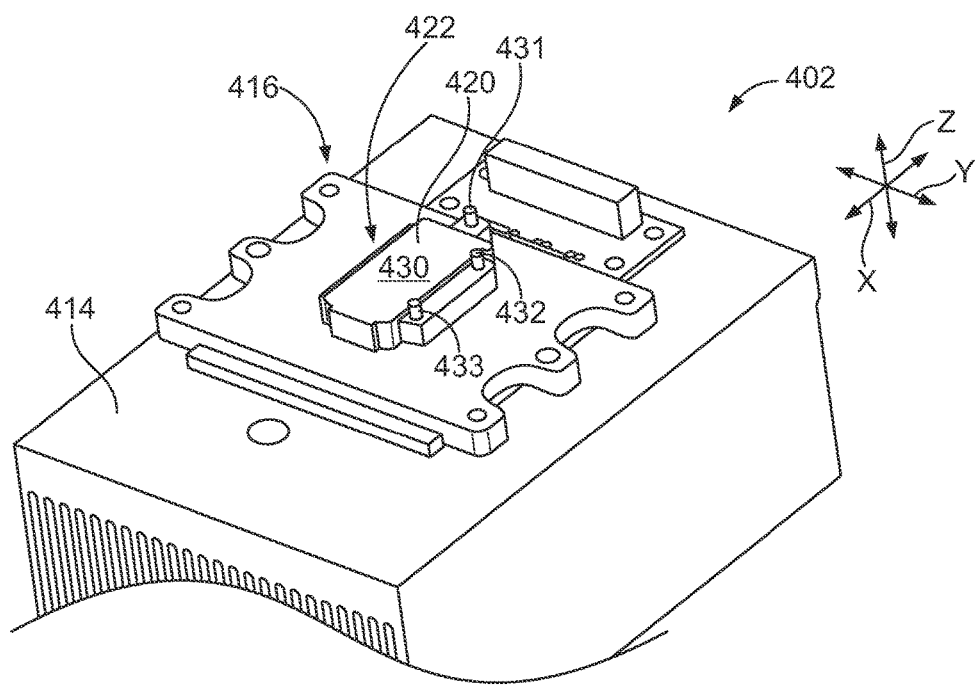
FIG. 18 is a perspective view of a support structure that may be used in the holder of FIG. 16.

FIG. 18 is an isolated perspective view of thermal module 416 and the heat sink 414 of the support structure 402. The thermal module 416 may be configured to control a temperature of the flow cell 200 for predetermined periods of time. For example, the thermal module 416 may be configured to raise the temperature of the flow cell 200 so that DNA in the sample may denature. Furthermore, the thermal module 416 may be configured to remove thermal energy thereby lowering the temperature of the flow cell 200. As shown, the pedestal 420 includes a base surface 430 that is sized and shaped to interface with the flow cell 200 (FIG. 5).

The base surface 430 faces in a direction along the Z-axis. The pedestal 420 may also include a plurality of alignment members 431-433 that are positioned around the base surface 430. In the illustrated embodiment, the alignment members 431-433 have fixed positions with respect to the base surface 430. The alignment members 431-433 have corresponding reference surfaces that are configured to engage the flow cell 200 and facilitate positioning the flow cell 200 for imaging. For example, the reference surfaces of the alignment members 431-433 may face in respective directions along the XY-plane and, as such, may be configured to limit movement of the flow cell 200 along the XY-plane. The support structure 402 may include at least a portion of the loading region 422. The loading region 422 may be partially defined by the base surface 430 and the reference surfaces of the alignment members 431-433.

Figure 19:
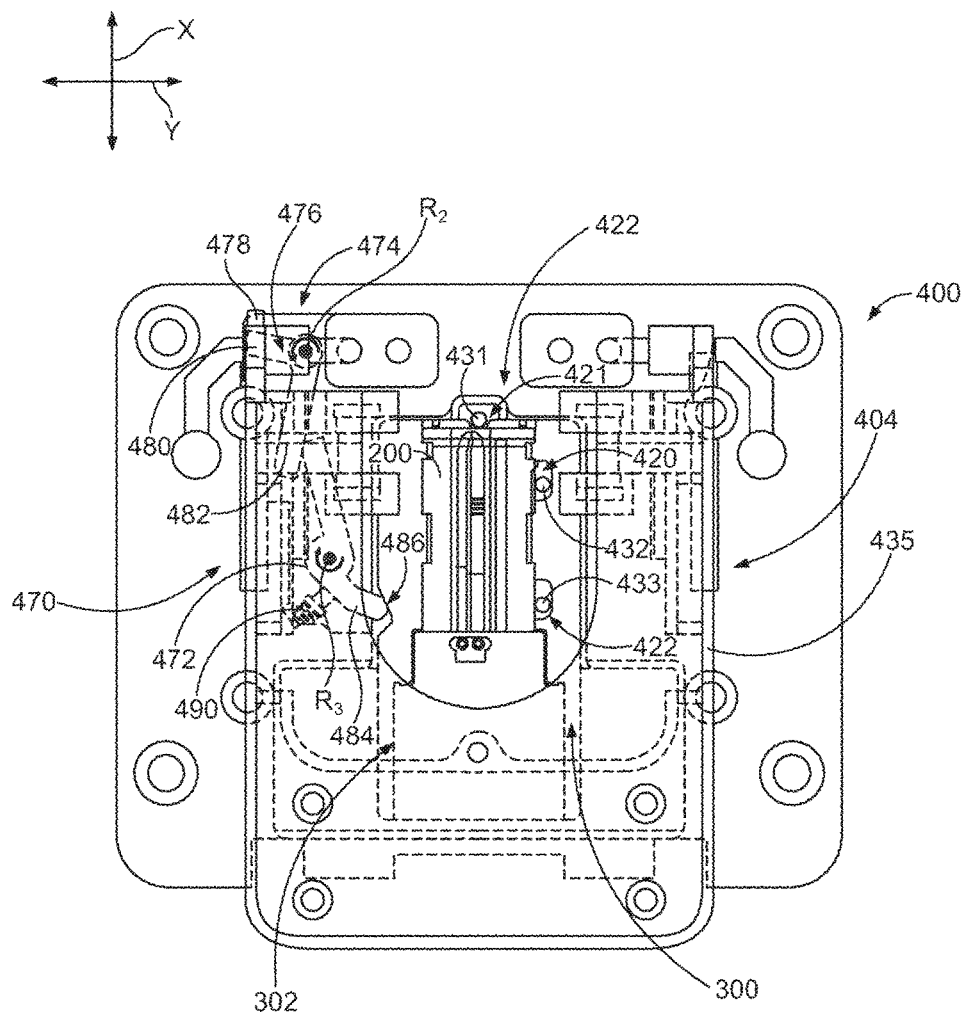
FIG. 19 is a top plan view of the holder of FIG. 16.
Figure 20:
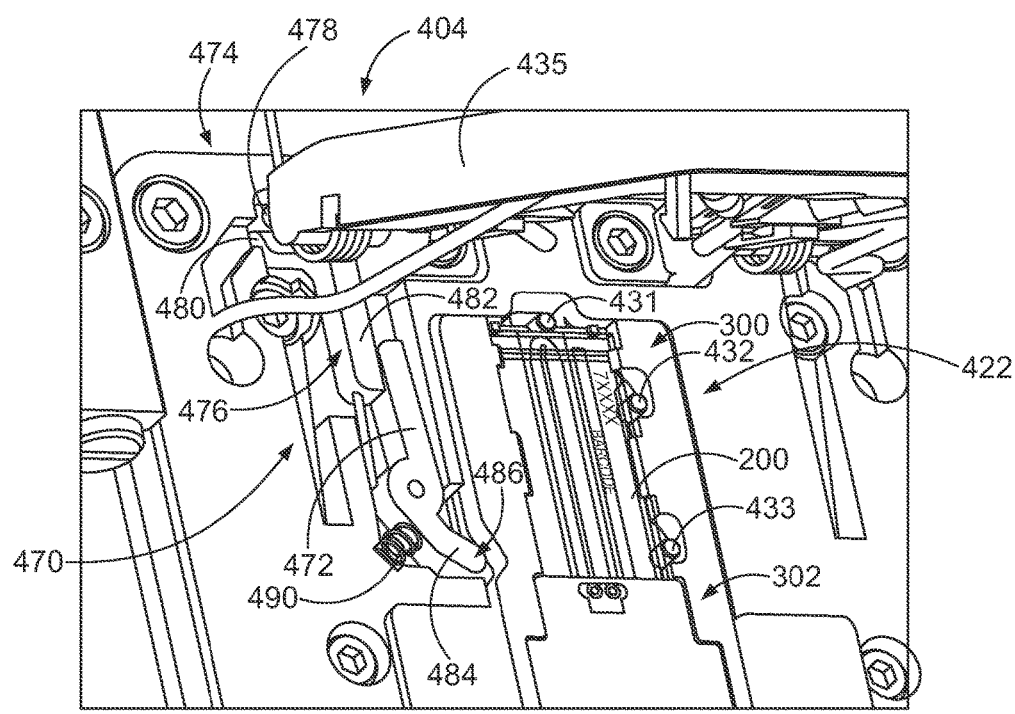
FIG. 20 is a perspective view of the holder of FIG. 16 having a cover assembly in an open position.

FIGS. 19 and 20 illustrate an alignment assembly 470 that may be used with the holder 400 in accordance with one embodiment. FIG. 19 is a plan view of the holder 400 in which the cover housing 435 is shown in phantom to illustrate the alignment assembly 470. FIG. 20 is a perspective view of the holder 400 in which the cover assembly 404 is in the open position. (In both FIGS. 19 and 20, the panel 424 (FIG. 17) has been removed for illustrative purposes.)

The fluidic device 300 is loaded into the loading region 422 in FIGS. 19 and 20. When the fluidic device 300 is loaded, the flow cell 200 is placed onto the base surface 430 (FIG. 18) and the alignment members 432, 433, and 431 are advanced through the recesses 320, 322, and 321 (FIGS. 9 and 10) of the cartridge 302. More specifically, the device window 315 (FIG. 9) along the housing side 305 may be sized and shaped to be greater than a perimeter of the base surface 430. As such, the cartridge 302 or housing 304 may be allowed to fall around the base surface 430, but the flow cell 200 is prevented from falling by the base surface 430. In this manner, the cell side 258 of the flow cell 200 may be pressed against the base surface 430 so that the thermal module 416 may control a temperature of the flow cell 200. When the flow cell 200 is mounted on the base surface 430, the reference surfaces 381-383 (FIG. 11) of the cartridge 302 are pressed against the cell side 256 (FIG. 1111). At this time, a cell plane of the flow cell 200 that extends along the sample 205 may be substantially aligned with an object plane of the imaging system.

In the illustrated embodiment, when the fluidic device 300 is loaded into the loading region 422, an identification reader of the assay system may detect information from the identification transmitter 336 (FIG. 10). For example, the holder 400 may include an identification reader (not shown) in the plate structure 406 proximate to the identification transmitter 336. The identification reading may occur before the cover assembly 404 is mounted onto the fluidic device 300.

With reference to FIGS. 19 and 20, the alignment assembly 470 includes various elements that cooperate together in orienting and positioning the flow cell 200 for imaging. For example, the alignment assembly 470 includes a movable locator arm 472 and an actuator 474 that is operatively coupled to the locator arm 472. As shown, the actuator 474 includes a lever 476 and a pin element 478 that is coupled to the cover housing 435. In the illustrated embodiment, the lever 476 is rotatable about an axis of rotation $R_2$ (FIG. 19). The lever 476 may be L-shaped having a first extension 480 configured to engage the pin element 478 and a second extension 482 configured to engage the locator arm 472. The locator arm 472 is also rotatable about an axis of rotation $R_3$ (FIG. 19) and includes a finger 484 having an engagement end 486. The alignment assembly 470 also includes a biasing element 490 (e.g., a coil spring) that engages the finger 484. The engagement end 486 is configured to engage the cartridge 302 of the fluidic device 300. In alternative embodiments, the engagement end 486 may be configured to directly engage the flow cell 200.

The alignment assembly 470 is in an engaged arrangement in FIG. 19 and in a withdrawn arrangement in FIG. 20. The locator arm 472 is in a retracted position when the alignment assembly 470 is in the withdrawn arrangement and in a biased position when the alignment assembly 470 is in the engaged arrangement. To align the flow cell 200 in the loading region 422, the alignment assembly 470 is changed from the withdrawn arrangement to the engaged arrangement. For example, when the cover housing 435 is moved to the open position shown in FIG. 20, the pin element 478 engages the first extension 480 of the lever 476 causing the lever 476 to rotate about the axis $R_2$ in a counter-clockwise direction (as shown in FIG. 19). The cover housing 435 may be maintained in the open position by the spring elements 464 and 466 (FIG. 16). When the lever 476 is rotated, the second extension 482 rotates about the axis $R_2$ and engages the locator arm 472. The locator arm 472 is rotated about the axis $R_3$ in a clockwise direction (as shown in FIG. 19). When the locator arm 472 is rotated, the locator arm 472 is moved to the retracted position. When moved to the retracted position, the engagement end 486 is moved away from the reference surfaces of the alignment members 431-433.

To change the alignment assembly 470 from the withdrawn arrangement to the engaged arrangement, the cover housing 435 may be rotated toward the fluidic device 300 and mounted over the flow cell 200. When the cover housing 435 is moved toward the fluidic device 300, the pin element 478 is rotated away from the first extension 480 of the lever 476. When the second extension 482 moves away from the locator arm 472, potential energy stored in the biasing element 490 may cause the locator arm 472 to rotate in a counter-clockwise direction such that the engagement end 486 presses against the cartridge 302. As such, the locator arm 472 is moved to the biased position. When moved to the biased position, the engagement end 486 is moved toward the reference surfaces of the alignment members 431-433.

Figure 21:
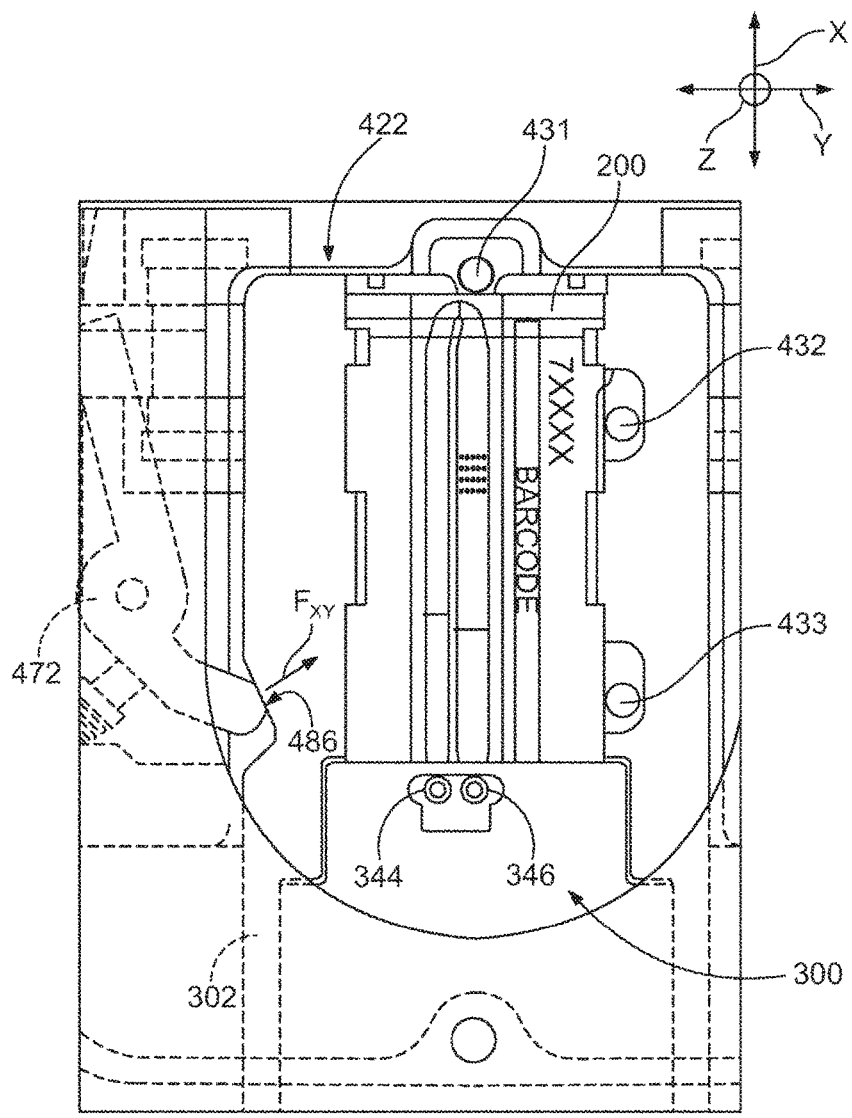
FIG. 21 is an enlarged plan view of the holder of FIG. 16.

FIG. 21 is an enlarged plan view of the fluidic device 300 in the loading region 422 when the engagement end 486 of the locator arm 472 is pressed against the cartridge 302. The engagement end 486 may be configured to move within the XY-plane between the retracted and biased positions. When the engagement end 486 is moved toward the biased position and presses against the cartridge 302, the engagement end 486 provides a force $F_{XY}$ against the cartridge 302. The cartridge 302 may shift along the XY-plane and/or press the flow cell 200 against the reference surfaces of the alignment members 431-433. The force $F_{XY}$ has an X-component and a Y-component. The X-component may press the flow cell 200 against the alignment member 431, and the Y-component may press the flow cell 200 against the alignment members 432 and 433. As such, the alignment member 431 may stop movement of the flow cell 200 in a direction along the X-axis, and the alignment members 432 and 433 may stop movement of the flow cell 200 in a direction along the Y-axis.

Before the alignment assembly 470 is changed to the engaged arrangement, the inlet and outlet passages 346 and 344 of the cover member 306 may be approximately aligned with the inlet and outlet ports 224 and 222 (FIG. 7), respectively, of the flow cell 200. After the alignment assembly 470 is changed to the engaged arrangement, the inlet and outlet passages 346 and 344 are effectively (or operatively) aligned with the inlet and outlet ports 224 and 222 so that fluid may effectively flow therethrough.

Accordingly, the cover assembly 404 may be operatively coupled to the alignment assembly 470 such that one step or action causes the alignment assembly 470 to engage the fluidic device 300. More specifically, as the cover assembly 404 is mounted over the device in the closed position, the actuator 474 moves the locator arm 472 to the biased position. In the biased position, the locator arm 472 holds the flow cell 200 against the reference surfaces of the alignment members 431-433 in a fixed position along the XY-plane. When the cover assembly 404 is in the closed position, the viewing space 442 (FIG. 17) may be located over the flow cell 200 so that an imaging lens may move along the flow cell 200 to image the flow channel 206. As the cover assembly 404 is moved to the open position, the actuator 474 moves the locator arm 472 to the retracted position. However, in the illustrated embodiment, the flow cell 200 remains in position when the locator arm 472 is retracted. Accordingly, the flow cell 200 may be floatable relative to various elements. For example, the flow cell 200 may be floatable with respect to the cover member 306 and the gasket 342 when the cover member 306 is in the mounted position. The flow cell 200 may also be floatable relative to the cover assembly 404 and the base surface 430.

In some embodiments, the alignment assembly 470 and the cover assembly 404 may operate at a predetermined sequence. For example, in particular embodiments, the locator arm 472 is configured to hold the flow cell 200 against the alignment members 431-433 in the fixed position before the cover assembly 404 reaches the closed position. When the cover assembly 404 reaches the closed position, the cover assembly 404 may facilitate pressing the flow cell 200 against the base surface 430 and also pressing the inlet and outlet passages 346 and 344 against the inlet and outlet ports 224 and 222. Generally, the alignment assembly 470 can be configured to position the flow cell 200 in the x and y dimensions after the base surface 430 positions the flow cell 200 in the z dimension. Alternatively, an alignment assembly can be configured to position the flow cell 200 first in the x and y dimensions and then in the z dimension. Thus, alignment in the x, y and z dimensions can occur sequentially and in various orders in response to a single step or motion carried out by a user.

In alternative embodiments, the alignment assembly 470 may not be operatively coupled to the cover assembly 404 as described above. Instead, the alignment assembly 470 and the cover assembly 404 may operate independently from each other. As such, an individual may be required to perform a plurality of steps to align the flow cell 200 and fluidicly couple the flow cell 200. For example, the alignment assembly 470 can be separately actuated by an individual thereby moving the locator arm 472 to align the flow cell 200. After the flow cell 200 is aligned, the individual may then lower the cover assembly 404 onto the flow cell 200. Furthermore, the alignment assembly 470 may comprise additional and/or other components than those described above.

Figure 22:
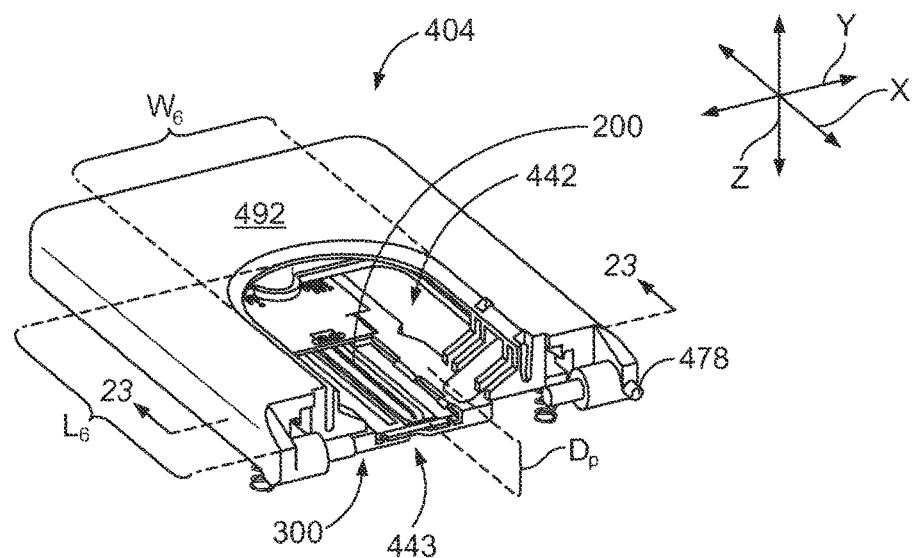
FIG. 22 is a perspective view of a cover assembly that may be used in the holder of FIG. 16.

FIG. 22 is an isolated perspective view of the cover assembly 404 in the closed position. FIG. 22 illustrates dimensions of the viewing space 442. As shown, the cover housing 435 may have a top surface 492. The viewing space 442 may have a depth $D_p$ that is measured from the top surface 492 to the fluidic device 300 or the flow cell 200. The viewing space 442 may also have a width $W_6$ measured along the Y-axis and a length $L_6$ measured along the X-axis.

The dimensions of the viewing space 442 may be sized so that an imaging lens (not shown) may move therethrough over the flow cell 200. More specifically, an imaging lens may enter the viewing space 442 through an access opening 443 and move in a direction along the X-axis over the flow cell 200.

Figure 23:
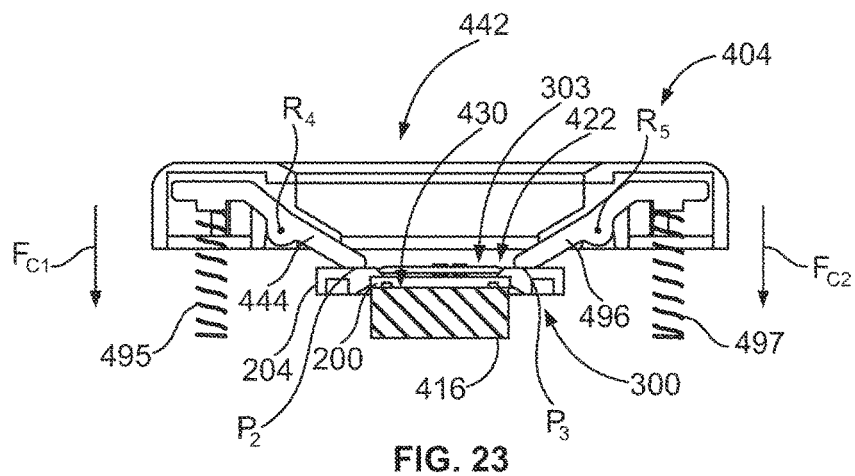
FIG. 23 is a cross-section of the cover assembly taken along the line 23-23 shown in FIG. 22.

FIG. 23 is a cross-section of the cover assembly 404 taken along the line 23-23 in FIG. 22. In the illustrated embodiment, the cover assembly 404 may include a plurality of compression arms 494 and 496. The compression arms 494 and 496 are configured to provide respective compressive forces $F_{C1}$ and $F_{C2}$ against the housing side 303 of the fluidic device 300. In the illustrated embodiment, the compression arms 494 and 496 press against the cartridge 302. However, in alternative embodiments, the compression arms 494 and 496 may press against the flow cell 200.

The compressive forces $F_{C1}$ and $F_{C2}$ press the housing 304 of the fluidic device 300 thereby pressing the cell side 256 (FIG. 9) of the flow cell 200 against the thermal module 416. As such, the flow cell 200 may maintain intimate contact with the base surface 430 for transferring thermal energy therebetween. In the illustrated embodiment, the compression arms 494 and 496 operate independently of each other. For example, each of the compression arms 494 and 496 is operatively coupled to respective compression springs 495 and 497.

As shown in FIG. 23, the compression arms 494 and 496 extend toward the viewing space 442 and the loading region 422. The compression arms 494 and 496 may engage the housing side 303 when the cover assembly 404 is moved to the closed position. As the compression arms 494 and 496 press against the housing side 303, resistance from the housing side 303 may cause the compression arms 494 and 496 to rotate about axes $R_4$ and $R_5$. Each of the compression springs 495 and 497 may resist the rotation of the respective compression arm thereby providing the corresponding compressive force $F_C$ against the housing side 303. Accordingly, the compression arms 494 and 496 are independently biased relative to each other.

Figure 24:
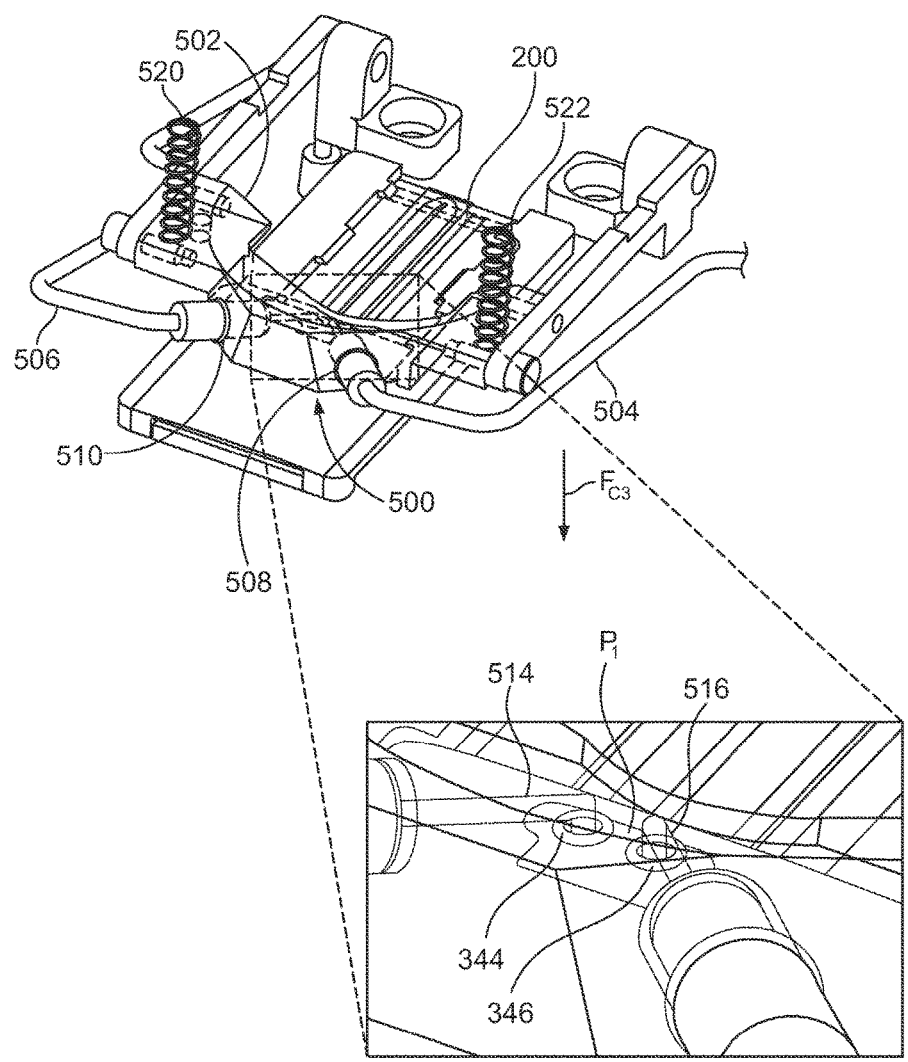
FIG. 24 is a perspective view of a flow system that may be used with the holder of FIG. 16.

FIG. 24 is an isolated perspective view of a flow assembly 500 of the cover assembly 404 (FIG. 16). The flow assembly 500 includes a manifold body 502 and upstream and downstream flow lines 504 and 506. As shown in FIG. 16, the manifold body 502 may extend between the housing legs 436 and 438. Returning to FIG. 24, the flow lines 504 and 506 are mechanically and fluidicly coupled to the manifold body 502 at body ports 508 and 510, respectively. The flow lines 504 and 506 also include line ends 514 and 516 that are configured to be inserted into the inlet and outlet passages 346 and 344 of the gasket 342.

As shown in FIG. 24, the flow assembly 500 is in a mounted position with respect to the gasket 342. In the mounted position, the line ends 514 and 516 are inserted into the inlet and outlet passages 346 and 344, respectively, so that fluid may flow through the flow cell 200. Furthermore, in the mounted position, the flow assembly 500 may press the gasket 342 (FIG. 9) against the flow cell 200 so that the fluid connection is effectively sealed. To this end, the flow assembly 500 may include biasing springs 520 and 522. The biasing springs 520 and 522 are configured to press against an interior of the cover housing 435 (FIG. 16) and provide a force $F_{C3}$ against the gasket 342. The coupling mechanism 450 (FIG. 16) may facilitate maintaining the seal against the gasket 342.

Accordingly, the cover assembly 404 may press against the housing 304 of the fluidic device 300 at three separate compression points. More specifically, the gasket 342 may constitute a first compression point $P_1$ (shown in FIG. 24) when engaged by the line ends 514 and 516, and the compression arms 494 and 496 may contact the fluidic device 300 at second and third compression points $P_2$ and $P_3$ (shown in FIG. 23). As shown in FIGS. 22-24, the three compression points $P_1$-$P_3$ are distributed about the flow cell 200. Moreover, the cover assembly 404 independently provides the compressive forces $F_{C1}$-$F_{C3}$ at the compression points $P_1$-$P_3$. As such, the cover assembly 404 may be configured to provide a substantially uniform compressive force against the fluidic device 300 so that the flow cell 200 is uniformly pressed against the base surface 430 and the fluidic connection is sealed from leakage.

FIG. 25 is a block diagram of a method 530 of positioning a fluidic device for sample analysis. The method 530 includes positioning at 532 a removable fluidic device on a base surface. The fluidic device may be similar to the fluidic device 300 described above. For example, the fluidic device may include a reception space, a flow cell located within the reception space, and a gasket. The flow cell may extend along an object plane in the reception space and be floatable relative to the gasket within the object plane. The method 530 also includes moving the flow cell at 534 within the reception space while on the base surface so that inlet and outlet ports of the flow cell are approximately aligned with inlet and outlet passages of the gasket. The moving operation 534 may include actuating a locator arm to press the flow cell against alignment members.

FIG. 26 is a block diagram illustrating a method 540 of positioning a fluidic device for sample analysis. The fluidic device 300 may be similar to the fluidic device 300 described above. The method 540 includes providing a fluidic device at 542 having a device housing that includes a reception space and a floatable flow cell located within the reception space. The device housing may include recesses that are located immediately adjacent to the reception space. The method also includes positioning at 544 the fluidic device on a support structure having alignment members. The alignment members may be inserted through corresponding recesses. Furthermore, the method 540 may include moving the flow cell at 546 within the reception space. When the flow cell is moved within the reception space, the alignment members may engage edges of the flow cell. The moving operation 546 may include actuating a locator arm to press the flow cell against the alignment members.

FIG. 27 is a block diagram illustrating a method 550 for orienting a sample area with respect to mutually perpendicular X, Y, and Z-axes. The method 550 includes providing an alignment assembly at 552. The alignment assembly may be similar to the alignment assembly 470 described above. More specifically, the alignment assembly may include a movable locator arm that has an engagement end. The locator arm may be movable between retracted and biased positions. The method 550 also includes positioning a fluidic device at 554 on a base surface that faces in a direction along the Z-axis and between a plurality of reference surfaces that face in respective directions along an XY-plane. Furthermore, the method 550 may include moving at 556 the locator arm to the biased position. The locator arm can press the device against the reference surfaces such that the device is held in a fixed position.

Figure 28:
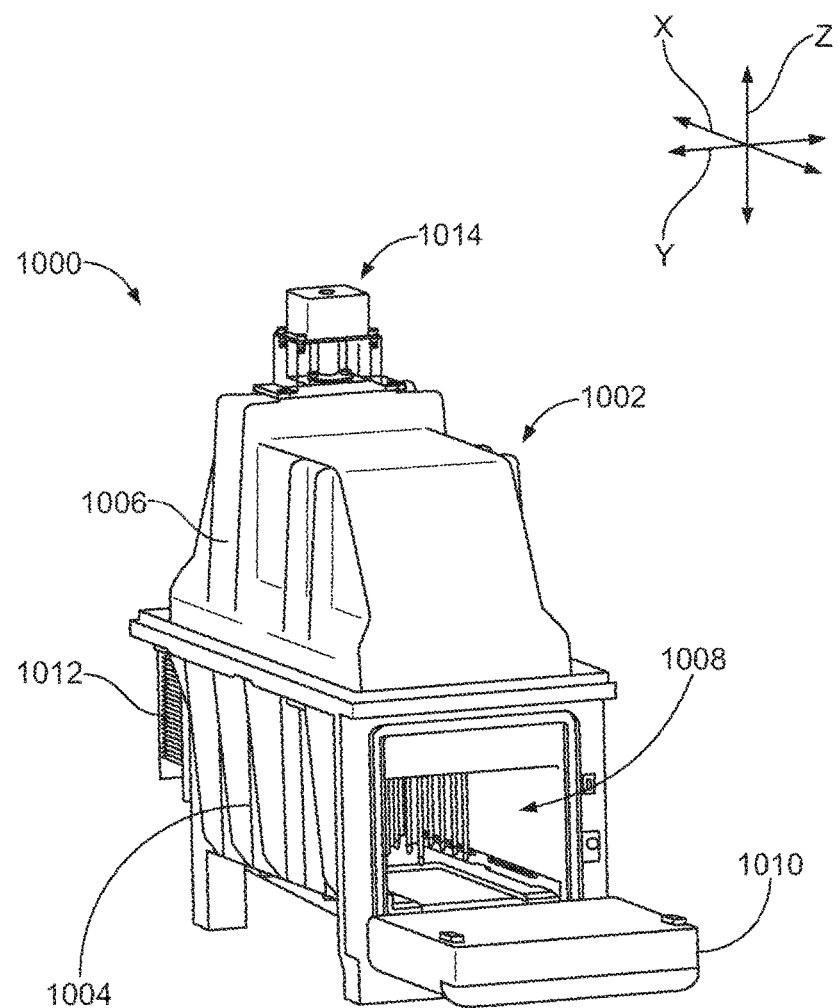
FIG. 28 is a perspective view of a fluid storage system formed in accordance with one embodiment.

FIGS. 28-37 illustrate various features of a fluid storage system 1000 (FIG. 28). The storage system 1000 is configured to store and regulate a temperature of various fluids that may be used during predetermined assays. The storage system 1000 may be used by the workstation 160 (FIG. 2) and enclosed by the casing 162 (FIG. 3). As shown in FIG. 28, the storage system 1000 includes an enclosure 1002 having a base shell (or first shell) 1004 and a top shell (or second shell) 1006 that are coupled together and define a system cavity 1008 therebetween. The enclosure 1002 may also include a system door 1010 that is configured to open and provide access to the system cavity 1008. Also shown, the storage system 1000 may include a temperature-control assembly 1012 that is coupled to a rear of the enclosure 1002 and a elevator drive motor 1014 that is located on the top shell 1006.

Figure 29:
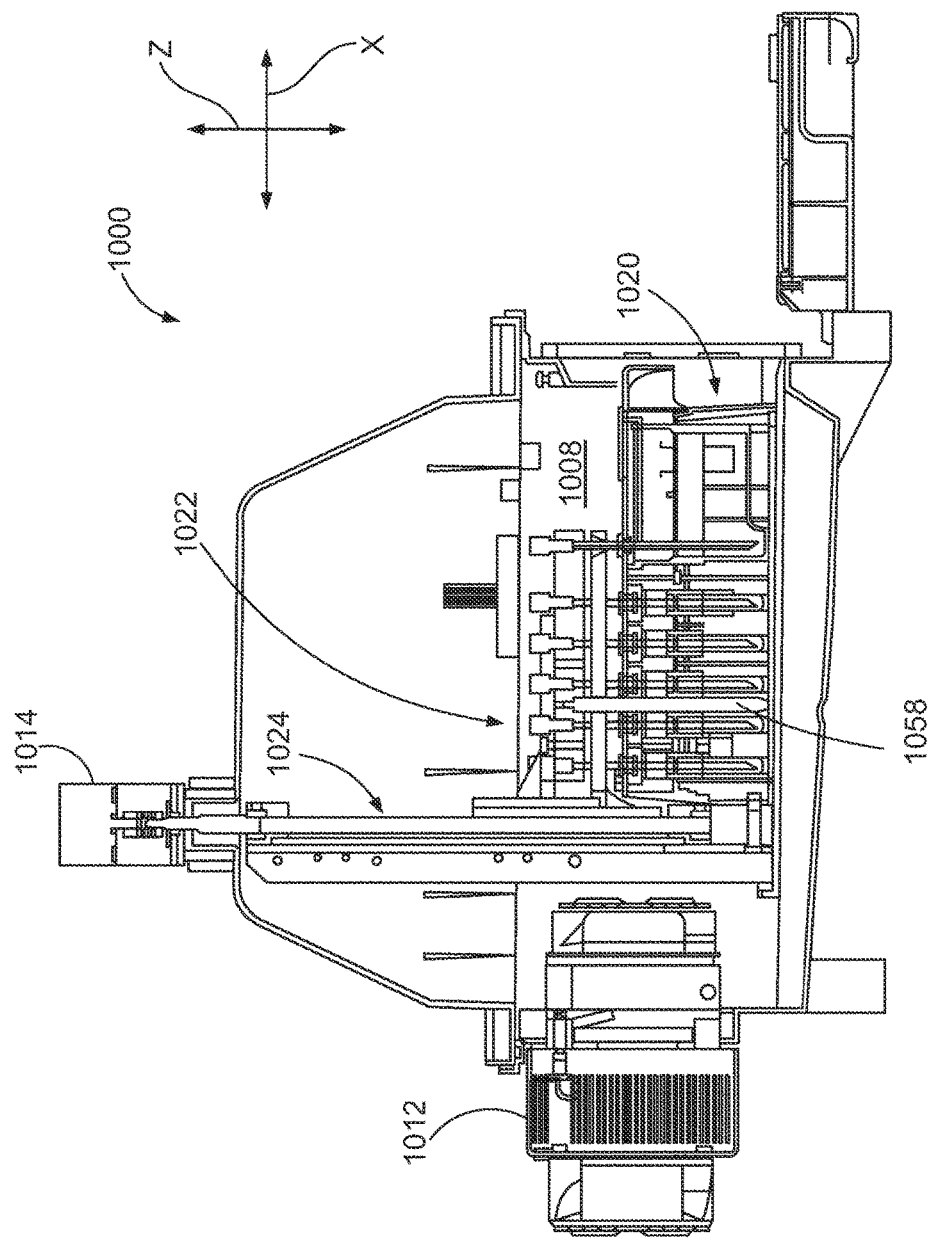
FIG. 29 is a side cross-section of the fluid storage system of FIG. 28.

FIG. 29 is a side cross-section of the storage system 1000 and illustrates the system cavity 1008 in greater detail. The storage system 1000 may also include a reaction component tray (or reaction component storage unit) 1020 and a fluid removal assembly 1022 that includes an elevator mechanism 1024. The tray 1020 is configured to hold a plurality of tubes or containers for storing fluids. The elevator mechanism 1024 includes the drive motor 1014 and is configured to move components of the removal assembly 1022 bi-directionally along the Z-axis. In FIG. 29, the tray 1020 is located in a fluid-removal position such that fluid held by the tray 1020 may be removed and delivered to, for example, a fluidic device for performing a desired reaction or for flushing the flow channels of the fluidic device.

Also shown, the temperature-control assembly 1012 may project into the system cavity 1008. The temperature-control assembly 1012 is configured to control or regulate a temperature within the system cavity 1008. In the illustrated embodiment, the temperature-control assembly 1012 includes a thermo-electric cooling (TEC) assembly.

Figure 30:
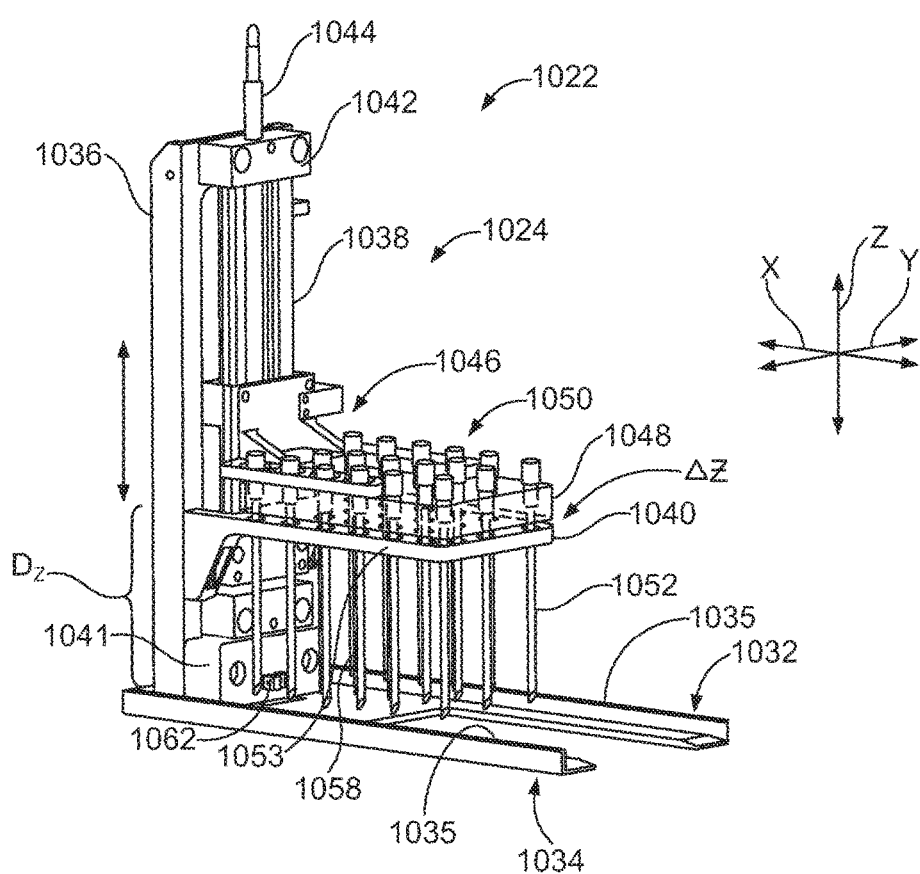
FIG. 30 is a perspective view of a removal assembly that may be used with the fluid storage system of FIG. 28.

FIG. 30 is a perspective view of the removal assembly 1022. As shown, the removal assembly 1022 may include a pair of opposing guide rails 1032 and 1034. The opposing guide rails 1032 and 1034 are configured to receive and direct the tray 1020 to the fluid-removal position shown in FIG. 29. The guide rails 1032 and 1034 may include projected features or ridges 1035 that extend longitudinally along the guide rails 1032 and 1034. The guide rails 1032 and 1034 are configured to be secured to the base shell 1004 (FIG. 28). The removal assembly 1022 also includes support beams (or uprights) 1036 and 1038 that extend in a direction along the Z-axis. A guide plate 1040 of the removal assembly may be coupled to the support beams 1036 and 1038 at an elevated distance $D_Z$ and project therefrom along the XY-plane. In the illustrated embodiment, the guide plate 1040 is affixed to the support beams 1036 and 1038.

The elevator mechanism 1024 includes structural supports 1041 and 1042, a lead screw 1044 that extends between the structural supports 1041 and 1042, and a stage assembly 1046 that includes a transport platform 1048. The structural supports 1041 and 1042 are secured to opposite ends of the support beams 1036 and 1038 and are configured to support the elevator mechanism 1024 during operation. Threads of the lead screw 1044 are operatively coupled to the stage assembly 1046 such that when the lead screw 1044 is rotated, the stage assembly 1046 moves in a linear direction along the Z-axis (indicated by the double arrows).

The transport platform 1048 is configured to hold an array of sipper tubes 1050. The sipper tubes 1050 may be in fluid communication with a system pump (not shown) that is configured to direct a flow of fluid through the sipper tubes 1050. As shown, the sipper tubes 1050 include distal portions 1052 that are configured to be inserted into component wells 1060 (shown in FIG. 31) of the tray 1020. The distal portions 1052 extend through corresponding openings 1053 of the guide plate 1040.

The elevator mechanism 1024 is configured to move the sipper tubes 1050 between withdrawn and deposited levels. At the deposited level (shown in FIGS. 50 and 51), the distal portions 1052 of the sipper tubes 1050 are inserted into the component wells 1060 to remove fluid therefrom. At the withdrawn level, the distal portions 1052 are completely removed from the tray 1020 such that the tray 1020 may be removed from the system cavity 1008 (FIG. 28) without damage to the sipper tubes 1050 or the tray 1020. More specifically, when the drive motor 1014 rotates the lead screw 1044, the stage assembly 1046 moves along the Z-axis in a direction that is determined by a rotational direction of the lead screw 1044. Consequently, the transport platform 1048 moves along the Z-axis while holding the sipper tubes 1050. If the transport platform 1048 advances toward the guide plate 1040, the distal portions 1052 slide through the corresponding openings 1053 of the guide plate 1040 toward the tray 1020. The guide plate 1040 is configured to prevent distal portions 1052 from becoming misaligned with the component wells 1060 before the distal portions 1052 are inserted therein. When the elevator mechanism 1024 moves the stage assembly 1046 away from the guide plate 1040, a distance (ΔZ) between the transport platform 1048 and the guide plate 1040 increases until the distal portions 1052 are withdrawn from the component wells 1060 of the tray 1020.

FIG. 30 illustrates additional features for operating the elevator mechanism 1024. For example, the stage assembly 1046 may also include a guide pin 1058 (also shown in FIG. 29) that is affixed to and extends from the transport platform 1048 in a direction that is parallel to the sipper tubes 1050. The guide pin 1058 also extends through a corresponding opening 1053 of the guide plate 1040. In the illustrated embodiment, the guide pin 1058 extends a greater distance than the sipper tubes 1050 so that the guide pin 1058 reaches the tray 1020 before the sipper tubes 1050 are inserted into the component wells 1060. Thus, if the tray 1020 is misaligned with respect to the sipper tubes 1050, the guide pin 1058 may engage the tray 1020 and adjust the position of the tray 1020 so that the component wells 1060 are properly aligned with the corresponding sipper tubes 1050 before the sipper tubes 1050 are inserted therein.

In addition to the above, the removal assembly 1022 may include a position sensor 1062 and a location sensor (not shown). The position sensor 1062 is configured to receive a flag 1063 (shown in FIG. 34) of the tray 1020 to determine that the tray 1020 is present in the system cavity 1008 (FIG. 28) and at least approximately aligned for receiving the sipper tubes 1050. The location sensor may detect a flag 1064 of the stage assembly 1046 to determine a level of the stage assembly 1046. If the flag 1064 has not reached a threshold level along the Z-axis, the location sensor may communicate with the workstation 160 (or other assay system) to notify the user that the tray 1020 is not ready for removal. The workstation 160 could also prevent the user from opening the system door 1010.

Furthermore, when the distal portions 1052 of the sipper tubes 1050 are initially inserted into the component wells 1060, the sipper tubes 1050 may pierce protective foils that cover the component wells 1060. In some instances, the foils may grip the sipper tubes 1050. When the sipper tubes 1050 are subsequently withdrawn from the corresponding component wells 1060, the gripping of the protective foils may collectively lift the tray 1020. However, in the illustrated embodiment, the ridges 1035 are configured to grip a tray base 1070 (FIG. 31) and prevent the tray base 1070 from being lifted in a direction along the Z-axis. For example, the ridges 1035 may grip a lip 1071 of the tray base 1070.

FIGS. 31-34 illustrate different views of the tray 1020. The tray 1020 is configured to hold a plurality of component wells 1060. The component wells 1060 may include various reaction components, such as, but not limited to, one or more samples, polymerases, primers, denaturants, linearization mixes for linearizing DNA, enzymes suitable for a particular assay (e.g., cluster amplification or SBS), nucleotides, cleavage mixes, oxidizing protectants, and other reagents. In some embodiments, the tray 1020 may hold all fluids that are necessary to perform a predetermined assay. In particular embodiments, the tray 1020 may hold all reaction components necessary for generating a sample (e.g., DNA clusters) within a flow cell and performing sample analysis (e.g., SBS). The assay may be performed without removing or replacing any of the component wells 1060.

Figure 31:
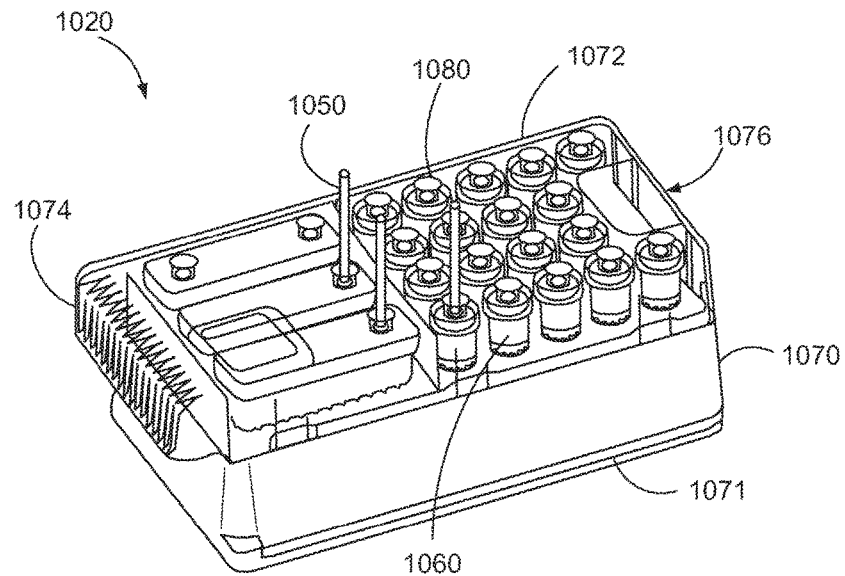
FIG. 31 is a perspective view of a reaction component tray formed in accordance with one embodiment.
Figure 32:
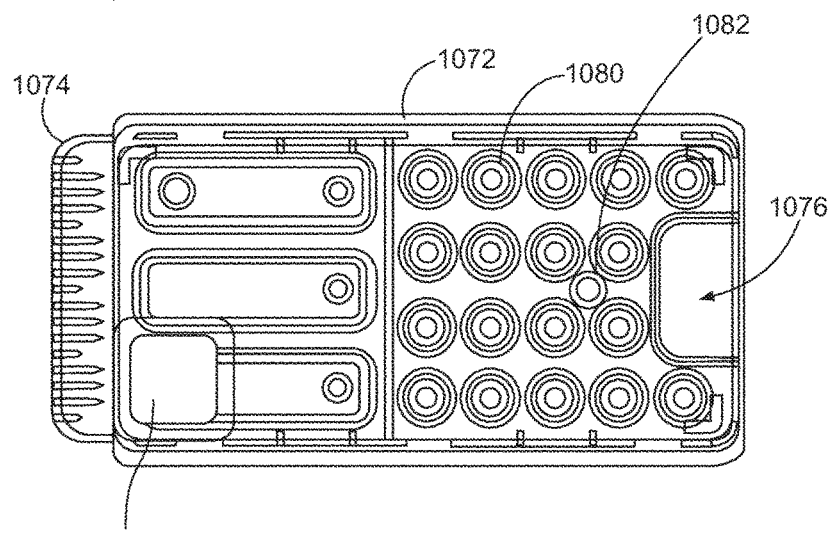
FIG. 32 is a top plan view of the tray shown in FIG. 31.

The component wells 1060 include rectangular component wells 1060A (shown in FIGS. 35-36) and tubular component wells 1060B (shown in FIG. 37). The tray 1020 includes a tray base 1070 and a tray cover 1072 coupled to the tray base 1070. As shown in FIGS. 31 and 32, the tray cover 1072 includes a handle 1074 that is sized and shaped to be gripped by a user of the tray 1020. The tray cover 1072 may also include a grip recess 1076 that is sized and shaped to receive one or more fingers of the user.

As shown in FIGS. 31 and 32, the tray cover 1072 may include a plurality of tube openings 1080 that are aligned with corresponding component wells 1060. The tube openings 1080 may be shaped to direct the sipper tubes 1050 (exemplary sipper tubes 1050 are shown in FIG. 31) into the corresponding component wells 1060. As shown in FIG. 32, the tray cover 1072 also includes a pin opening 1082 that is sized and shaped to receive the guide pin 1058. The guide pin 1058 is configured to provide minor adjustments to the position of the tray 1020 if the guide pin 1058 approaches and enters the pin opening 1082 in a misaligned manner. Also shown, the tray 1020 may include an identification tag 1084 along a surface of the tray cover 1072. The identification tag 1084 is configured to be detected by a reader to provide the user with information regarding the fluids held by the component wells 1060.

Figure 33:
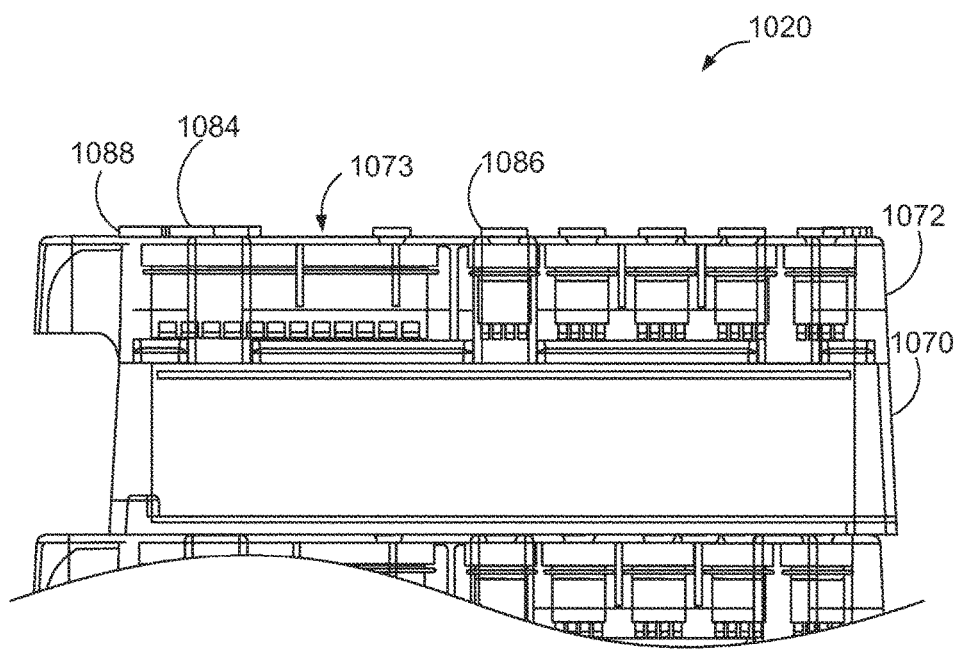
FIG. 33 is a side view of the tray shown in FIG. 31.
Figure 34:
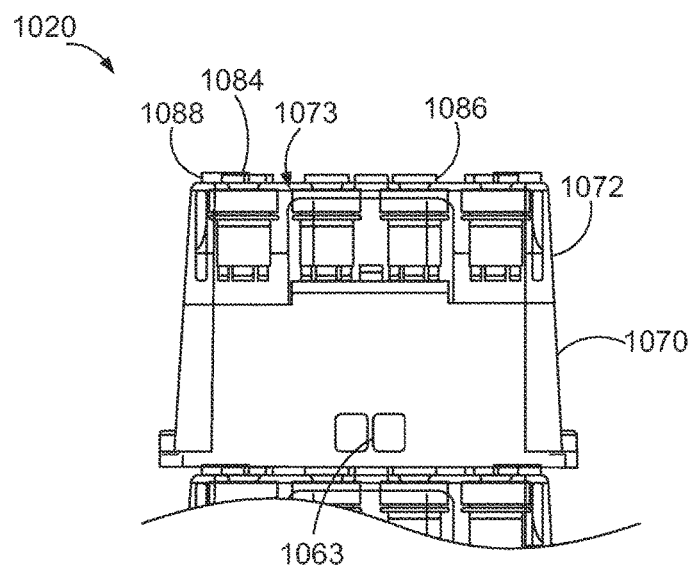
FIG. 34 is a front view of the tray shown in FIG. 31.

As shown in FIGS. 33 and 34, the tube openings 1080 are at least partially defined by rims 1086 that project from a surface 1073 of the tray cover 1072. The rims 1086 project a small distance away from the surface 1073 to prevent inadvertent mixing of fluids that are accidentally deposited onto the tray cover 1072. Likewise, the identification tag 1084 may be attached to a raised portion 1088 of the tray cover 1072. The raised portion 1088 may also protect the identification tag 1084 from inadvertently contacting fluids.

FIG. 35 shows a side cross-sectional view of the component well 1060A, and FIG. 36 shows a bottom perspective view of the component well 1060A. As shown, the component well 1060A includes opposite first and second ends 1091 and 1092 and a reservoir 1090 (FIG. 35) extending therebetween. The reservoir 1090 has a depth $D_R$ (FIG. 35) that increases as the reservoir 1090 extends from the second end 1092 to the first end 1091. The component well 1060A is configured to receive the sipper tube 1050 in a deeper portion of the reservoir 1090. As shown in FIG. 36, the component well 1060A includes a plurality of projections 1094 along an exterior surface that are configured to rest upon a surface of the tray base 1070.

FIG. 37 is a perspective view of the component well 1060B. As shown, the component well 1060B may also include a plurality of projections 1096 around an exterior surface of the component well 1060B. The component well 1060B extends along a longitudinal axis 1097 and has a profile that tapers as the component well 1060B extends longitudinally to a bottom 1098. The bottom 1098 may have a substantially planar surface.

FIG. 61 illustrates a method 960 for performing an assay for biological or chemical analysis. In some embodiments, the assay may include a sample generation protocol and a sample analysis protocol. For example, the sample generation protocol may include generating clusters of DNA through bridge amplification and the sample analysis protocol may include sequencing-by-synthesis (SBS) analysis using the clusters of DNA. The sample generation and sample analysis operations may be conducted within a common assay system, such as the assay system 100 or the workstation 160, and without user intervention between the operations. For instance, a user may be able to load a fluidic device into the assay system. The assay system may automatically generate a sample for analysis and carry out the steps for performing the analysis.

With respect to FIG. 61, the method 960 includes establishing at 962 a fluid connection between a fluidic device having a sample area and a reaction component storage unit having a plurality of different reaction components. The reaction components may be configured for conducting one or more assays. The fluidic device may be, for example, the fluidic device 300 or the flow cell 200 described above. In some embodiments, the sample area includes a plurality of reaction components (e.g., primers) immobilized thereon. The storage unit may be, for example, the storage unit 1020 described above. The reaction components may include sample-generation components that are configured to be used to generate the sample, and sample-analysis components that are configured to be used to analyze the sample. In particular embodiments, the sample-generation components include reaction components for performing bridge amplification as described above. Furthermore, in particular embodiments, the sample-analysis components include reaction components for performing SBS analysis as described above.

The method 960 also includes generating at 964 a sample at the sample area of the fluidic device. The generating operation 964 may include flowing different sample-generation components to the sample area and controlling reaction conditions at the sample area to generate the sample. For example, a thermocycler may be used to facilitate hybridizing nucleic acids. However, isothermal methods can be used if desired. Furthermore, a flow rate of the fluids may be controlled to permit hybridization or other desired chemical reactions. In particular embodiments, the generating operation 964 includes conducting multiple bridge-amplification cycles to generate a cluster of DNA.

An exemplary protocol for bridge amplification can include the following steps. A flow cell is placed in fluid communication with a reaction component storage unit. The flow cell includes one or more surfaces to which are attached pairs of primers. A solution having a mixture of target nucleic acids of different sequences is contacted with a solid support. The target nucleic acids can have common priming sites that are complementary to the pairs of primers on the flow cell surface such that the target nucleic acids bind to a first primer of the pairs of primers on the flow cell surface. An extension solution containing polymerase and nucleotides can be introduced to the flow cell such that a first amplification product, which is complementary to the target nucleic acid, is formed by extension of the first primer. The extension solution can be removed and replaced with a denaturation solution. The denaturation solution can include chemical denaturants such as sodium hydroxide and/or formamide. The resulting denaturation conditions release the original strand of the target nucleic acid, which can then be removed from the flow cell by removing the denaturation solution and replacing it with the extension solution. In the presence of the extension solution the first amplification product, which is attached to the support, can then hybridize with a second primer of the primer pairs attached to the flow cell surface and a second amplification product comprising an attached nucleic acid sequence complementary to the first amplification product can be formed by extension of the second primer. Repeated delivery of the denaturation solution and extension solution can be used to form clusters of the target nucleic acid at discrete locations on the surface of the flow cell. Although the above protocol is exemplified using chemical denaturation, it will be understood that thermal denaturation can be carried out instead albeit with similar primers and target nucleic acids. Further description of amplification methods that can be used to produce clusters of immobilized nucleic acid molecules is provided, for example, in U.S. Pat. No. 7,115,400; U.S. Publication No. 2005/0100900; WO 00/18957; or WO 98/44151, each of which is incorporated by reference herein.

The method 960 also includes analyzing at 966 the sample at the sample area. Generally, the analyzing operation 966 may include detecting any detectable characteristic at the sample area. In particular embodiments, the analyzing operation 966 includes flowing at least one sample-analysis component to the sample area. The sample-analysis component may react with the sample to provide optically detectable signals that are indicative of an event-of-interest (or desired reaction). For example, the sample-analysis components may be fluorescently-labeled nucleotides used during SBS analysis. When excitation light is incident upon the sample having fluorescently-labeled nucleotides incorporated therein, the nucleotides may emit optical signals that are indicative of the type of nucleotide (A, G, C, or T), and the imaging system may detect the optical signals.

A particularly useful SBS protocol exploits modified nucleotides having removable 3' blocks, for example, as described in WO 04/018497, US 2007/0166705A1 and U.S. Pat. No. 7,057,026, each of which is incorporated herein by reference. Repeated cycles of SBS reagents can be delivered to a flow cell having target nucleic acids attached thereto, for example, as a result of the bridge amplification protocol set forth above. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, Mass., USA, part number M5505S), by exposure to heat or alkali, cleavage of ribonucleotides incorporated into amplification products otherwise comprised of deoxyribonucleotides, photochemical cleavage or cleavage of a peptide linker. After the linearization step a sequencing primer can be delivered to the flow cell under conditions for hybridization of the sequencing primer to the target nucleic acids that are to be sequenced.

The flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'-OH group available to direct further sequence extension and therefore the polymerase cannot add further nucleotides. The SBS extension reagent can be removed and replaced with scan reagent containing components that protect the sample under excitation with radiation. Exemplary components for scan reagent are described in US publication US 2008/0280773 A1 and U.S. Ser. No. 13/018, 255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Exemplary deblock reagents that are useful for respective blocking groups are described in WO04018497, US 2007/0166705A1 and U.S. Pat. No. 7,057,026, each of which is incorporated herein by reference. The deblock reagent can be washed away leaving target nucleic acids hybridized to extended primers having 3' OH groups that are now competent for addition of a further nucleotide. Accordingly the cycles of adding extension reagent, scan reagent, and deblock reagent, with optional washes between one or more of the steps, can be repeated until a desired sequence is obtained. The above cycles can be carried out using a single extension reagent delivery step per cycle when each of the modified nucleotides has a different label attached thereto, known to correspond to the particular base. The different labels facilitate discrimination between the bases added during each incorporation step. Alternatively, each cycle can include separate steps of extension reagent delivery followed by separate steps of scan reagent delivery and detection, in which case two or more of the nucleotides can have the same label and can be distinguished based on the known order of delivery.

Continuing with the example of nucleic acid clusters in a flow cell, the nucleic acids can be further treated to obtain a second read from the opposite end in a method known as paired end sequencing. Methodology for paired end sequencing are described in PCT publication WO07010252, PCT application Serial No. PCTGB2007/003798 and US patent application publication US 2009/0088327, each of which is incorporated by reference herein. In one example, a series of steps may be performed as follows: generate clusters as set forth above, linearize as set forth above, hybridize a first sequencing primer and carry out repeated cycles of extension, scanning and deblocking, also as set forth above, "invert' the target nucleic acids on the flow cell surface by synthesizing a complementary copy, linearize the resynthesized strand, hybridize a first sequencing primer and carry out repeated cycles of extension, scanning and deblocking, also as set forth above. The inversion step can be carried out be delivering reagents as set forth above for a single cycle of bridge amplification.

Although the analyzing operation has been exemplified above with respect to a particular SBS protocol, it will be understood that other protocols for sequencing any of a variety of other molecular analyses can be carried out as desired. Appropriate modification of the apparatus and methods to accommodate various analyses will be apparent in view of the teaching set forth herein and that which is known about the particular analysis method.

In some embodiments, the method 960 is configured to be conducted with minimal user intervention. The generating and analyzing operations 964 and 966 may be conducted in an automated manner by an assay system. For example, in some cases, a user may only load the fluidic device and the storage unit and activate the assay system to perform the method 960. In some embodiments, during the generating and analyzing operations 964 and 966, the storage unit and the fluidic device remain in fluid communication from a beginning of the generating operation and throughout the analyzing operation until the sample is sufficiently analyzed. In other words, the fluidic device and the storage unit may remain in fluid communication from before the sample is generated until after the sample is analyzed. In some embodiments, the fluidic device is continuously held by the device holder from a beginning of the generating operation and throughout the analyzing operation until the sample is sufficiently analyzed. During such time, the device holder and an imaging lens may be automatically moved with respect to each other. The storage unit and the fluidic device may remain in fluid communication when the fluidic device and the imaging lens are automatically moved with respect to each other. In some embodiments, the assay system is contained within a workstation housing and the generating and analyzing operations 964 and 966 are conducted exclusively within the workstation housing.

Figure 38:
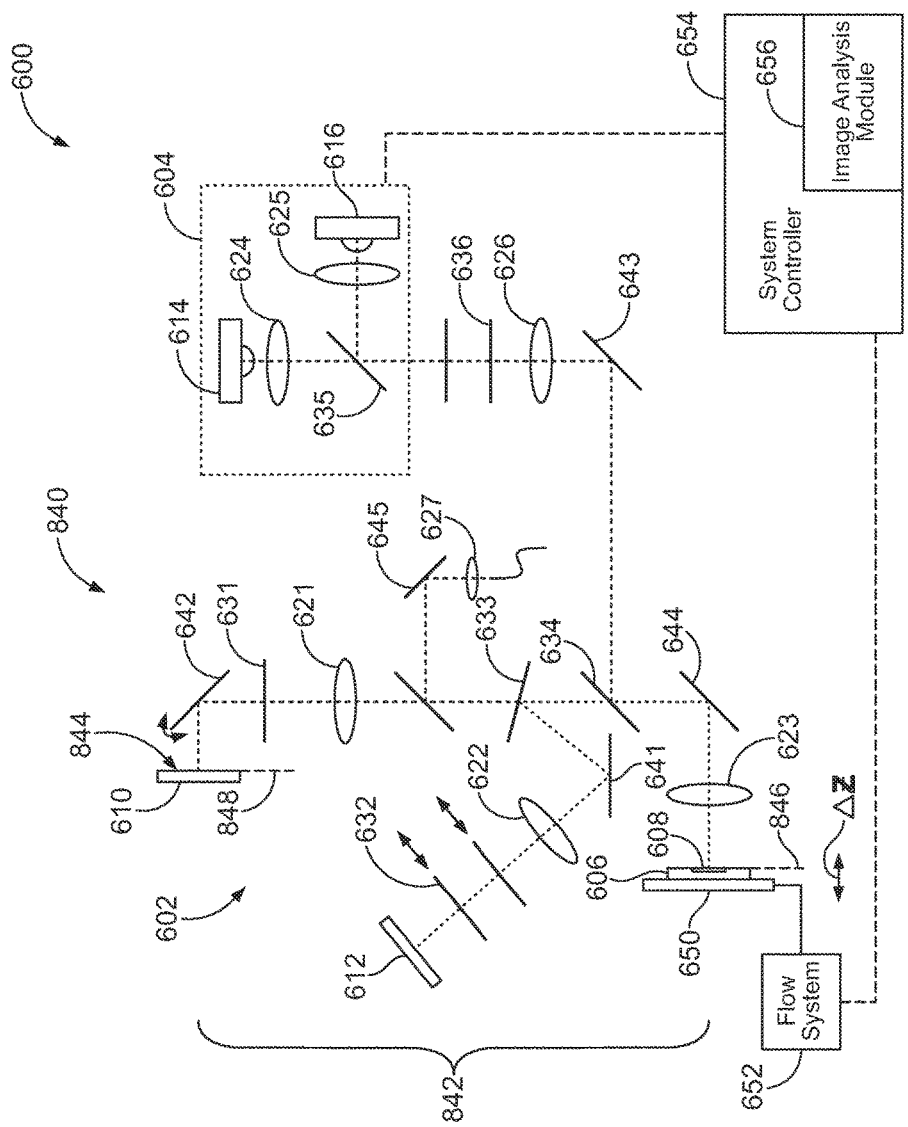
FIG. 38 is a diagram of an optical imaging system in accordance with one embodiment.

FIG. 38 is a schematic illustration of an optical imaging system 600 formed in accordance with one embodiment. The imaging system 600 includes an optical assembly 602, a light source (or excitation light) module or assembly 604, a flow cell 606 having a sample area 608, and imaging detectors 610 and 612. The light source module 604 includes first and second excitation light sources 614 and 616 that are configured to illuminate the sample area 608 with different excitation spectra. In particular embodiments, the first and second excitation light sources 614 and 616 comprise first and second semiconductor light sources (SLSs). SLSs may include light-emitting diodes (LEDs) or laser diodes. However, other light sources may be used in other embodiments, such as lasers or arc lamps. The first and second SLSs may have fixed positions with respect to the optical assembly 602.

As shown, the optical assembly 602 may include a plurality of optical components. For example, the optical assembly 602 may include lenses 621-627, emission filters 631-634, excitation filters 635 and 636, and mirrors 641-645. The plurality of optical components are arranged to at least one of (a) direct the excitation light toward the sample area 608 of the flow cell 606 or (b) collect emission light from the sample area 608. Also shown, the imaging system 600 may also include a flow system 652 that is in fluid communication with the flow cell 606 and a system controller 654 that is communicatively coupled to the first and second excitation light sources 614 and 616 and the flow system 652. The controller 654 is configured to activate the flow system 652 to flow reagents to the sample area 608 and activate the first and second SLSs after a predetermined time period.

For example, FIG. 60 illustrates a method 900 for performing an assay for biological or chemical analysis. In particular embodiments, the assay may include a sequencing-by-synthesis (SBS) protocol. The method 900 includes flowing reagents through a flow channel of a flow cell at 902. The flow cell may have a sample area that includes a sample with biomolecules configured to chemically react with the reagents. The method 900 also includes illuminating the sample area at 904 with first and second semiconductor light sources (SLSs). The first and second SLSs provide first and second excitation spectra, respectively. The biomolecules of the sample may provide light emissions that are indicative of a binding reaction when illuminated by the first or second SLSs. Furthermore, the method 900 includes detecting the light emissions from the sample area at 906. Optionally, the method 900 may include moving the flow cell at 908 relative to an imaging lens and repeating the illuminating and detecting operations 904 and 906. The steps shown in FIG. 60 and exemplified above can be repeated for multiple cycles of a sequencing method.

Figure 39:
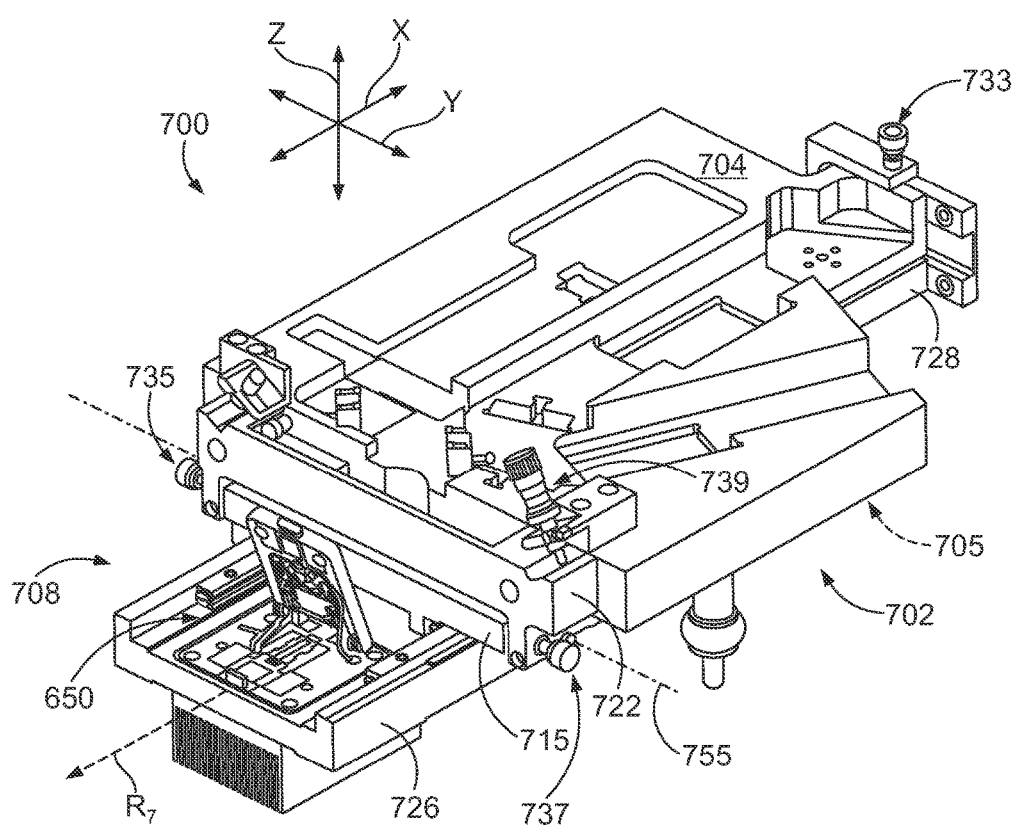
FIG. 39 is a perspective view of a motion-control system in accordance with one embodiment.
Figure 40:
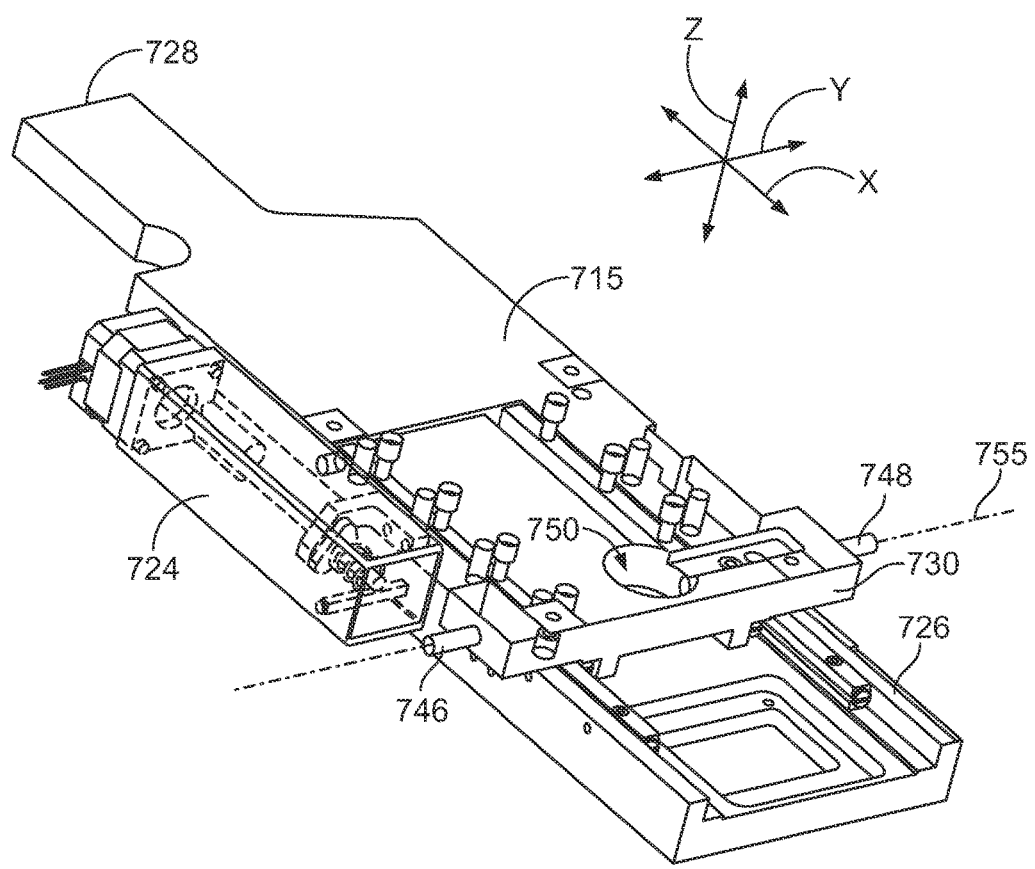
FIG. 40 is a perspective view of components that may be used with the motion-control system of FIG. 39.

FIGS. 39 and 40 illustrate various features of a motion-control system 700 formed in accordance with one embodiment that may be used with the imaging system 600. The motion-control system 700 includes an optical base plate 702 and a sample deck 708 that is movably coupled to the base plate 702. As shown, the base plate 702 has a support side 704 and a bottom side 705. The support and bottom sides 704 and 705 face in opposite directions along the Z-axis. The base plate 702 is configured to support a majority of the optical components of the optical assembly 602 (FIG. 38) on the support side 704. The base plate 702 and the sample deck 708 may be movably coupled to each other by an intermediate support 715 and a face plate 722 such that the sample holder 650 may substantially rotate about the X and Y axes, shift along the Y axis, and slide along the X axis.

FIG. 40 is an isolated perspective view of the intermediate support 715, a motor assembly 724, and a movable platform 726 of the sample deck 708 (FIG. 39). The motor assembly 724 is operatively coupled to the platform 726 and is configured to slide the platform 726 bi-directionally along the X-axis. As shown, the intermediate support 715 includes a tail end 728 and an imaging end 730. The intermediate support 715 may include pins 746 and 748 proximate to the imaging end 730 that project away from each other along the Y-axis. Proximate to the imaging end 730, the intermediate support 715 may include a lens opening 750 that is sized and shaped to allow the imaging lens 623 (FIG. 38) to extend therethrough. In the illustrated embodiment, the pins 746 and 748 have a common line 755 extending therethrough that also extends through the lens opening 750.

Returning to FIG. 39, the platform 726 is coupled to the bottom side 705 through the intermediate support 715. Accordingly, a weight of the sample deck 708 may be supported by the base plate 702. Furthermore, the motion-control system 700 may include a plurality of alignment devices 733, 735, 737, and 739 that are configured to position the sample holder 650. In the illustrated embodiment, the alignment devices 733, 735, 737, and 739 are micrometers. The alignment device 733 is operatively coupled to the tail end 728 of the intermediate support 715. When the alignment device 733 is activated, the tail end 728 may be moved in a direction along the Z-axis. Consequently, the intermediate support 715 may rotate about the pins 746 and 748 (FIG. 40) or, more specifically, about the line 755. When the alignment devices 735 and 737 are activated, the sample holder 650 may shift along the Y-axis as directed. When the alignment device 739 is activated, the sample holder 650 may rotate about an axis of rotation $R_7$ that extends parallel to the X-axis.

Figure 42:
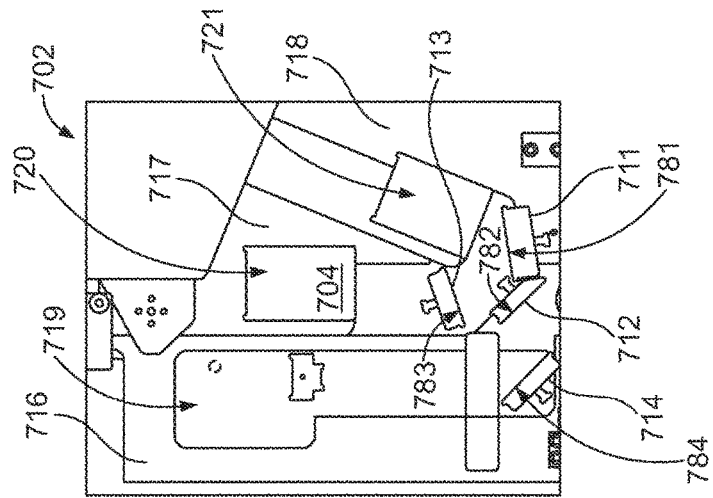
FIG. 42 is a plan view of the base plate of FIG. 41.
Figure 41:
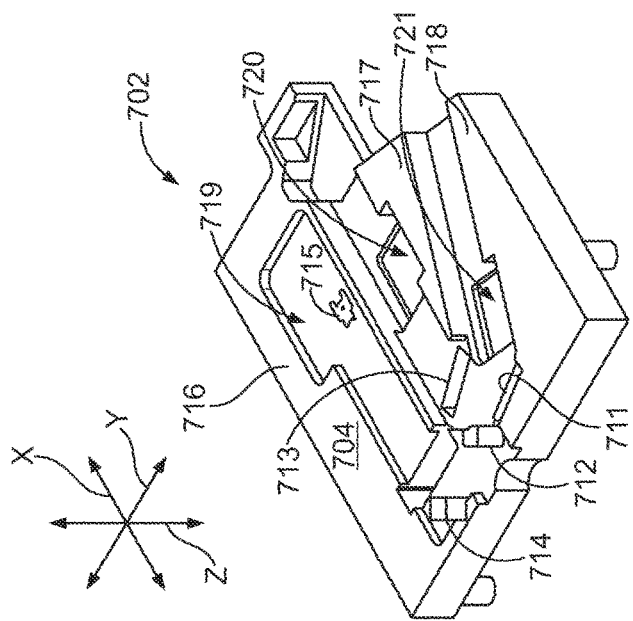
FIG. 41 is a perspective view of an optical base plate that may be used in the imaging system of FIG. 38.

FIGS. 41-42 show a perspective view and plan view, respectively, of the optical base plate 702 that may be used with the imaging system 600 (FIG. 38). In some embodiments of the imaging system 600, one or more of the optical components 621-627, 631-636, and 641-645 (FIG. 38) can have a fixed position in the optical assembly 602 such that the fixed (or static) optical component does not move during operation of the imaging system 600. For example, the base plate 702 is configured to support a plurality of optical components and other parts of the imaging system 600. As shown, the base plate 702 constitutes a substantially unitary structure having a support side (or surface) 704 that faces in a direction along the Z-axis. In the illustrated embodiment, the support side 704 is not continuously smooth, but may have various platforms 716-718, depressions (or receiving spaces) 719-721, and component-receiving spaces 711-714 that are located to arrange the optical assembly 602 in a predetermined configuration. As shown in FIG. 42, each of the component-receiving spaces 711-714 has respective reference surfaces 781-784. In some embodiments, the reference surfaces 781-784 can facilitate orienting and holding corresponding optical components in desired positions.

FIGS. 43 and 44 show a front perspective view and a cutaway rear perspective view, respectively, of an optical device 732. As shown in FIG. 43, the optical device 732 is oriented relative to mutually perpendicular axes 791-793. The axis 791 may extend along a gravitational force direction and/or parallel to the Z-axis illustrated above. In particular embodiments, the optical device 732 is configured to be positioned within the component-receiving space 713 (FIG. 43) of the base plate 702 (only a portion of the base plate 702 is shown in FIGS. 43 and 44).

The component-receiving space 713 has one or more surfaces that define an accessible spatial region where an optical component may be held. These one or more surfaces may include the reference surface(s) described below. In the illustrated embodiment, the component-receiving space 713 is a component cavity of the base plate 701 that extends a depth within the base plate 702. However, the base plate 702 may form the component-receiving space in other manners. For example, in a similar way that the base plate 702 may form a cavity, the base plate 702 may also have one or more raised platforms including surfaces that surround and define the component-receiving space. Accordingly, the base plate 702 may be shaped to partially or exclusively provide the component-receiving space. The base plate 702 may include the reference surface. In alternative embodiments, sidewalls may be mounted on the base plate 702 and configured to define the spatial region. Furthermore, other optical devices mounted to the base plate 702 may define the component-receiving spaces. As used herein, when an element "defines" a component-receiving space, the element may exclusively define the component-receiving space or may only partially define the component-receiving space.

The optical device 732 can be removably mounted to the base plate 702 in the component-receiving space 713, but may be configured to remain in a fixed position during operation of the imaging system. However, in alternative embodiment, the optical device 732 is not positioned within the component-receiving space 713, but may be positioned elsewhere, such as on a platform of the support side 704. In the illustrated embodiment, the optical device 732 includes a mounting device 734 and an optical component 736 that is configured to reflect and/or transmit light therethrough. The mounting device 734 is configured to facilitate holding the optical component 736 in a desired orientation and also removably mount the optical component 736 to the base plate 702. The mounting device 734 includes a component retainer 738 and a biasing element 740 that is operatively coupled to the retainer 738.

In the illustrated embodiment, the optical component 736 comprises an optical filter that transmits optical signals therethrough while filtering for a predetermined spectrum. However, other optical components may be used in alternative embodiments, such as lenses or mirrors. As shown, the optical component 736 may include optical surfaces 742 and 744 that face in opposite directions and define a thickness $T_3$ of the optical component 736 therebetween. As shown, the optical surfaces 742 and 744 may be continuously smooth and planar surfaces that extend parallel to each other such that the thickness $T_3$ is substantially uniform. However, the optical surfaces 742 and 744 may have other contours in alternative embodiments. The optical component 736 may have a plurality of component edges 751-754 (FIG. 43) that define a perimeter or periphery. The periphery surrounds the optical surfaces 742 and 744. As shown, the periphery is substantially rectangular, but other geometries may be used in alternative embodiments (e.g., circular).

The retainer 738 facilitates holding the optical component 736 in a desired orientation. In the illustrated embodiment, the retainer 738 is configured to engage the optical surface 742 and extend around at least a portion of the periphery to retain the optical component 736. For example, the retainer 738 may include a wall portion 756 and a frame extension 758 that extends from the wall portion 756 along the periphery of the optical component 736 (e.g., the component edge 752 (FIG. 43)). In the illustrated embodiment, the frame extension 758 may form a bracket that limits movement of the optical component 736. More specifically, the frame extension 758 may include a proximal arm 760 and a distal arm 762. The proximal arm 760 extends from the wall portion 756 along the component edge 752 and the axis 791. The distal arm 762 extends from the proximal arm 760 along the component edge 751. The distal arm 762 includes a projection or feature 764 that extends toward and engages the optical component 736. Also shown, the retainer 738 may include a grip member 766 that is located opposite the frame extension 758. The grip member 766 and the frame extension 758 may cooperate in limiting movement of the optical component 736 along the axis 793. The retainer 738 may grip a portion of the periphery of the optical component 736.

As shown in FIGS. 43 and 44, the wall portion 756 is configured to engage the optical surface 742. For example, the wall portion 756 has a mating surface 770 (FIG. 43) that faces the optical component 736. In some embodiments, the wall portion 756 includes a plurality of orientation features 771-773 (FIG. 43) along the mating surface 770. The orientation features 771-773 are configured to directly engage the optical surface 742 of the optical component 736. When the orientation features 771-773 directly engage the optical surface 742, the optical surface 742 (and consequently the optical component 736) is positioned in a desired orientation with respect to the retainer 738. As shown in FIG. 43, the reference surface 783 of the component-receiving space 713 also includes a plurality of orientation features 761-763. The orientation features 761-763 are configured to directly engage the optical surface 744. Furthermore, the orientation features 761-763 may be arranged such that each of the orientation features 761-763 generally opposes a corresponding one of the orientation features 771-773.

Also shown in FIG. 44, the wall portion 756 has a non-mating surface 774 that faces in an opposite direction with respect to the mating surface 770 (FIG. 43). The wall portion 756 includes an element projection 776 that extends away from the non-mating surface 774 and the optical component 736. The biasing element 740 is configured to couple to the element projection 776. In the illustrated embodiment, the element projection 776 and the biasing element 740 extend into a slot 778 of the component-receiving space 713. The slot 778 is sized and shaped to receive the biasing element 740. The slot 778 has an element surface 780 that engages the biasing element 740.

Figures 45, 46:
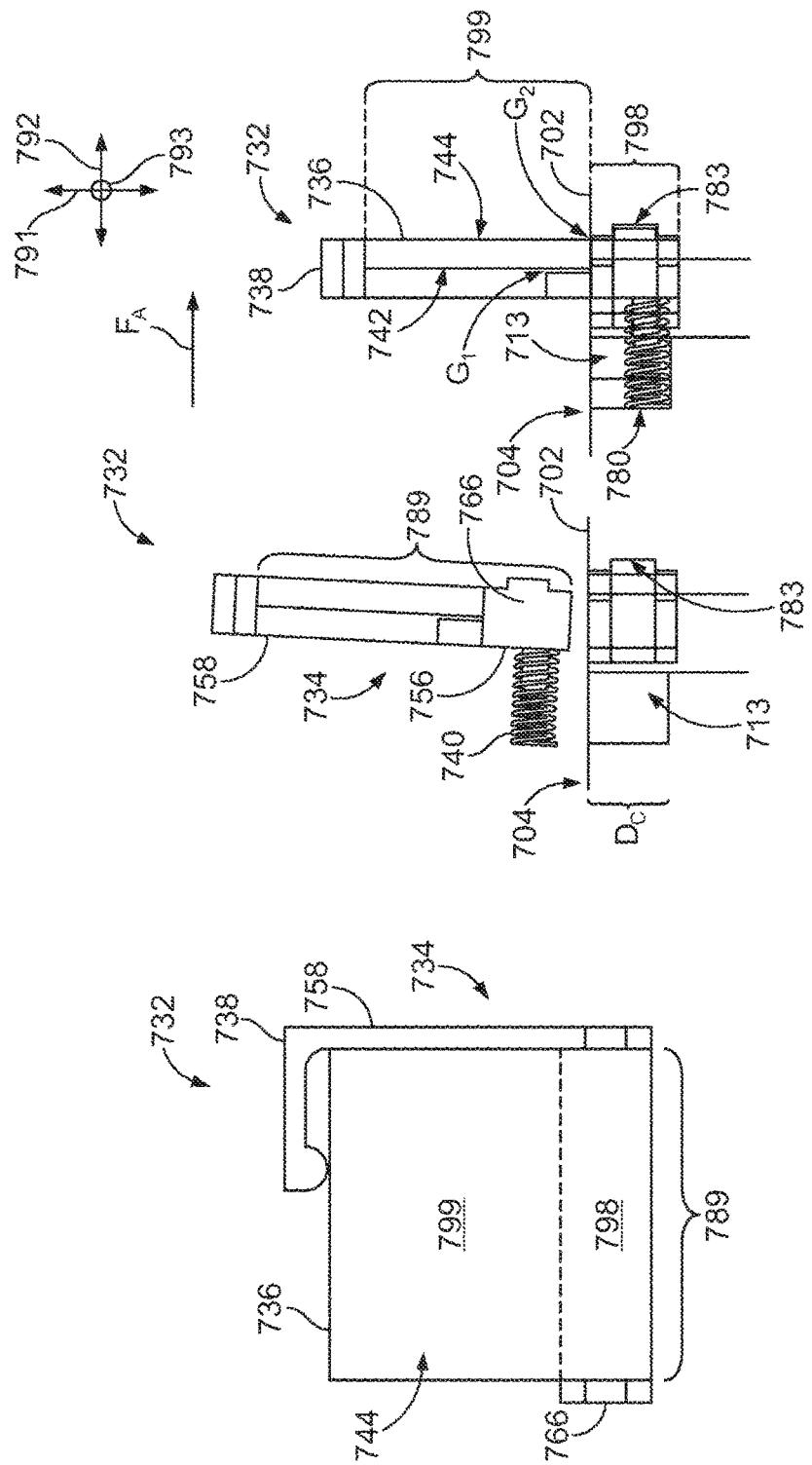
FIG. 45 is a front view of the optical component of FIG. 43.
FIG. 46 is a side view of the optical component of FIG. 43 during a mounting operation.

FIG. 45 shows an isolated front view of the optical device 732, and FIG. 46 shows how the optical device 732 may be removably mounted to the base plate 702. To removably mount the optical component 736, the optical component 736 may be positioned within a component-receiving space 789 of the mounting device 734 that is generally defined by the wall portion 756 (FIG. 46), the frame extension 758, and the grip member 766. In particular embodiments, when the optical component 736 is positioned within the mounting device 734, the optical component 736 is freely held within the component-receiving space 789. For instance, the optical component 736 may not form an interference fit with the retainer 738. Instead, during a mounting operation, the optical component 736 may be held within the component-receiving space 789 by the wall portion 756, the frame extension 758, the grip member 766 and, for example, an individual's hand. However, in alternative embodiments, the optical component 736 may form an interference fit with the retainer 738 or may be confined within a space that is defined only by the retainer 738.

With respect to FIG. 46, during the mounting operation, the biasing element 740 may be initially compressed so that the mounting device 734 may clear and be inserted into the component-receiving space 713. For example, the biasing element 740 may be compressed by an individual's finger to reduce the size of the optical device 732, or the biasing element 740 may be compressed by first pressing the biasing element 740 against the element surface 780 and then advancing the retainer 738 into the component-receiving space 713. Once the optical device 732 is placed within the component-receiving space 713, the stored mechanical energy of the compressed biasing element 740 may move the retainer 738 and the optical component 736 toward the reference surface 783 until the optical surface 744 directly engages the reference surface 783. More specifically, the optical surface 744 may directly engage the orientation features 761-763 (FIG. 43) of the reference surface 783. As shown in FIG. 46, when the optical component 736 is mounted, a small gap $G_1$ may exist between the optical surface 742 and the mating surface 770 (FIG. 43) because of the orientation features 771-773 (FIG. 43), and a small gap $G_2$ may exist between the optical surface 744 and the reference surface 783 because of the orientation features 761-763 (FIG. 43).

In the mounted position, the biasing element 740 provides an alignment force $F_A$ that holds the optical surface 744 against the reference surface 783. The optical and reference surfaces 744 and 783 may be configured to position the optical component 736 in a predetermined orientation. The alignment force $F_A$ is sufficient to hold the optical component 736 in the predetermined orientation throughout operation of the imaging system. In other words, the mounting device 734 and the reference surface 783 may prevent the optical component 736 from moving in a direction along the axis 792. Furthermore, in the mounted position, the projection 764 (FIG. 43) may press against the component edge 751 (FIG. 43) to prevent the optical component 736 from moving in a direction along the axis 791. The frame extension 758 and the grip member 766 may prevent or limit movement of the optical component 736 in a direction along the axis 793. Accordingly, the component-receiving space 713 and the mounting device 734 may be configured with respect to each other to hold the optical component 736 in a predetermined orientation during imaging sessions.

As shown in FIG. 45, when the optical component 736 is in the mounted position, a space portion 798 of the optical surface 744 may face and interface with the reference surface 783, and a path portion 799 of the optical surface 744 may extend beyond the support side 704 into an optical path taken by optical signals. Also shown in FIG. 46, the component-receiving space 713 may extend a depth $D_C$ into the base plate 702 from the support side 704.

The biasing element 740 may comprise any elastic member capable of storing mechanical energy to provide the alignment force $F_A$. In the illustrated embodiment, the elastic member comprises a coil spring that pushes the optical surface 744 against the reference surface 783 when compressed. However, in alternative embodiments, the elastic member and the component-receiving space may be configured such that the elastic member pulls the optical surface against the reference surface when extended. For example, a coil spring may have opposite ends in which one end is attached to the element surface in a slot that extends from the reference surface and another end is attached to the retainer. When the coil spring is extended, the coil spring may provide an alignment force that pulls the optical component against the reference surface. In this alternative embodiment, a rubber band may also be used.

In alternative embodiments, the mounting device 734 may be used to affix the optical component 736 to the base plate 702 using an adhesive. More specifically, the optical component 736 may be held against the reference surface 783 by the mounting device 734. An adhesive may be deposited into the gap $G_2$ between the optical surface 744 and the reference surface 783. After the adhesive cures, the mounting device 734 may be removed while the optical component 736 remains affixed to the reference surface 783 by the adhesive.

Figure 47:
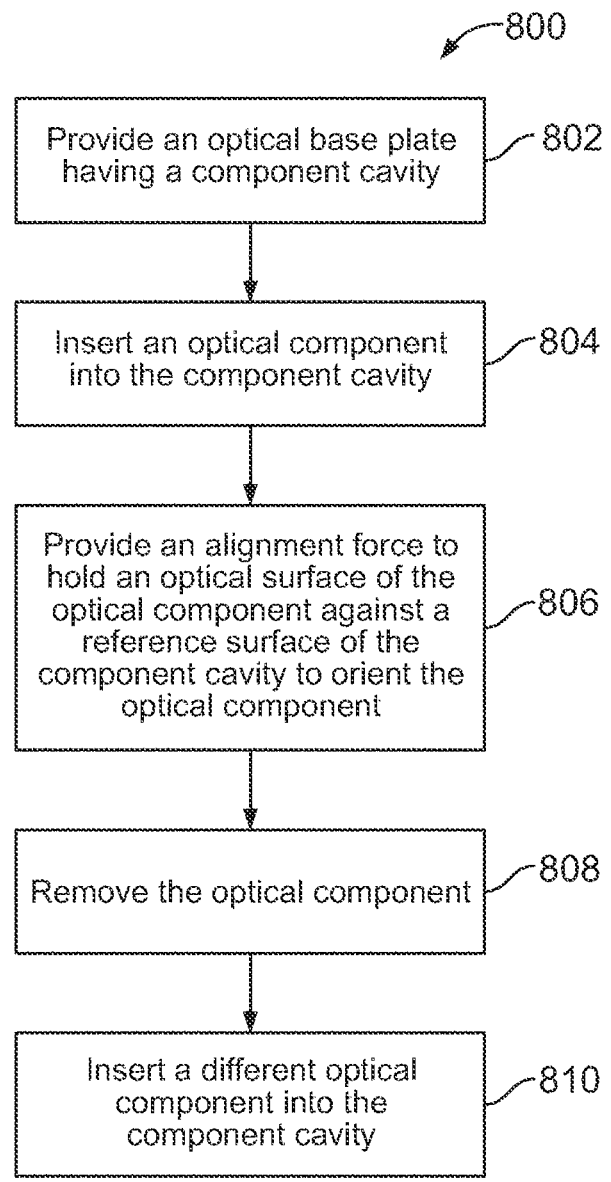
FIG. 47 is a block diagram illustrating a method of assembling an optical train in accordance with one embodiment.

FIG. 47 is a block diagram illustrating a method 800 of assembling an optical train. The method 800 includes providing an optical base plate at 802 that has a component-receiving space. The base plate and the component-receiving space may be similar to the base plate 702 and the component-receiving space 713 described above. The method 800 also includes inserting an optical component at 804 into the component-receiving space. The optical component may be similar to the optical component 736 described above and include an optical surface that is configured to reflect or transmit light therethrough. The optical surface may have a space portion that faces a reference surface of the component-receiving space and a path portion that extends beyond the support side into an optical path. The method 800 also includes providing an alignment force at 806 that holds the optical surface against the reference surface to orient the optical component. The optical and reference surfaces may be configured to hold the optical component in a predetermined orientation when the alignment force is provided. In some embodiments, the method 800 may also include removing the optical component at 808 and, optionally, inserting a different optical component at 810 into the component-receiving space. The different optical component may have the same or different optical qualities. In other words, the different optical component may be a replacement that has the same optical qualities or the different optical component may have different optical qualities.

Figure 48:
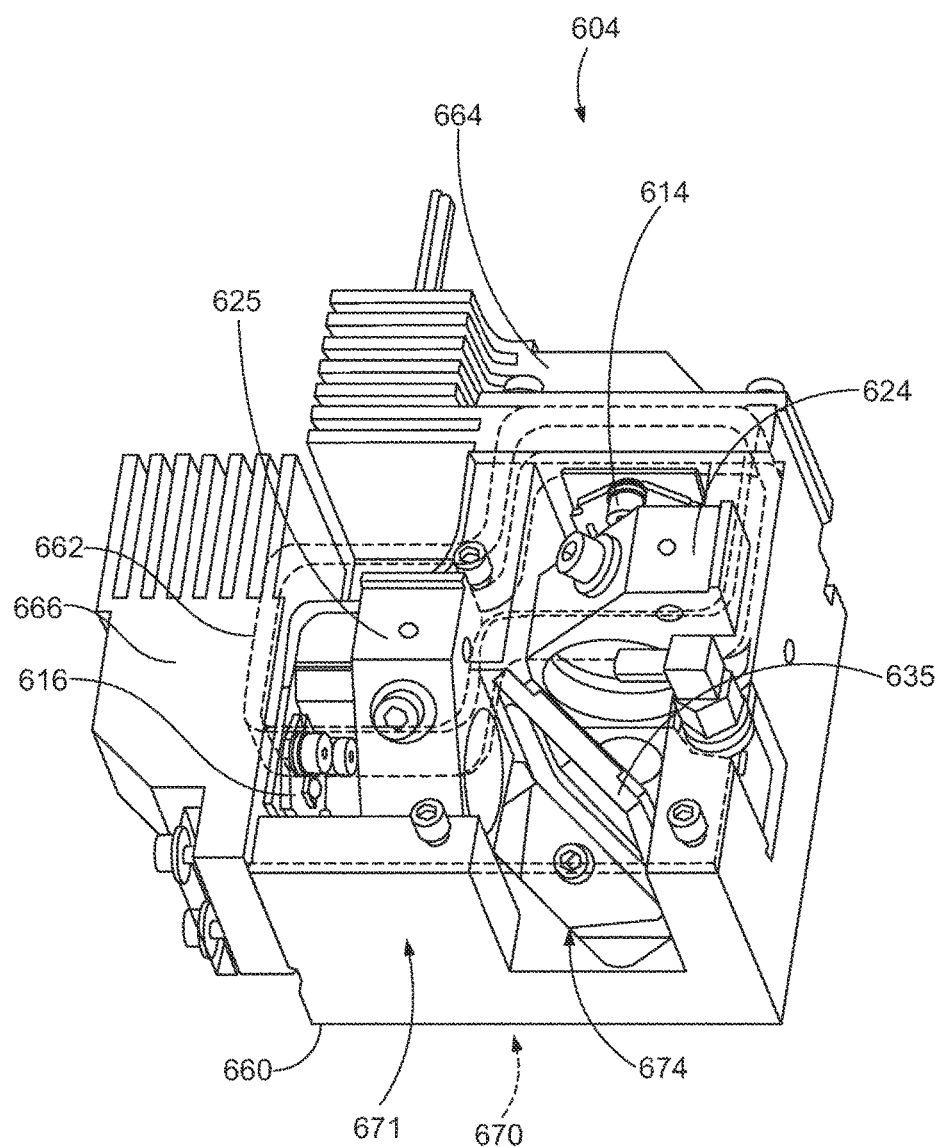
FIG. 48 is a perspective view of a light source module formed in accordance with one embodiment.
Figure 49:
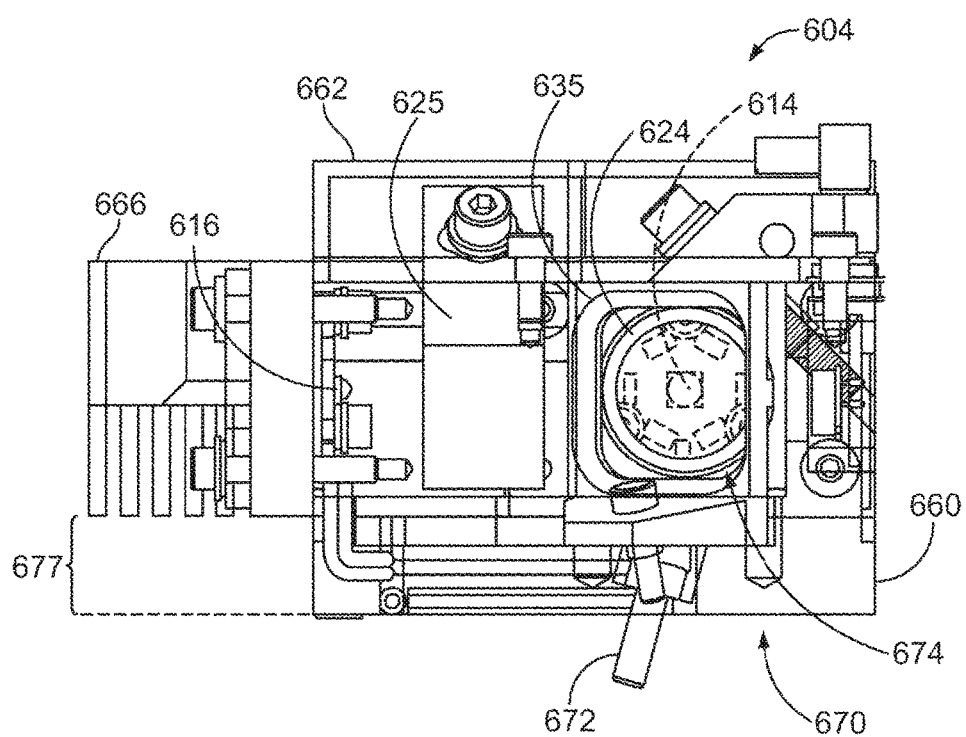
FIG. 49 is a side view of the light source module of FIG. 48.

FIGS. 48 and 49 provide a perspective view and a side view, respectively, of the light source (or excitation light module) 604. As used herein, a light source module includes one or more light sources (e.g., lasers, arc lamps, LEDs, laser diodes) that are secured to a module frame and also includes one or more optical components (e.g., lenses or filters) that are secured to the module frame in a fixed and predetermined position with respect to said one or more light sources. The light source modules may be configured to be removably coupled within an imaging system so that a user may relatively quickly install or replace the light source module. In particular embodiments, the light source module 604 constitutes a SLS module 604 that includes the first and second SLSs 614 and 616. As shown, the SLS module 604 includes a module frame 660 and a module cover 662. A plurality of imaging components may be secured to the module frame 660 in fixed positions with respect to each other. For example, the first and second SLSs 614 and 616, the excitation filter 635, and the lenses 624 and 625 may be mounted onto the module frame 660. In addition, the SLS module 604 may include first and second heat sinks 664 (FIG. 48) and 666 that are configured to transfer thermal energy from the first and second SLSs 614 and 616, respectively.

The SLS module 604 and the module frame 660 may be sized and shaped such that an individual could hold the SLS module 604 with the individual's hands and readily manipulate for installing into the imaging system 600. As such, the SLS module 604 has a weight that an adult individual could support.

The SLS module 604 is configured to be placed within the module-receiving space 719 (FIG. 41) and removably coupled to the base plate 702 (FIG. 41). As shown, the module frame 660 has a plurality of sides including a mounting side 670 and an engagement face 671 (FIG. 48). In the illustrated embodiment, the module frame 660 is substantially rectangular or block-shaped, but the module frame 660 may have other shapes in alternative embodiments. The mounting side 670 is configured to be mounted to the base plate 702 within the module-receiving space 719. As such, at least a portion of the module-receiving space 719 may be shaped to receive and hold the SLS module 604. Similar to the component-receiving space 713, the module-receiving space 719 may be defined by one or more surfaces that provide an accessible spatial region where the SLS module 604 may be held. The surface(s) may be of the base plate 702. For example, in the illustrated embodiment, the module-receiving space 719 is a depression of the base plate 702. The mounting side 670 may have a contour that substantially complements the base plate 702 and, more specifically, the module-receiving space 719. For example, the mounting side 670 may be substantially planar and include a guidance pin 672 (FIG. 49) projecting therefrom that is configured to be inserted into a corresponding hole (not shown) in the base plate 702. The guidance pin 672 may be a fastener (e.g., screw) configured to facilitate removably coupling the module frame 660 to the base plate 702. In particular embodiments, the guidance pin 672 is inserted into the base plate 702 at a non-orthogonal angle. As shown in FIG. 49, the heat sink 666 may be coupled to the module frame 660 such that an offset 676 exists from the mounting side 670 to the heat sink 666.

The module frame 660 may include first and second light passages 682 and 684 that intersect each other at a passage intersection 685. The SLSs 614 and 616 may be secured to the module frame 660 and have fixed positions with respect to each other. The SLSs 614 and 616 are oriented such that optical signals are substantially directed along optical paths through the respective light passages 682 and 684 toward the passage intersection 685. The optical paths may be directed toward the excitation filter 635. In the illustrated embodiment, the optical paths are perpendicular to one another until reaching the excitation filter 635. The excitation filter 635 is oriented to reflect at least a portion of the optical signals generated by the SLS 616 and transmit at least a portion of the optical signals generated by the SLS 614. As shown, the optical signals from each of the SLSs 614 and 616 are directed along a common path and exit the SLS module 604 through a common module window 674. The module window 674 extends through the engagement face 671.

Figure 50:
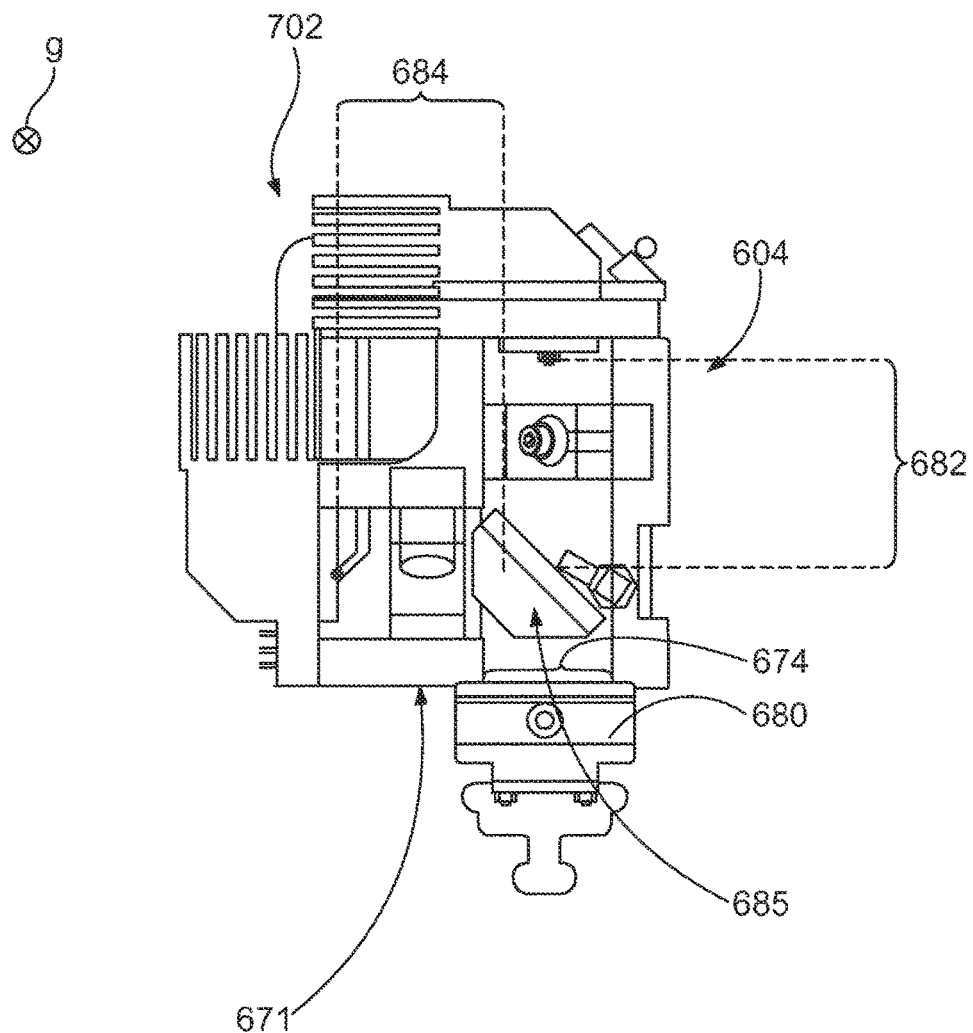
FIG. 50 is a plan view of the light source module of FIG. 48.

FIG. 50 is a plan view of the SLS module 604 mounted onto the base plate 702. In the illustrated embodiment, the SLS module 604 is configured to rest on the base plate 702 such that the gravitational force g facilitates holding the SLS module 604 thereon. As such, the SLS module 604 may provide an integrated device that is readily removed or separated from the optical assembly 600. For example, after removing a housing (not shown) of the assay system or after receiving access to the optical assembly, the SLS module 604 may be grabbed by an individual and removed or replaced. When the SLS module 604 is located on the base plate 702, the engagement face 671 may engage an optical device 680. The optical device 680 may be adjacent to the module window 674 such that the optical signals generated by the SLS module 604 are transmitted through the optical device 680.

Although the illustrated embodiment is described as using an SLS module with first and second SLSs, excitation light may be directed onto the sample in other manners. For example, the SLS module 604 may include only one SLS and another optical component (e.g., lens or filter) having fixed positions with respect to each other in a module frame. Likewise, more than two SLSs may be used. In a similar manner, light modules may include only one laser or more than two lasers.

However, embodiments described herein are not limited to only having modular excitation systems, such as the SLS module 604. For example, the imaging system 600 may use a light source that is not mounted to a module frame. More specifically, a laser could be directly mounted to the base plate or other portion of the imaging system or may be mounted to a frame that, in turn, is mounted within the imaging system.

Returning to FIG. 38, the imaging system 600 may have an image-focusing system 840 that includes the object or sample holder 650, an optical train 842, and the imaging detector 610. The optical train 842 is configured to direct optical signals from the sample holder 650 (e.g., light emissions from the sample area 608 of the flow cell 606) to a detector surface 844 of the imaging detector 610. As shown in FIG. 38, the optical train 842 includes the optical components 623, 644, 634, 633, 621, 631, and 642. The optical train 842 may include other optical components. In the illustrated configuration, the optical train 842 has an object or sample plane 846 located proximate to the sample holder 650 and an image plane 848 located proximate to the detector surface 844. The imaging detector 610 is configured to obtain object or sample images at the detector surface 844.

In some embodiments, the image-focusing system 840 is configured to move the image plane 848 relative to the detector 610 and capture a test image. More specifically, the image plane 848 may be moved such that the image plane 848 extends in a non-parallel manner with respect to the detector surface 844 and intersects the detector surface 844. A location of the intersection may be determined by analyzing the test image. The location may then be used to determine a degree-of-focus of the imaging system 600. In particular embodiments, the image-focusing system 840 utilizes a rotatable mirror that is operatively coupled to an actuator for moving the rotatable mirror. However, the image-focusing system 840 may move other optical components that direct the optical signals to the detector surface 844, or the image-focusing system 840 may move the detector 610. In either case, the image plane 848 may be relatively moved with respect to the detector surface 844. For example, the image-focusing system 840 may move a lens.

In particular embodiments, the imaging detector 610 is configured to obtain test images using a rotatable mirror 642 to determine a degree-of-focus of the imaging system 600. As a result of the determined degree-of-focus, the imaging system 600 may move the sample holder 650 so that the object or sample is located within the sample plane 846. For example, the sample holder 650 may be configured to move the sample area 608 in a z-direction a predetermined distance (as indicated by $\Delta z$).

Figure 51:
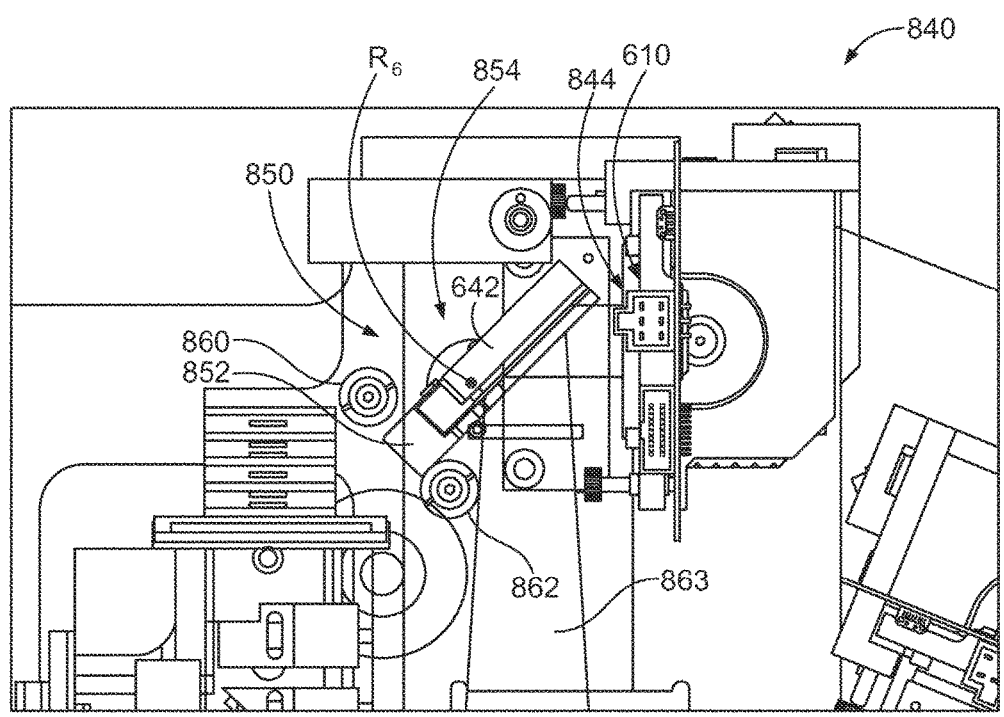
FIG. 51 is a plan view of an image-focusing system in accordance with one embodiment.

FIG. 51 is a plan view that illustrates several of the components in the image-focusing system 840. As shown, the image-focusing system 840 includes a rotatable mirror assembly 850 that includes the mirror 642, a mounting assembly 852 having the mirror 642 mounted thereon, and an actuator or rotation mechanism 854 that is configured to rotate the mounting assembly 852 and the mirror 642 about an axis of rotation $R_6$. The mirror 642 is configured to reflect optical signals 863 that are received from the sample area 608 (FIG. 38) toward the imaging detector 610 and onto the detector surface 844. In the illustrated embodiment, the mirror 642 reflects the optical signals 863 directly onto the detector surface 844 (i.e., there are no intervening optical components that redirect the optical signals 863). However, in alternative embodiments, there may be additional optical components that affect the propagation of the optical signals 863.

In the illustrated embodiment, the image-focusing system 840 also includes positive stops 860 and 862 that are configured to prevent the mirror 642 from rotating beyond predetermined rotational positions. The positive stops 860 and 862 have fixed positions with respect to the axis $R_6$. The mounting assembly 852 is configured to pivot about the axis $R_6$ between the positive stops 860 and 862 depending upon whether sample images or test images are being obtained. Accordingly, the mirror 642 may be rotated between a test position (or orientation) and an imaging position (or orientation). By way of example only, the mirror 642 may be rotated from approximately 5° to approximately 12° about the axis $R_6$ between the different rotational positions. In particular embodiments, the mirror 642 may be rotated approximately 8° about the axis $R_6$.

FIG. 52 is a perspective view of the mirror assembly 850. As shown, the mounting assembly 852 includes an interior frame 864 and a support bracket 866. The interior frame 864 is configured to couple to the mirror 642 and also to the support bracket 866. The interior frame 864 and the support bracket 866 may interact with each other and a plurality of set screws 868 to provide minor adjustments to the orientation of the mirror 642. As such, the mounting assembly 852 may constitute a gimbal mirror mount assembly. Also shown, the mounting assembly 852 is coupled to the rotation mechanism 854. In the illustrated embodiment, the rotation mechanism 854 comprises a direct drive motor. However, a variety of alternative rotation mechanisms may be used, such as direct current (DC) motors, solenoid drivers, linear actuators, piezoelectric motors, and the like. Also shown in FIG. 52, the positive stop 860 may have a fixed position with respect to the rotation mechanism 854 and the axis $R_6$.

As discussed above, the rotation mechanism 854 is configured to rotate or pivot the mirror 642 about the axis $R_6$. As shown in FIG. 52, the mirror 642 has a geometric center C that extends along the axis $R_6$. The geometric center C of the mirror 642 is offset with respect to the axis $R_6$. In some embodiments, the rotation mechanism 854 is configured to move the mirror 642 between the test position and imaging position in less than 500 milliseconds. In particular embodiments, the rotation mechanism 854 is configured to move the mirror 642 between the test position and imaging position in less than 250 milliseconds or less than 160 milliseconds.

FIG. 53 is a schematic diagram of the mirror 642 in the imaging position. As shown, the optical signals 863 from the sample area 608 (FIG. 38) are reflected by the mirror 642 and directed toward the detector surface 844 of the imaging detector 610. Depending upon the configuration of the optical train 842 and the z-position of the sample holder 610, the sample area 608 may be sufficiently in-focus or not sufficiently in-focus (i.e., out-of-focus). FIG. 53 illustrates two image planes 848A and 848B. The image plane 848A substantially coincides with the detector surface 844 and, as such, the corresponding sample image has an acceptable or sufficient degree-of-focus. However, the image plane 848B is spaced apart from the detector surface 844. Accordingly, the sample image obtained when the image plane 848B is spaced apart from the detector surface 844 may not have a sufficient degree-of-focus.

FIGS. 54 and 55 illustrate sample images 870 and 872, respectively. The sample image 870 is the image detected by the imaging detector 610 when the image plane 848A coincides with the detector surface 844. The sample image 872 is the image detected by the imaging detector 610 when the image plane 848B does not coincide with the detector surface 844. (The sample images 870 and 872 include clusters of DNA that provide fluorescent light emissions when excited by predetermined excitation spectra.) As shown in FIGS. 54 and 55, the sample image 870 has an acceptable degree-of-focus in which each of the clusters along the sample image 870 is clearly defined, and the sample image 872 does not have an acceptable degree-of-focus in which each of the clusters is clearly defined.

Figure 56:
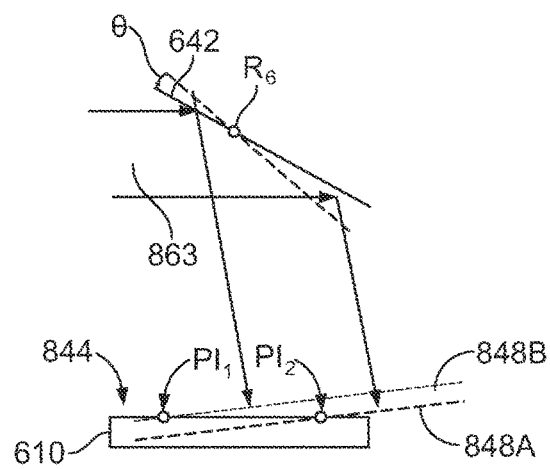
FIG. 56 is a schematic diagram of the rotatable mirror of FIG. 53 in a focusing position.

FIG. 56 is a schematic diagram of the mirror 642 in the focusing position. As shown, the mirror 642 in the focusing position has been rotated about the axis $R_6$ an angle θ. Again, the optical signals 863 from the sample area 608 (FIG. 38) are reflected by the mirror 642 and directed toward the detector surface 844 of the imaging detector 610. However, the optical train 842 in FIG. 56 is arranged so that the image plane 848 has been moved with respect to the detector surface 844. More specifically, the image plane 848 does not extend parallel to the detector surface 844 and, instead, intersects the detector surface 844 at a plane intersection PI. While the mirror 642 is in the focusing position, the imaging system 600 may obtain a test image of the sample area 608. As shown in FIG. 56, the plane intersections PI may occur at different locations on the detector surface 844 depending upon the degree to which the sample area 608 is in-focus during an imaging session.

Figure 57:
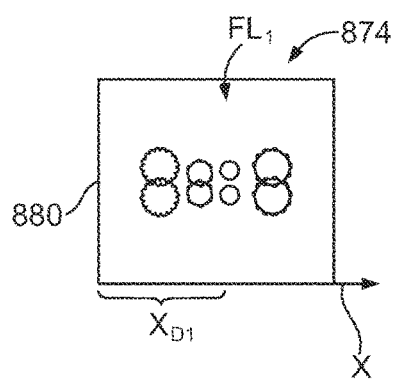
FIGS. 57 and 58 illustrate test images that may be obtained by the image-focusing system of FIG. 51.
Figure 58:
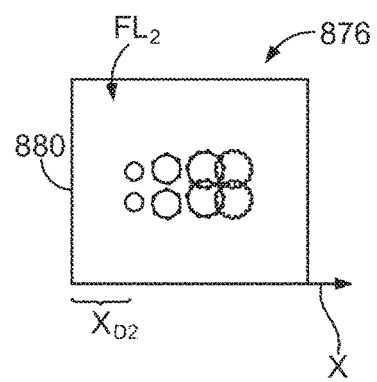

For example, FIGS. 57 and 58 illustrate test images 874 and 876, respectively. The test image 874 represents the image obtained when the sample area 608 is in-focus, and the test image 876 represents the image obtained when the optical train 842 is out-of-focus. As shown, the test image 874 has a focused region or location $FL_1$ that is located a distance $XD_1$ away from a reference edge 880, and the test image 876 has a focused region or location $FL_2$ that is located a distance $XD_2$ away from a reference edge 880. The focused locations $FL_1$ and $FL_2$ may be determined by an image analysis module 656 (FIG. 38).

To identify the focused locations $FL_1$ and $FL_2$ in the test images 874 and 876, the image analysis module 656 may determine the location of an optimal degree-of-focus in the corresponding test image. More specifically, the analysis module 656 may determine a focus score for different points along the x-dimension of the test images 874 and 876. The analysis module 656 may calculate the focus score at each point based on one or more image quality parameters. Examples of image quality parameters include image contrast, spot size, image signal to noise ratio, and the mean-square-error between pixels within the image. By way of example, when calculating a focus score, the analysis module 656 may calculate a coefficient of variation in contrast within the image. The coefficient of variation in contrast represents an amount of variation between intensities of the pixels in an image or a select portion of an image. As a further example, when calculating a focus score, the analysis module 656 may calculate the size of a spot derived from the image. The spot can be represented as a Gaussian spot and size can be measured as the full width half maximum (FWHM), in which case smaller spot size is typically correlated with improved focus.

After determining the focused location FL in the test image, the analysis module 656 may then measure or determine the distance XD that the focused location FL is spaced apart or separated from the reference edge 880. The distance XD may then be correlated to a z-position of the sample area 608 with respect to the sample plane 846. For example, the analysis module 656 may determine that the distance $XD_2$ shown in FIG. 58 corresponds to the sample area 608 be located a distance Δz from the sample plane 846. As such, the sample holder 650 may then be moved the distance Δz to move the sample area 608 within the sample plane 846. Accordingly, the focused locations FL in test images may be indicative of a position of the sample area 608 with respect to the sample plane 846. As used herein, the phrase "being indicative of a position of the object (or sample) with respect to the object (or sample) plane" includes using the factor (e.g., the focused location) to provide a more suitable model or algorithm for determining the distance Δz.

FIG. 59 is a block diagram illustrating a method 890 for controlling focus of an optical imaging system. The method 890 includes providing an optical train at 892 having a rotatable mirror that is configured to direct optical signals onto a detector surface. The detector surface may be similar to the detector surface 844. The optical train may have an object plane, such as the sample plane 846, that is proximate to an object. The optical train may also have an image plane, such as the image plane 848, that is proximate to the detector surface. The rotatable mirror may be rotatable between an imaging position and a focusing position.

The method 890 also includes rotating the mirror at 894 to the focusing position and obtaining a test image of the object at 896 when the mirror is in the focusing position. The test image may have an optimal degree-of-focus at a focused location. The focused location may be indicative of a position of the object with respect to the object plane. Furthermore, the method 890 may also include moving the object at 898 toward the object plane based on the focused location.

It is to be understood that the above description is intended to be illustrative, and not restrictive. For example, the above-described embodiments (and/or aspects thereof) may be used in combination with each other. In addition, many modifications may be made to embodiments without departing from the of the scope invention in order to adapt a particular situation or material. While the specific components and processes described herein are intended to define the parameters of the various embodiments, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A fluidic device for analyzing samples, the fluidic device comprising:
    a flow cell including inlet and outlet ports and a flow channel extending therebetween, the flow cell configured to hold a sample-of-interest;
    a housing having a reception space that is configured to receive the flow cell, the reception space being sized and shaped to permit the flow cell to float relative to the housing;
    a gasket coupled to the housing, the gasket having inlet and outlet passages and comprising a compressible material, the gasket being positioned relative to the reception space so that the inlet and outlet ports of the flow cell are approximately aligned with the inlet and outlet passages of the gasket, respectively, and
    a cover member rotatably coupled to the housing so as to be rotatable about an axis of rotation extending through the housing between a mounted position and a disengaged position;
    wherein a top surface of the cover member is substantially flush with a top surface of the housing when the cover member is set in the mounted position.

2. The fluidic device of claim 1, wherein the cover member includes the gasket and a cover material, wherein the cover material and the gasket are co-molded, the compressible material of the gasket being more compressible than the cover material.

3. The fluidic device of claim 1, wherein the cover member includes the gasket and a cover material, the inlet and outlet passages of the gasket being approximately aligned with the inlet and outlet ports when the cover member is in the mounted position.

4. The fluidic device of claim 1, wherein the cover member includes the gasket and a cover material, wherein the housing further comprises fin projections and wherein the cover member extends between the fin projections.

5. The fluidic device of claim 1, wherein the flow cell has a plurality of edges that extend along a cell plane and define a perimeter of the flow cell, the gasket configured to press against one of the edges when the inlet and outlet passages are approximately aligned, the gasket limiting movement of the flow cell within the reception space along the cell plane.

6. The fluidic device of claim 5, wherein the flow cell has first and second cell sides that face in opposite directions, the first and second cell sides extending along the cell plane, wherein the gasket also presses against one of the first and second cell sides thereby limiting movement in a direction that is perpendicular to the cell plane.

7. The fluidic device of claim 6, wherein the gasket is movable with respect to the housing and flow cell, the inlet and outlet passages being approximately aligned with the inlet and outlet ports when the gasket is mounted over the flow cell.

8. The fluidic device of claim 1, wherein the flow channel comprises an imaging portion and a non-imaging portion, wherein imaging and nonimaging portions are fluidicly joined by a curved portion, the imaging and non-imaging portions extending parallel to each other,
    wherein the inlet port is in fluid communication with the imaging portion of the flow channel, and wherein the outlet port is in fluid communication with the non-imaging portion of the flow channel.

9. The fluidic device of claim 8, wherein the inlet port and the outlet port are located proximate to each other at one end of the flow cell.

10. The fluidic device of claim 9, wherein the spacing between the inlet port and the outlet port is 3 mm or less.

11. The fluidic device of claim 8, wherein the width of the imaging portion of the flow channel is larger than the width of the non-imaging portion of the flow channel.

12. The fluidic device of claim 1, wherein the length of the substrate is 30 mm or less, the width of the substrate is 15 mm or less and the height of the substrate is 1.5 mm or less.

13. The fluidic device of claim 8, wherein the curved portion of the flow channel comprises a non-continuous contour that fluidicly joins the imaging portion of the flow channel with the non-imaging portion of the flow channel.

14. The fluidic device of claim 13, wherein the curved portion of the flow channel comprises a tapering portion and an intermediate portion,
    wherein the tapering portion connects the imaging portion with the intermediate portion, and
    wherein the width of the tapering portion reduces in size from the imaging portion of the flow channel to the intermediate portion.

15. The fluidic device of claim 1, further comprising an identification transmitter positioned in a cavity of the housing.

16. The fluidic device of claim 15, wherein the identification transmitter comprises and RFID tag.

17. The fluidic device of claim 1, wherein the housing comprises a loading end and a receiving end, the reception space extends from the loading end and terminates along the housing, and the axis of rotation is proximate the receiving end such that the cover member extends between the reception space and the receiving end when set in the mounted position.

* * * * *

UNITED STATES PATENT AND TRADEMARK OFFICE
CERTIFICATE OF CORRECTION

PATENT NO. : 10,220,386 B2
APPLICATION NO. : 14/550956
DATED : March 5, 2019
INVENTOR(S) : Williamson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 632 days.

Signed and Sealed this
Twenty-ninth Day of October, 2019

Andrei Iancu
*Director of the United States Patent and Trademark Office*